(12) United States Patent
Chang et al.

(10) Patent No.: US 10,947,270 B2
(45) Date of Patent: Mar. 16, 2021

(54) TARGETED PRODRUG CYTOSINE DEAMINASE FUSION CARRIER AND APPLICATION THEREOF

(71) Applicant: National Yang-Ming University, Taipei (TW)

(72) Inventors: C. Allen Chang, Taipei (TW); Hsin-Ell Wang, Taipei (TW); Jia-Je Li, Taipei (TW); Shun-Fu Chang, Taipei (TW); Roy Chen-Chih Wu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 16/247,489

(22) Filed: Jan. 14, 2019

(65) Prior Publication Data

US 2019/0211057 A1 Jul. 11, 2019

Related U.S. Application Data

(63) Continuation-in-part of application No. 14/953,172, filed on Nov. 27, 2015, now Pat. No. 10,202,432.

(30) Foreign Application Priority Data

Aug. 27, 2015 (TW) .............................. 104128165 A

(51) Int. Cl.
| | | |
|---|---|---|
| *C07K 5/09* | (2006.01) | |
| *C12N 9/78* | (2006.01) | |
| *A61K 51/04* | (2006.01) | |
| *A61K 51/08* | (2006.01) | |

(52) U.S. Cl.
CPC .......... *C07K 5/0817* (2013.01); *A61K 51/048* (2013.01); *A61K 51/082* (2013.01); *C12N 9/78* (2013.01); *C07K 2319/01* (2013.01)

(58) Field of Classification Search
None
See application file for complete search history.

(56) References Cited

FOREIGN PATENT DOCUMENTS

| CN | 101824406 | * | 9/2010 | ............... C12N 9/96 |
| WO | WO 97/26918 | * | 7/1997 | ............. A61K 47/48 |

OTHER PUBLICATIONS

Wang et al. A fusion protein of RGD4C and β-lactamase has a favorable targeting effect in its use in antibody enzyme prodrug therapy. Int. J. Mol. Sci. 16, 9625-9634, 2015. (Year: 2015).*
Spooner et al. A novel vascular endothelial growth factor-directed therapy that selectively activates cytotoxic prodrugs. Brit. J. Cancer, 88, 16221630, 2003. (Year: 2003).*

* cited by examiner

*Primary Examiner* — Elly-Gerald Stoica
(74) *Attorney, Agent, or Firm* — Muncy, Geissler, Olds and Lowe, P.C.

(57) ABSTRACT

The present invention provides a targeted prodrug enzyme fusion carrier comprising a targeted molecule and a prodrug enzyme. The targeted prodrug enzyme fusion carrier can effectively identify and bind to tumor cells and tumor-induced tumor angiogenesis. The targeted prodrug enzyme fusion carrier also has a targeted prodrug enzyme fusion protein and a theranostic system utilizing the method of in vivo nuclear medicine for the clinical diagnosis and treatment of individual patients with tumors.

9 Claims, 44 Drawing Sheets
(8 of 44 Drawing Sheet(s) Filed in Color)
Specification includes a Sequence Listing.

DTPA-yCD

Radiochemical purity   54%

54%

DTPA-
RGD4C-yCD

Radiochemical purity   73%

72%

DTPA-yCD

Radiochemical purity    84%        95%

DTPA-
RGD4C-yCD

Radiochemical purity    89%        96%

DTPA-yCD

Radiochemical purity     96%

DTPA-
RGD4C-yCD

Radiochemical purity     97%

TARGETED PRODRUG CYTOSINE DEAMINASE FUSION CARRIER AND APPLICATION THEREOF

CROSS-REFERENCE TO RELATED APPLICATIONS

This application is a Continuation-in-Part of U.S. application Ser. No. 14/953,172, entitled "DUAL TARGETING DRUG CARRIER AND APPLICATION THEREOF", filed on Nov. 27, 2015, which claims the benefit of this Non-provisional application claims priority under 35 U.S.C. § 119(a) on Patent Application No(s). 104128165 filed in Taiwan, Republic of China Aug. 27, 2015.

The disclosures of the above applications are incorporated herein by reference.

FIELD OF THE INVENTION

The present invention relates to a targeted prodrug enzyme fusion carrier, comprising a target molecule and a prodrug enzyme, which can effectively identify and bind the tumor cells, angiogenic endothelial cells and microenvironment in cancer tissues. This targeted prodrug enzyme fusion carrier has a targeted prodrug drug fusion protein that also can be used in nuclear medicine for diagnosis and treatment of cancer after been labeled by radionuclides.

BACKGROUND OF THE INVENTION

Cancer is the leading cause of death in the United States, and cancer mortality continues to increase. Cancer is that the cells can not be normally divided, grown and differentiated. The initial clinical manifestations of cancer are highly heterogeneous and almost 70 cancer types can develop in human organs and tissues due to various different molecular disease mechanisms. Unfortunately, some cancers may have no actual symptoms until the end of the disease, so it is extremely difficult to treat and prognosticate diseases.

Cancer treatment usually includes surgery, chemotherapy and/or radiotherapy. Currently, all therapies have serious side effects and reduce the quality of life. Most chemotherapeutic drugs act on both normal and cancerous tissues. Therefore, one of the challenges in the treatment of cancerous tumors is to maximize the killing of cancer cells while minimizing the damage to normal tissues. Depending on the route of administration of the drug (e.g., intravenous) and its properties (e.g., its physical and pharmacokinetic properties), usually only a small fraction of the dose reaches the target cell, while the rest acts on other tissues or quickly disappears.

In order to improve the delivery efficiency and reduce the toxicity in non-cancerous cancer cells, there have been various ways of delivering drugs to specific sites in the human body. For example, the monoclonal antibodies are used to treat cancer. Antibodies provide target selectivity, but they are still expensive and have the problems with interaction with non-target cells.

Due to the instability and high variability of tumor cells, its high drug resistance to drugs remains unresolved. Tumor tissue secretes a large number of angiogenic factors to activate vascular endothelial cells for angiogenesis as one of the characteristics of tumor growth. Through the new blood vessels, in addition to providing the nutrients needed for tumor growth, it also promotes the metastasis of tumor cells. In recent years, scientific research has begun to treat tumors in angiogenic endothelial cells of tumor tissues. The main reason is that vascular endothelial cells have high genetic stability and are more susceptible to drug stimulation, so the target therapeutic drugs are designed for tumor tissue angiogenesis systems. In addition to the high specificity of the original target treatment and low normal tissue toxicity, the target therapeutic drug may also solve the problem of drug resistance.

In recent years, efforts have been made to study targeted enzyme prodrug therapy, the prodrug is designed for the enzyme only in tumor cells. Low-toxic prodrugs are converted into high-toxic drugs via enzyme from targets to tumor cells, achieving tumor-killing effects, and low toxic drug exposure is also limited to normal tissue damage. In the prodrug carrier system, the antibody-directed enzyme prodrug therapy (ADEPT) is most representative, an antigen that is specifically expressed on the surface of the tumor is bound with the corresponding antibody enzyme fusion protein, after the unbound antibody enzyme fusion protein is removed from the body, it is followed by a less toxic prodrug. The prodrug reaches the tumor and then it is converted into a toxic drug by the enzyme.

For example, cytosine deaminase (CD) is an enzyme secreted by yeast or bacteria that can convert the low-toxic prodrug 5-fluorocytosine (5-FC) into a 5-fluorouracil (5-FU that inhibits DNA and protein synthesis). In the past, the literature pointed out that 5-FU can effectively inhibit the growth of cancer cells, but no effective treatment system has been developed yet. The main reason is that there is no good target molecule.

The application entitled "DUAL TARGETING DRUG CARRIER AND APPLICATION THEREOF" previously applied by the inventors has been granted the patent by the Republic of China and the United States. It shows that the developed target molecule has good target capability and can provide a good target molecule. It was known that the short peptide sequence such as CNGRC peptide (0.6 kDa) was used as the targeted molecule of the targeted prodrug enzyme fusion protein.

However, tumor cells are highly unstable and variable, and they are resistant to drugs during treatment. Currently, various drugs and diagnostic agents are still slow and non-effective in improving the survival of cancer patients. A low toxic prodrug to be developed and converted into highly toxic drug through the enzyme of tumor cells is effective, stable and specific to achieve tumor killing, which is a problem that needs to be solved urgently.

SUMMARY OF THE INVENTION

In view of the above-mentioned problems, the present invention provides a novel carrier used for diagnosing and treating cancer. A targeted prodrug enzyme fusion carrier of the present invention uses single or dual target as a targeted molecule, which can ensure that the targeted prodrug enzyme fusion carrier of the present invention can effectively identify and bind the tumor cells and the molecules of tumor angiogenesis. The targeted prodrug enzyme fusion carrier of the present invention can effectively reduce the pharmaceutical costs.

The present invention provides a targeted prodrug enzyme fusion carrier comprising a target molecule and a prodrug enzyme, wherein the target molecule comprises RGD, RGD4C, VEGF, EGF, RGD-EGF, RGD-VEGF, RGD4C-EGF and RGD4C-VEGF.

In one embodiment, the prodrug enzyme comprises deaminase, pyrimidine deaminase, cytosine deaminase, yCD, EcCD, *E. coli*. cytosine deaminase (EcCD) mutants, purine deaminase, adenine deaminase, guanine deaminase, 8-oxoguanine deaminase, 5'-deoxyadenosine deaminase, uracil phosphoribosyltransferase, thymidine kinase, penicillin amidase, alkaline phosphatase, alcohol dehydrogenase, β-lactamase, β-glucoronidase, carboxyesterases, carboxypeptidase A, carboxypeptidase G2, glycosidases and nitroreductase.

In one embodiment of the present invention, the targeted prodrug enzyme fusion carrier further comprises a marker molecule, wherein the marker molecule includes a radionuclide, indium-111 ($^{111}$In), gallium-67, gallium-68, yttrium-90, lutetium-177, and a fluorescent protein.

In one embodiment, the metal chelating agent comprises DTPA, NOTA and DOTA.

Detailed description of the invention is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a schematic diagram for the carrier and the gene; FIG. 1B is the purified protein analyzed by SDS-PAGE; and FIG. 1C shows the purified protein analyzed by western blot method and detected by anti-His6-tag antibody (Lane 1: yCD (18.7 kDa), lane 2: RGD4C-yCD (19.6 kDa), lane 3: yCD/UPRT (43.1 kDa), lane 4: RGD4C-yCD/UPRT (44.1 kDa)).

FIG. 2A shows the consumption of 5-FC and FIG. 2B shows the formation amount of 5-FU. The measured data was used to plot the enzyme kinetic curve that takes the substrate concentration [S] as the x-axis and takes the initial reaction rate $V_0$ as the y-axis, FIG. 3B shows that RGD4C-yCD and RGD4C-yCD/UPRT are respectively added into the competing objects (RGDfv peptide) with different concentrations, to observe the inhibition of RGD4C-yCD and RGD4C-yCD/UPRT bound to integrin $α_vβ_3$. (*compared with untreated RGDfv group, P<0.05)

FIG. 4A shows the expression quantity of αv integrin protein in various cell lines; FIG. 4B shows the expression quantity of $β_3$ integrin protein in various cell lines; and FIG. 4C shows the expression quantity of β-actin protein in various cell lines, respectively.

FIG. 5A, FIG. 5B, and FIG. 5C are respectively represented HUVEC cells, U87MG cells, MCF-7 cells seeded in 96-well plates for 24 hours, and then RGD4C-yCD, yCD, RGD4C-yCD/UPRT and yCD/UPRT with different concentrations are added for cells binding assay. After reacted with anti-His-HRP antibody and TMB substrate, ELISA reader (OD450 nm) is used to detect the amount of recombinant protein bound to the cells, and the binding curve is drawn. The nonlinear curve of the prism software is used to make a diagram and calculate the dissociation constant ($K_d$).

FIGS. 8A-8D show that the fluorescence microscopy is used to observe the binding and distribution of RGD4C-yCD, yCD, RGD4C-yCD/UPRT and yCD/UPRT fusion proteins in HUVEC and U87MG cells. Wherein, FIGS. 8A-B show that the HUVEC cells incubated with culture medium containing RGD4C-yCD and RGD4C-yCD/UPRT protein at 4° C. (FIG. 8A) or 37° C. (FIG. 8A) for 2 hours, and then the fluorescent staining is performed for the cells, and the confocal fluorescence microscope is used to observe the distribution of protein in cells; FIGS. 8C-D show that the U87MG cells incubated with culture medium containing RGD4C-yCD and RGD4C-yCD/UPRT protein at 4° C. (FIG. 8C) or 37° C. (FIG. 8D) for 2 hours, and then the fluorescent staining is performed for the cells, and the confocal fluorescence microscope is used to observe the distribution of protein in cells. (Green signal: $β_3$ integrin; red signal: anti-His6-tag (also represents the signal of the fusion protein); blue signal: Hoechst 33342 cell nuclear stain) (Calibration scale: 20 μm).

FIGS. 9A-9D show the cell apoptosis assay of the yCD series fusion protein combined with 5-FC in HUVEC and U87MG cells. Wherein, FIG. 9A and FIG. 9C show that the HUVEC and U87MG cells were treated with 500 nM yCD series proteins and combined with 5-FC at different concentrations. And then TUNEL assay kit was used to detect the cell apoptosis (red signal: DNA fragment detected by TUNEL assay kit; blue signal: Hoechst 33342 cell nuclear stain). Cells of the control groups were only incubated with different concentrations of 5-FU or 5-FC without protein treatment. FIG. 9B and FIG. 9D show that the TUNEL fluorescence image was quantified by MetaMorph software. (*P value<0.05; Calibration scale: 20 μm)

FIGS. 10A-10C show the design, expression and purification of EcCD series fusion protein (EcCD_WT, RGD4C-EcCD_WT, EcCD_D314A, RGD4C-EcCD_D314A, RGD-VEGF-EcCD_WT, RGD4C-VEGF-EcCD_WT, RGD-EGF-EcCD_WT, RGD4C-EGF-EcCD_WT, EcCD_WT-RGD-EGF, EcCD_WT-RGD4C-EGF, RGD-VEGF-EcCD_D314A, RGD4C-VEGF-EcCD_D314A, EcCD_D314A-RGD-EGF, EcCD_D314A-RGD4C-EGF, RGD-EGF-EcCD_D314A and RGD4C-EGF-EcCD_D314A). Wherein, FIG. 10A is a schematic diagram for carrier and gene; FIG. 10B shows the analysis of purified protein by SDS-PAGE; and FIG. 10C shows the analysis of purified protein by western blot method using horseradish peroxidase (HRP)-tagged anti-His6 antibody (Lane 1: EcCD_WT (48.8 kDa), Lane 2: EcCD_D314A (48.7 kDa), Lane 3: RGD4C-EcCD_WT (49.9 kDa), Lane 4: RGD4C-EcCD_D314A (49.9 kDa)).

FIG. 12A shows that the EcCD series fusion protein and yCD protein are cultured in 100% FBS for 0-24 hours, then the enzyme kinetics is determined, and $K_{cat}/K_m$ is used to show the catalytic efficiency and specificity of the enzyme to express the enzyme activity, culture for 0 hours to take the control group as a denominator, culture for 1 to 24 hours to take the experimental group as a numerator. FIG. 12B shows that the EcCD fusion protein and yCD protein are cultured in 10% FBS for 0-24 hours, then the enzyme kinetics is determined, and $K_{cat}/K_m$ is used to show the catalytic efficiency and specificity of the enzyme to express the enzyme activity; and FIG. 12C shows that the EcCD fusion protein and yCD protein are cultured in 3 mg/ml transferrin for 0-24 hours, then the enzyme kinetics is determined, and $K_{cat}/K_m$ is used to show the catalytic efficiency and specific enzyme activity.

FIGS. 13A-13B show the binding activity and specificity test of EcCD fusion protein and αvβ3 integrin receptor. Wherein, FIG. 13A shows that ELISA is used to analyze the binding of the EcCD fusion protein and the $α_vβ_3$ integrin receptor, and calculate the $K_d$ value of the binding; and FIG. 13B shows that the competing objects at different concentrations (RGDfv peptide) are added to the EcCD fusion protein, and observe the binding inhibition of EcCD fusion protein and $α_vβ_3$ integrin. (***compared with untreated RGDfv group, P value<0.001, indicating a significant difference)

FIGS. 14A-14E show the binding activity and specificity test of EcCD fusion protein and U87MG, HUVEC and MCF-7 cell strain. Wherein, FIGS. 14A-14C show that an ELISA method is used to analyze the binding of EcCD fusion protein and U87MG, HUVEC and MCF-7 cells, and calculate the $K_d$ value of the binding; FIG. 14D and FIG. 14E show that the competing objects at different concentrations (RGDfv peptide) are respectively added to the EcCD fusion protein, and observe the binding inhibition of EcCD fusion protein and cell strain U87MG, HUVEC of high expression of $α_vβ_3$ integrin. (***compared to the untreated RGDfv group, P value<0.001, indicating a statistically significant difference)

FIG. 17A shows yCD protein, FIG. 17B shows RGD4C-yCD protein, FIG. 17C shows DTPA-yCD protein, and FIG. 17D shows DTPA-RGD4C-yCD protein.

FIGS. 23A-23J shows a instant thin-layer chromatography (ITLC) of $^{111}$In-DTPA-yCD and $^{111}$InDTPA-RGD4C-yCD. FIG. 23A and FIG. 23B show the indium-111 labeled DTPA-yCD and DTPA-RGD4C-yCD, as well as the indium- 111 reacted with DTPA-yCD and DTPA-RGD4C-yCD at 37° C. for 1 hour at a specific activity of 30 µCi/µg; FIG. 23C and FIG. 23D show that DTPA added with a 10-fold molar excess of DTPA-yCD and DTPA-RGD4C-yCD is reacted at room temperature for 1 hour to remove free indium-111 which is not chelated by the DTPA; FIG. 23E and FIG. 23F show that $^{111}$In-DTPA-yCD and $^{111}$In-DTPA-RGD4C-yCD are purified and concentrated by centrifugation for 2 times. FIG. 23G and FIG. 23H show that $^{111}$In-DTPA-yCD and $^{111}$In-DTPA-RGD4C-yCD are purified and concentrated by centrifugation for 4 times. FIG. 23I and FIG. 23J shows that $^{111}$In-DTPA-yCD and $^{111}$In-DTPA-RGD4C-yCD are purified by centrifugation for 5 times, and the solution is replaced from pH 5.5 to pH 7 HEPES buffer. Thin layer analysis conditions: the stationary phase is ITLC-SG, the mobile phase is 0.5M, pH 4.6 citrate buffer solution.

DETAILED DESCRIPTION OF THE INVENTION

Figure 1A:
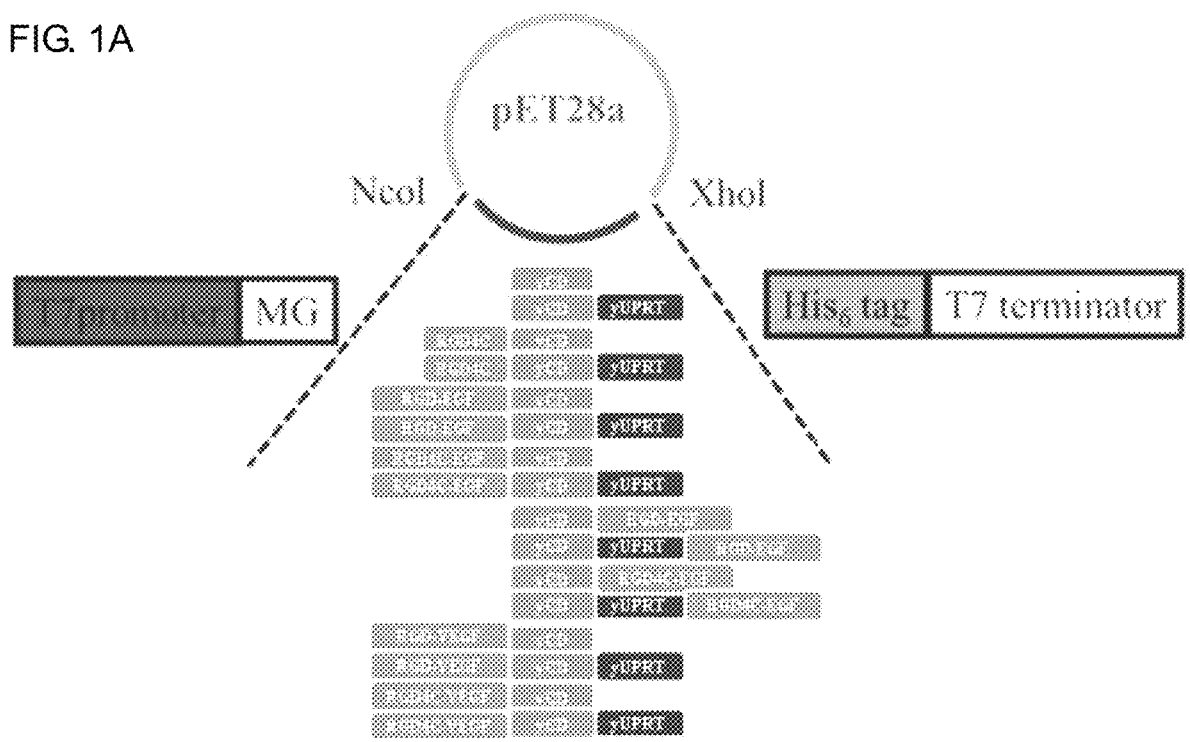
FIGS. 1A-1C show the recombinant protein design, expression and purification of RGD4C-yCD, yCD, RGD4C-yCD/UPRT, yCD/UPRT, RGD-VEGF-yCD, RGD4C-VEGF-yCD, RGD-EGF-yCD, RGD4C-EGF-yCD, yCD-RGD-EGF, yCD-RGD4C-EGF, RGD-VEGF-yCD/UPRT, RGD4C-VEGF-yCD/UPRT, RGD-EGF-yCD/UPRT, RGD4C-EGF-yCD/UPRT, yCD/UPRT-RGD-EGF as well as yCD/UPRT-RGD4C-EGF.

The present invention provides a targeted prodrug enzyme fusion carrier, comprising a target molecule and a prodrug enzyme. The target molecule is selected from, for example, but not limited to, arginine-glycine-aspartic acid (RGD), RGD4C, vascular endothelial growth factor (VEGF), epidermal growth factor (EGF) arginine-glycine-aspartic acid-epidermal growth factor (RGD-EGF), arginine-glycine-aspartic acid-vascular endothelial growth factor (RGD-VEGF), RGD4C-EGF and RGD4C-VEGF.

In one embodiment, the prodrug enzyme is selected from, for example, but not limited to, deaminase, pyrimidine deaminase, cytosine deaminase, yeast cytosine deaminase (yCD) (SEQ ID NO: 1), *E. coli.* cytosine deaminase (EcCD), *E. coli.* cytosine deaminase (EcCD) mutants, purine deaminase, adenine deaminase, guanine deaminase, 8-oxoguanine deaminase, 5'-deoxyadenosine deaminase, uracil phosphoribosyltransferase, thymidine kinase, penicillin amidase, alkaline phosphatase, alcohol dehydrogenase, β-lactamase, β-glucoronidase, carboxyesterases, carboxypeptidase A, carboxypeptidase G2, glycosidases and nitroreductase.

In one embodiment, the targeted prodrug enzyme fusion carrier further comprises a marker molecule, wherein the marker molecule is selected from, for example, but not limited to, a radionuclide, indium-111 ($^{111}$In), gallium-67, gallium-68, yttrium-90, lutetium-177, and a fluorescent protein. The metal chelating agent is selected from, for example, but not limited to, DTPA, NOTA and DOTA. The molar ratio of the prodrug enzyme and the metal chelating agent is less than 20%.

Moreover, the targeted prodrug enzyme fusion protein for example, but not limited to, RGD4C-yCD (SEQ ID NO: 3), RGD4C_yCD_yUPRT (SEQ ID NO: 4), RGD_EGF_yCD (SEQ ID NO: 5), RGD_EGF_yCD_yUPRT (SEQ ID NO: 6), RGD4C_EGF_yCD (SEQ ID NO: 7), RGD4C_EGF_yCD_yUPRT (SEQ ID NO: 8), yCD_RGD_EGF (SEQ ID NO: 9), yCD_yUPRT_RGD_EGF (SEQ ID NO: 10), yCD_RGD4C_EGF (SEQ ID NO: 11), yCD_yUPRT_RGD4C_EGF (SEQ ID NO: 12), RGD_VEGF_yCD (SEQ ID NO: 13), RGD_VEGF_yCD_yUPRT (SEQ ID NO: 14), RGD4C_VEGF_yCD (SEQ ID NO: 15), RGD4C_VEGF_yCD_yUPRT (SEQ ID NO: 16), RGD4C_EcCD_WT (SEQ ID NO: 19), RGD4C_EcCD_D314A (SEQ ID NO: 20), RGD_EGF_EcCD_WT (SEQ ID NO: 21), RGD_EGF_EcCD_D314A (SEQ ID NO: 22), RGD4C_EGF_EcCD_WT (SEQ ID NO: 23), RGD4C_EGF_EcCD_D314A (SEQ ID NO: 24), EcCD_WT_RGD_EGF (SEQ ID NO: 25), EcCD_D314A_RGD_EGF (SEQ ID NO: 26), EcCD_WT_RGD4C_EGF (SEQ ID NO: 27), EcCD_D314A_RGD4C_EGF (SEQ ID NO: 28), RGD_VEGF_EcCD_WT (SEQ ID NO: 29), RGD_VEGF_EcCD_D314A (SEQ ID NO: 30), RGD4C_VEGF_EcCD_WT (SEQ ID NO: 31), RGD4C_VEGF_EcCD_D314A (SEQ ID NO: 32).

As mentioned above, the targeted prodrug enzyme fusion carrier of the present invention can effectively identify and bind the tumor cells, tumor-induced tumor angiogenesis and tumor microenvironment. The targeted prodrug enzyme fusion carrier also has a targeted prodrug enzyme fusion protein and a theranostic system utilizing the method of in vivo nuclear medicine for the clinical diagnosis and treatment of individual patients with tumors.

The following examples are given for the purpose of illustrating various embodiments of the invention and are not meant to limit the present invention in any fashion.

EXAMPLE

Figure 1B:
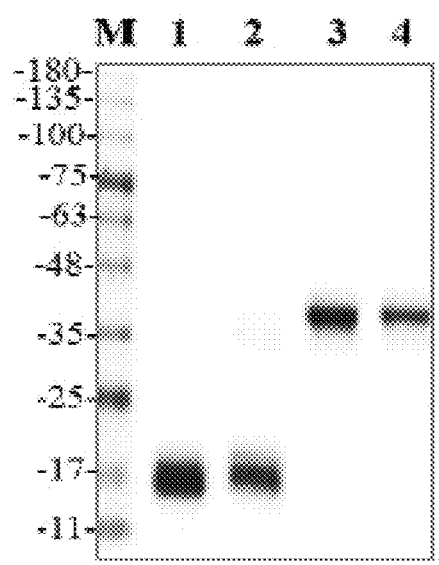
Figure 1C:
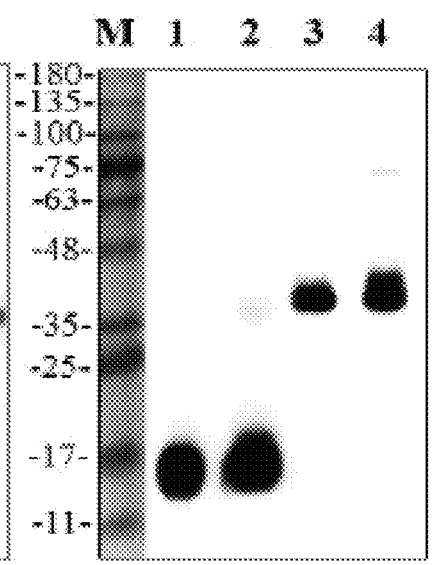

1. Preparation, purification and identification of RGD4C-yCD, yCD, RGD4C-yCD/UPRT, yCD/UPRT, RGD-VEGF-yCD, RGD4C-VEGF-yCD, RGD-EGF-yCD, RGD4C-EGF-yCD, yCD-RGD-EGF, yCD-RGD4C-EGF, RGD-VEGF-yCD/UPRT, RGD4C-VEGF-yCD/UPRT, RGD-EGF-yCD/UPRT, RGD4C-EGF-yCD/UPRT, yCD/UPRT-RGD-EGF and yCD/UPRT-RGD4C-EGF recombinant proteins. After the expression carrier construction is completed by pET28a(+) yCD, pET28a(+)-RGD4C-yCD, pET28a(+)-yCDUPRT, and pET28a(+) RGD4C-yCD/UPRT, pET28a(+)-RGD4C-VEGF-yCD, pET28a(+)-RGD-EGF-yCD, pET28a(+)-RGD4C-EGF-yCD, pET28a(+)-yCD-RGD-EGF, pET28a(+)-yCD-RGD4C-EGF, pET28a(+)-RGD-VEGF-yCD/UPRT, pET28a(+)-RGD4C-VEGF-yCD/UPRT, pET28a(+)-RGD-EGF-yCD/UPRT, pET28a(+)-RGD4C-EGF-yCD/UPRT, pET28a(+)-yCD/UPRT-RGD-EGF and pET28a(+)-yCD/UPRT-RGD4C-EGF (see FIG. 1A), the *E. coli* BL21 (DE3) strain is introduced by heat shock mode, and the protein expression is induced by IPTG. After purification, the purified protein is analyzed by SDS-PAGE and Western blot (see FIG. 1B and FIG. 1C). From the results of SDS-PAGE, it was observed that all proteins are consistent with the corresponding molecular weight, and then the protein detected by anti-His6-tag-HRP antibody is also consistent with the result of SDS-PAGE. The purified yields of yCD and RGD4C-yCD are about 56.1 mg/L and 25.6 mg/L respectively. The purified yields of yCD/UPRT and RGD4C-yCD/UPRT are about 22.0 mg/L and 21.6 mg/L respectively.

Figure 2A:
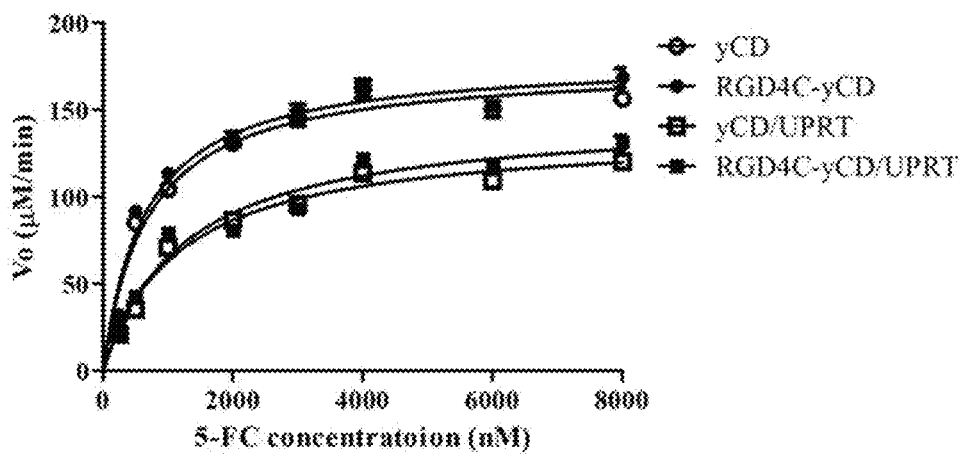
FIGS. 2A-2B show the enzyme activities of RGD4C-yCD, yCD, RGD4C-yCD/UPRT and yCD/UPRT proteins to convert 5-FC to 5-FU. 50 nM of RGD4C-yCD, yCD, RGD4C-yCD/UPRT or yCD/UPRT protein reacted with increasing concentrations of 5-FC in phosphate buffered saline solutions.
Figure 2B:
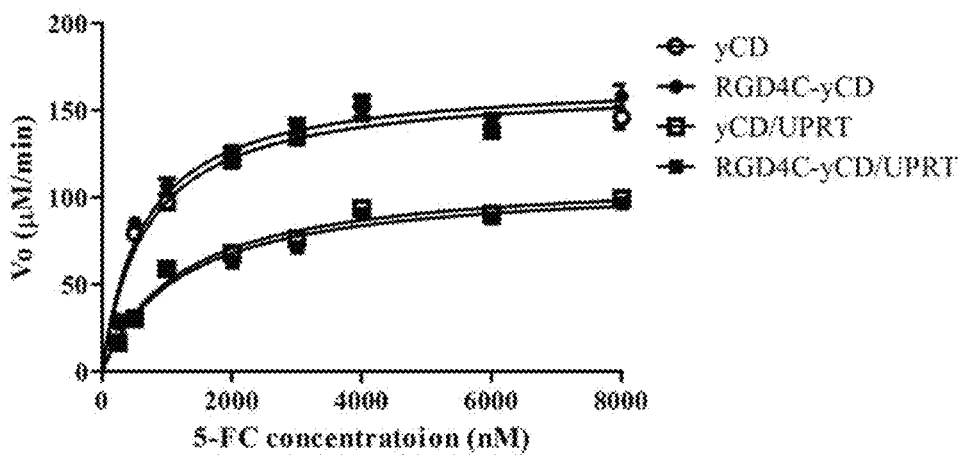

2. Enzyme Activity and Kinetic Analysis of RGD4C-yCD, yCD, RGD4C-yCD/UPRT and yCD/UPRT Recombinant Proteins The enzyme activity of 5-FC converted into 5-FU by RGD4C-yCD, yCD, RGD4C-yCD/UPRT and yCD/UPRT is performed. The recombinant protein concentration (50 nM) added with 5-FC at different concentrations. The 5-FC consumption and the generated amount of 5-FU is calculated. The measured data is taken as the x-axis by the substrate concentration [S]; the initial reaction rate $V_0$ is the kinetic curve by making a diagramthe with y-axis (see FIG. 2A and FIG. 2B); the non-linear regression is made by the prism software according to the Michaelis-Menten equation; calculate the enzyme kinetic parameter $K_m$ and $V_{max}$. Calculated by the 5-FC consumption, $K_m$ and $V_{max}$ values of yCD and RGD4C-yCD are similar, the values are 0.7±0.1 mM and 0.6±0.1 mM and 175.8±4.7 and 179.5±4.7 μM/min, respectively (see FIG. 2A). Calculated by 5-FU, the values are not significantly different from the calculated enzyme kinetic parameters of 5-FC consumption. The $K_m$ values are 1.0±0.1 mM and 0.9±0.1 mM, respectively, and $V_{max}$ was 164.2±4.7 and 167.7±4.6 μM/min respectively (see FIG. 1B); the kinetic parameters are calculated by 5-FC consumption for the yCD/UPRT and RGD4C-yCD/UPRT, the $K_m$ and $V_{max}$ of both are similar, and the values are 1.2±0.1 mM and 1.2±0.2 mM and 137.2±3.6 and 147.0±5.9 μM/min respectively; When calculated by 5-FU, the $K_m$ values are 1.2±0.1 mM and 1.2±0.2 mM respectively, similar to the parameters calculated by 5-FC consumption. $V_{max}$ values are 112.7±8.1 and 109.2±10.1 μM/min respectively, which is smaller than the $V_{max}$ calculated by 5-FC consumption. In summary, the catalytic rate of yCD/UPRT and RGD4C-yCD/UPRT for 5-FC is slightly slower than that of yCD and RGD4C-yCD, while the $K_m$ values are not significantly different from each other. It is speculated that the yCD function in each fusion protein is similar, but yUPRT may affect the effects of yCD and 5-FC. The results also show that yCD and yCD/UPRT have little effect on the activity of RGD4C short-chain peptide fusion.

Figure 3A:
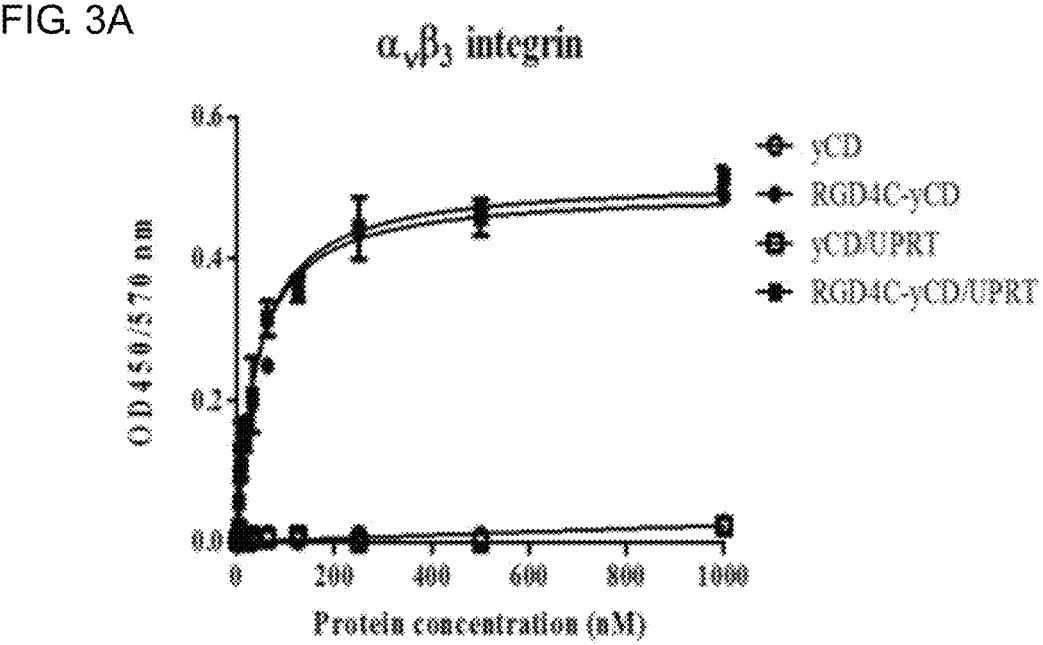
FIGS. 3A-3B show the the binding affinity and specificity of RGD4C-yCD, yCD, RGD4C-yCD/UPRT and yCD/UPRT proteins to integrin $α_vβ_3$. The binding affinities of RGD4C-yCD, yCD, RGD4C-yCD/UPRT and yCD/UPRT proteins to integrin $α_vβ_3$ were determined by ELISA assay using horseradish peroxidase (HRP)-tagged anti-His6 antibody (FIG. 3A). The dissociation constant $K_d$ is obtained by prism software with curve fitting method.
Figure 3B:
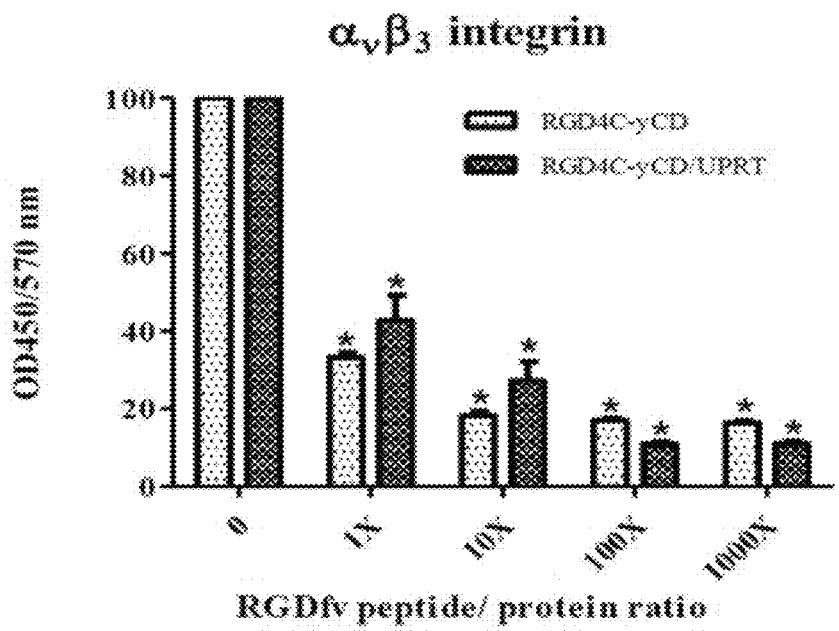

3. Binding Activity and Specificity Test of RGD4C-yCD, yCD, RGD4C-yCD/UPRT and yCD/UPRT Recombinant Protein and Integrin $\alpha_v\beta_3$ Receptor The specific binding ability of RGD4C-yCD, yCD, RGD4C-yCD/UPRT and yCD/UPRT recombinant protein to integrin αvβ3 receptor is analyzed by ELISA binding assay, plotted with prism software and made with curve fitting to find the dissociation constant $K_d$ value. The experiment results show that yCD and yCD/UPRT with circular RGD4C sequence have good binding ability to integrin $\alpha_v\beta_3$ receptor ($K_d$ is about 39.5±5.1 nM and 41.7±3.9 nM respectively) (see FIG. 3A and Table 1). The yCD and yCD/UPRT cannot be bound to integrin $\alpha_v\beta_3$ due to be not similar RGD4C as short-chain peptide. However, the RGDfv peptide at same concentration can inhibit the RGD4C-yCD and RGD4C-yCD/UPRT bound to integrin $\alpha_v\beta_3$ (decreased by 50%) (see FIG. 3B), which shows that RGD4C-yCD and RGD4C-yCD/UPRT are specifically bound with integrin $\alpha_v\beta_3$ through the RGD4C peptide sequence.

TABLE 1

The dissociation constant $K_d$ value of RGD4C-yCD, yCD, RGD4C-yCD/UPRT and yCD/UPRT recombinant protein and integrin αvβ3 receptor.

| Protein | $K_d$ |
|---|---|
| yCD | N/A |
| RGD4C-yCD | 39.5 ± 5.1 nM |
| yCD/UPRT | N/A |
| RGD4C-yCD/UPRT | 41.7 ± 3.9 nM |

Figure 4A:
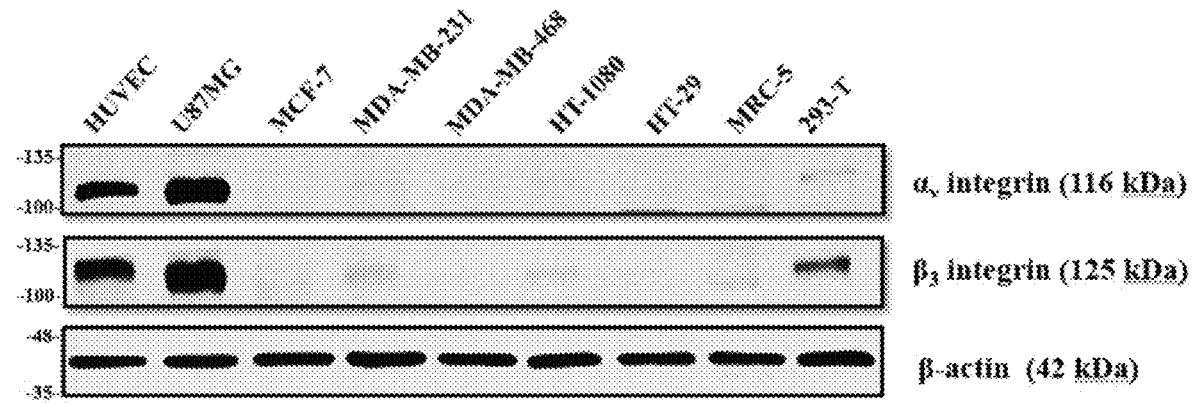
FIGS. 4A-4C shows that the expression level of integrin $α_vβ_3$ in different cell lines analyzed by western blotting method and quantified by Image J software.
Figure 4B:
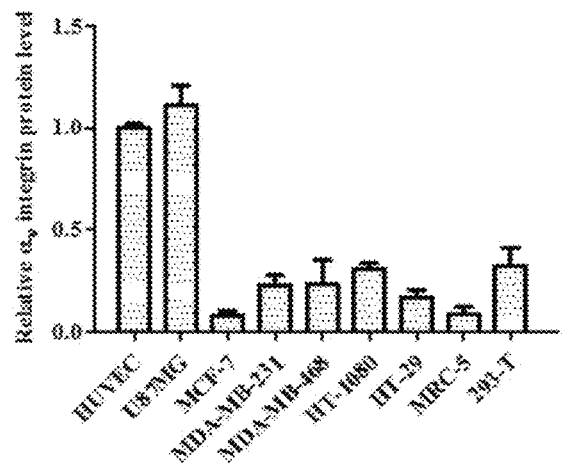
Figure 4C:
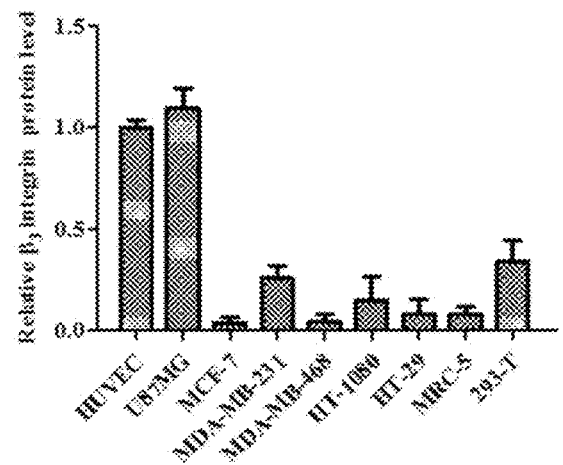

4. The Expression Amount of the Integrin $\alpha_v\beta_3$ Receptor in Different Cell Strains Analyzed by Western Blotting Method The protein lysates of each cell lines are subjected to protein electrophoresis, and then stained with anti-$\alpha_v$ and $\beta_3$ integrin antibodies and corresponding secondary fluorescent antibodies, and the expression levels of $\alpha_v$ and $\beta_3$ integrin receptors of each cell lines are analyzed by western blotting method (see FIG. 4A). The results show that the HUVEC and U87MG cells express higher $\alpha_v$ and $\beta3$ integrin than other strain cells, while MCF-7 cells almost do not express $\alpha_v$ and $\beta_3$ integrin. FIG. 4B and FIG. 4C show that the results of ROI selected and quantified by Image J image analysis software. Normalization is performed through β-actin (internal control) quantitative values divided by the $\alpha_v$ and $\beta_3$ integrin quantitative values, and the ratio is defined as 1.0 after normalization is obtained by HUVEC cells. The results show that the expression amount of αv and $\beta_3$ integrin in HUVEC and U87MG cells is about 10 times higher than that in MCF-7 cells. This study selects these three cells for subsequent experiments related to RGD4C-yCD, yCD, RGD4C-yCD/UPRT and yCD/UPRT recombinant protein.

Figure 5A:
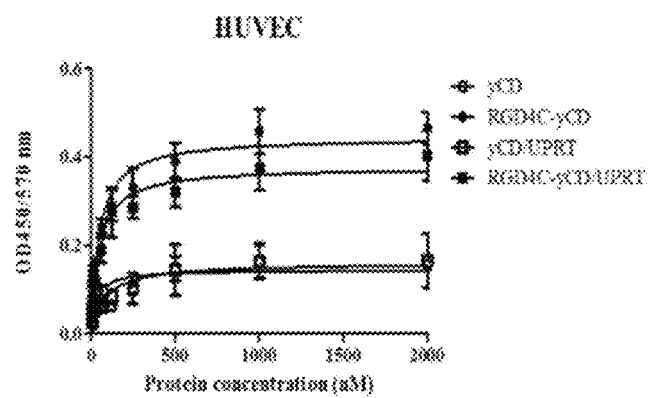
FIGS. 5A-5C shows the binding affinity of RGD4C-yCD, yCD, RGD4C-yCD/UPRT and yCD/UPRT to integrin $α_vβ_3$ in high expression and low expression cell lines.
Figure 5B:
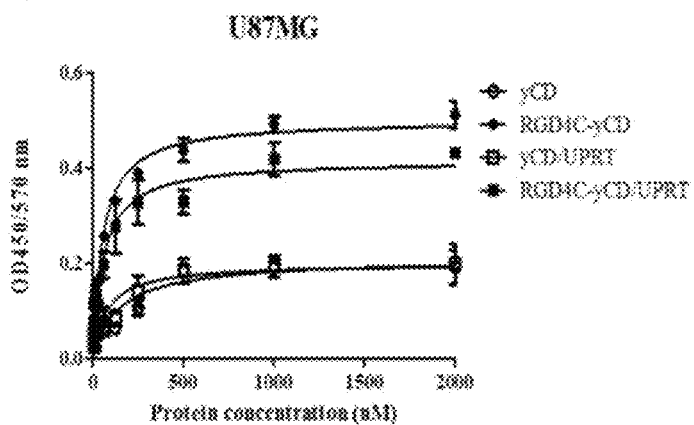
Figure 5C:
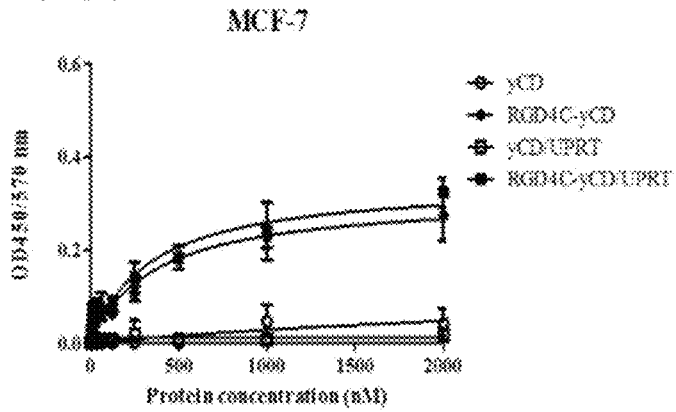
Figure 6A:
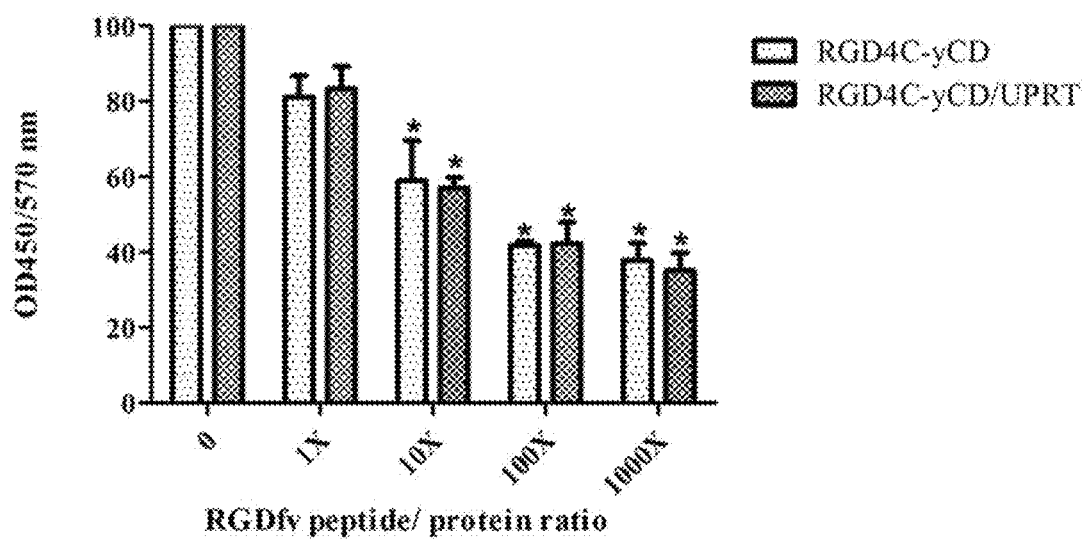
FIGS. 6A-6B show the in-vitro competitive binding assay. For observing the ability of the competing objects to inhibit the fusion protein bound with integrin $α_vβ_3$, the U87MG cells (FIG. 6A) and HUVEC cells (FIG. 6B) were incubated with RGD4C-yCD, yCD, RGD4C-yCD/UPRT and yCD/UPRT and then added competing objects (RGDfv peptide) with different concentrations. The RGDfv peptide competing objects with 10-fold relative concentration can inhibit the RGD4C-yCD and RGD4C-yCD/UPRT bound with integrin $α_vβ_3$ (approximately 50% reduction), (*compared with untreated RGDfv group, P<0.05).
Figure 6B:
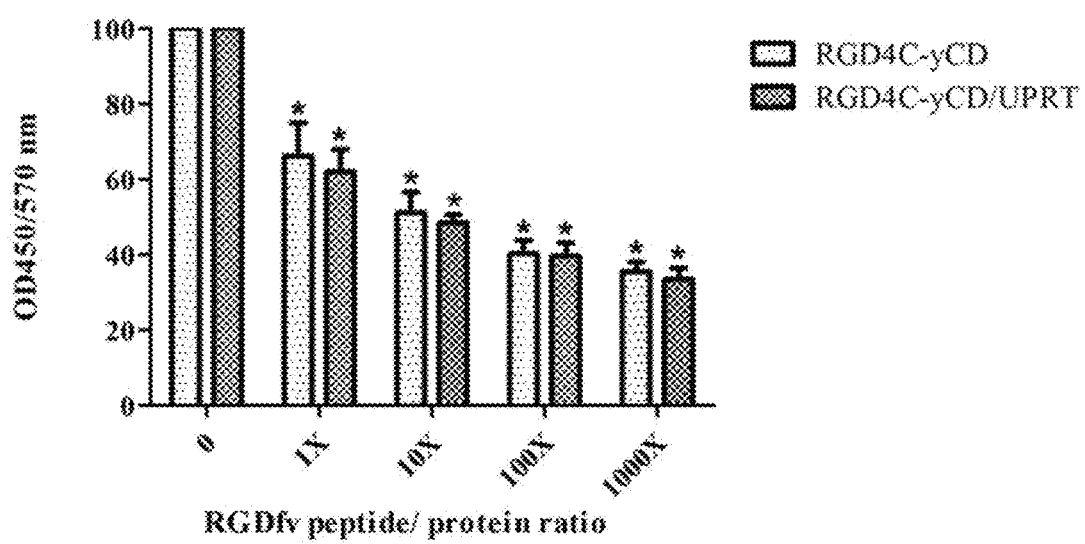

5. Specific Binding Assay of RGD4C-yCD, yCD, RGD4C-yCD/UPRT and yCD/UPRT Recombinant Protein and Cell As demonstrated above, the three cell strains are respectively seeded in a 96-well plate for 24 hours, while comparison of different protein concentration of RGD4C-yCD, yCD, RGD4C-yCD/UPRT and yCD/UPRT is added and co-cultured with the cells for binding assay. The anti-His6-Tag-HRP antibody and TMB show the color reagent to detect the amount of recombinant protein bound to the cell, then the dissociation constant $K_d$ value of the recombinant protein and the integrin $\alpha_v\beta_3$ receptor is calculated and a binding curve is drawn. The results show (see FIG. 5 and Table 2) that yCD and yCD/UPRT only show weak binding to the three cells. The RGD4C-yCD and RGD4C-yCD/UPRT are able to bind with highly expressing the integrin $\alpha_v\beta_3$ receptor of HUVEC (dissociation constant $K_d$ is 47.5±7.4 nM and 48.3±9.8 nM respectively) and U87MG tumor cells (dissociation constant $K_d$ is 53.7±5.6 nM and 57.8±10.5 nM respectively). However, MCF-7 tumor cells with low integrin αvβ3 receptor expression have no obvious binding ability (dissociation constants $K_d$ is 365.9±104.1 nM and 335.1±93.2 nM respectively) with RGD4C-yCD and RGD4C-yCD/UPRT. The cell binding ability of RGD4C-yCD for HUVEC and U87MG are about 7.7 folds and 6.8 folds higher than MCF-7 respectively. The cell binding ability of RGD4C-yCD/UPRT for HUVEC and U87MG are about 6.9 folds and 5.8 folds higher than MCF-7 respectively. Competition with RGDfv peptide at 10-fold relative concentration can inhibit RGD4C-yCD and RGD4C-yCD/UPRT can be bound with integrin $\alpha_v\beta_3$ (approximately decreased by 50%) (see FIG. 6). It is shown that RGD4C-yCD and RGD4C-yCD/UPRT are specially bound with integrin $\alpha_v\beta_3$ through RGD4C sequence.

TABLE 2

Dissociation constant $K_d$ values of RGD4C-yCD and RGD4C-yCD/UPRT and integrin $\alpha_v\beta_3$ receptor.

| | Protein ($K_d$) | |
|---|---|---|
| | RGD4C-yCD | RGD4C-yCD/UPRT |
| HUVEC vascular cell | 47.5 ± 7.4 nM | 48.3 ± 9.8 nM |
| U87MG tumor cell | 53.7 ± 5.6 nM | 57.8 ± 10.5 nM |
| MCF-7 tumor cell | 365.9 ± 104.1 nM | 335.1 ± 93.2 nM |

Figure 7A:
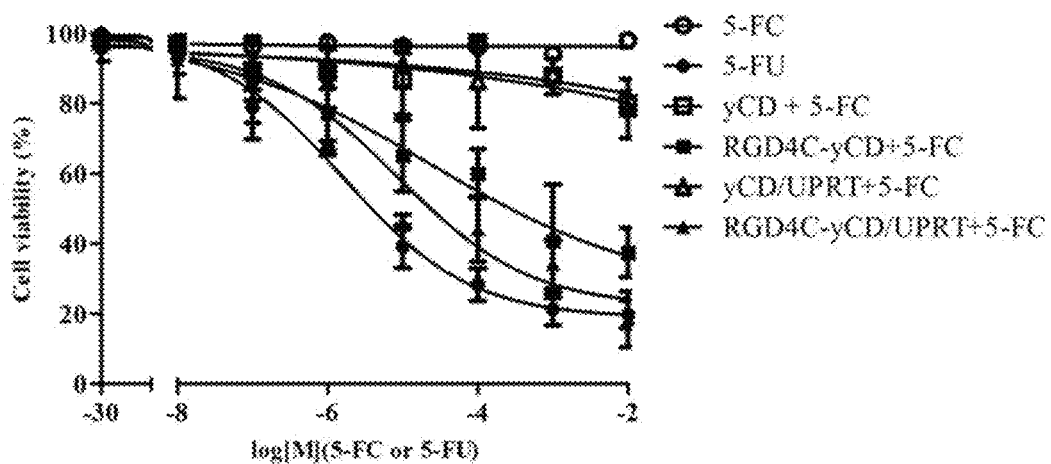
FIGS. 7A-7C shows that RGD4C-yCD/5-FC and RGD4C-yCD/UPRT/5-FC combination treatment significantly reduces cell viability of high-integrin $α_vβ_3$-expressing cells. The cell viability was determined by MTT assay. The seeded HUVEC cells shown in FIG. 7A, the seeded U87MG cells shown in FIG. 7B and the 96 wells of seeded MCF-7 cells shown in FIG. 7C are respectively added with 500 nM RGD4C-yCD, yCD, RGD4C-yCD/UPRT and yCD/UPRT recombinant protein, after removing the recombinant protein not bound with the cells and washing the cells, add 5-FC with different concentrations and observe the cell killing effect. Cells of the control groups were only incubated with different concentrations of 5-FU or 5-FC without protein treatment.
Figure 7B:
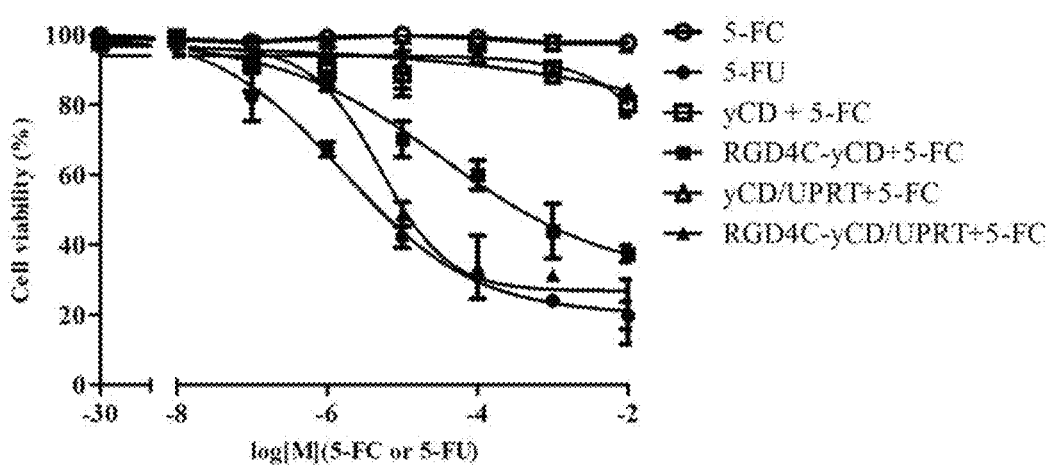
Figure 7C:
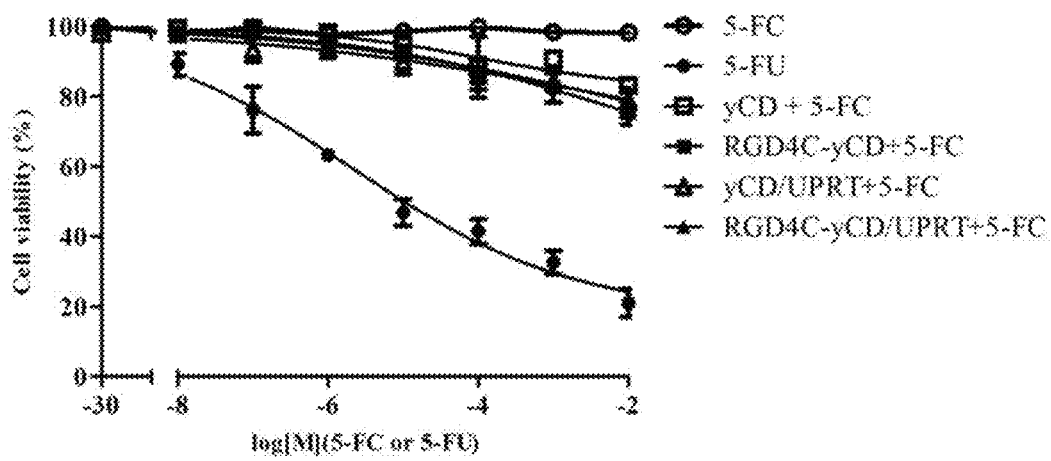

6. Cytotoxicity Assay of RGD4C-yCD, yCD, RGD4C-yCD/UPRT and yCD/UPRT Combined with 5-FC In this experiment, the MTT assay is applied to measure cytotoxicity induced by RGD4C-yCD/5-FC and RGD4C-yCD/UPRT/5-FC of the targeted prodrug enzyme fusion protein. In 96-well plate of seeded cells is respectively added with recombinant proteins such as 500 nM RGD4C-yCD, yCD, RGD4C-yCD/UPRT and yCD/UPRT, and co-cultured at 37° C. for 2 hours. The recombinant proteins not bound with cells are discarded. The cells were washed, and then were treated with different concentrations of 5-FC for observing the effect of cytotoxicity. On the other hand, the cells only treated with different concentrations of 5-FC and 5-FU separately as the control group. The experimental results show that the significant cytotoxic ability to HUVEC, U87MG and MCF-7 cells are treated with 5-FU ($IC_{50}$: 1.6±0.2 μM, 1.6±0.3 μM and 2.1±0.3 μM, respectively). There is not significant cytotoxic ability to HUVEC, U87MG and MCF-7 cells treated with 5-FC (shown in FIG. 7 and Table 3). Also, there is not significant cytotoxic ability to HUVEC, U87MG and MCF-7 cells treated with yCD coupled with 5-FC or yCD/UPRT coupled with 5-FC (the survival rate is higher than 80%, see FIG. 7). In other word, the results of yCD or yCD/UPRT respectly coupled with 5-FC are similar to the group treated with 5-FC. The cytotoxic effect of RGD4C-yCD coupled with 5-FC treatment to HUVEC and U87MG cells is significantly better than that of MCF-7 cells with low expression of integrin $\alpha_v\beta_3$ ($IC_{50}$ of the three group is 23.6±3.5, 37.1±15.4 and 5130.7±1002.4 μM, respectively). The cytotoxic effect of the group of RGD4C-yCD/UPRT with 5-FC treatment to HUVEC and U87MG cells ($IC_{50}$ is 8.6±1.5 and 5.1±1.3 μM, respectively) is better than that of RGD4C-yCD with 5-FC treatment, which shows that yUPRT can improve the cytotoxic ability by accelerating the efficiency of converting 5-FU to 5-FUMP (see FIG. 7A and FIG. 7B). There is not significant cytotoxic ability of MCF-7 cells with low expression of integrin $\alpha_v\beta_3$ treated by RGD4C-yCD/UPRT coupled with 5-FC ($IC_{50}$ is 4341.3±1120.9 μM). This result suggests that there is a specific cytotoxic ability of cells with high expression of integrin $\alpha_v\beta_3$ treated by RGD4C-yCD coupled with 5-FC or RGD4C-yCD/UPRT coupled with 5-FC. However, the cytotoxic effect of RGD4C-yCD coupled with 5-FC or RGD4C-yCD/UPRT coupled with 5-FC are not as good as 5-FU. Conversely, there is more cell selectivity than 5-FU. The results also confirm that 5-FC is not highly toxic to cells, so 5-FC is suitable for using with a targeted prodrug enzyme fusion protein applied to a theranostic system.

TABLE 3

Cytotoxic ability test of RGD4C-yCD plus 5-FC treatment, RGD4C-yCD/UPRT plus 5-FC treatment and 5-FU treatment to HUVEC, U87MG and MCF-7 cells respecyly.

| | Protein (500 nM) with 5-FC or 5-FU($IC_{50}$) | | |
|---|---|---|---|
| | RGD4C-yCD + 5-FC | RGD4C-yCD/UPRT + 5-FC | 5-FU |
| Vascular cell HUVEC | 23.6 ± 3.5 μM | 8.6 ± 1.5 μM | 1.6 ± 0.2 μM |
| U87MG tumor cell | 37.1 ± 15.4 μM | 5.1 ± 1.3 μM | 1.6 ± 0.3 μM |
| MCF-7 tumor cell | 5130.7 ± 1002.4 μM | 4341.3 ± 1120.9 μM | 2.2 ± 0.3 μM |

Figure 8A:
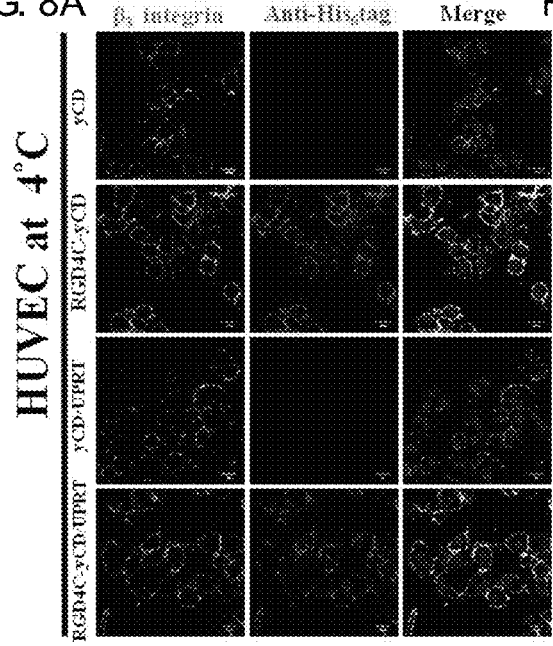
Figure 8B:
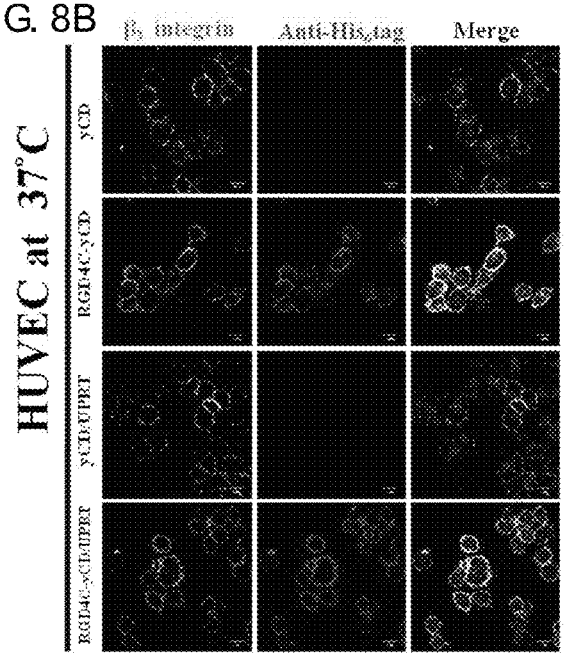
Figure 8C:
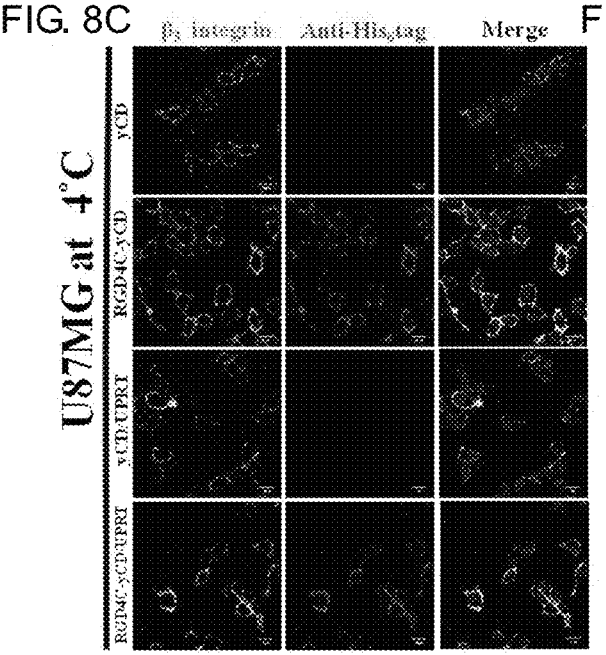
Figure 8D:
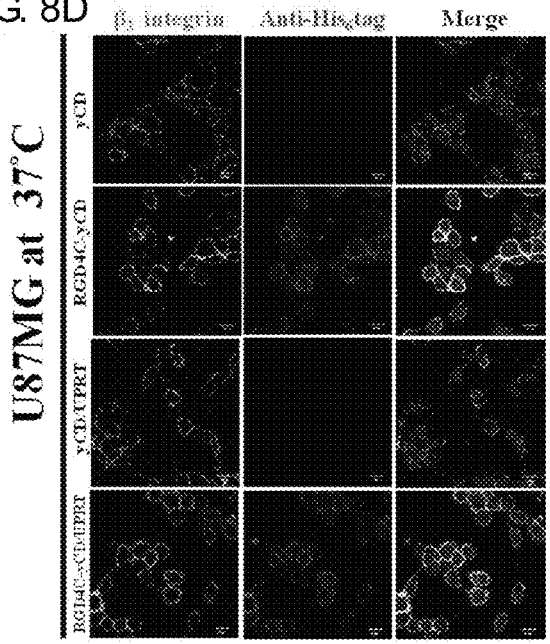

7. Binding and Distribution of RGD4C-yCD, yCD, RGD4C-yCD/UPRT and yCD/UPRT Fusion Proteins with HUVEC and U87MG Cells HUVEC and U87MG cells are co-cultured with culture medium containing 500 nM RGD4C-yCD and RGD4C- yCD/UPRT protein at 4° C. and 37° C. for 2 hours, then the cells are stained with fluorescence, and the distribution in the cell is observed by conjugated fluorescence microscopy. RGD4C-yCD and RGD4C-yCD/UPRT will be only bound to HUVEC and U87MG cell surface (red fluorescence) at 4° C., and at colocalization with $\beta_3$ integrin (green fluorescence) (see FIG. 8A and FIG. 8C), it is shown that both proteins can be adhered on the cell membrane through specific binding with integrin, and the weak fluorescence signals can only be detected due to that yCD and yCD/UPRT can not be effectively bound with HUVEC and U87MG cells. Under co-culturing conditions at 37° C., RGD4C-yCD and RGD4C-yCD/UPRPT can enter the inside of HUVEC and U87MG cells through endocytosis (see FIG. 8B and FIG. 8D). The study results show that RGD4C-yCD and RGD4C-yCD/UPRPT can enter the cell by binding with integrin $\alpha_v\beta_3$.

Figure 9A:
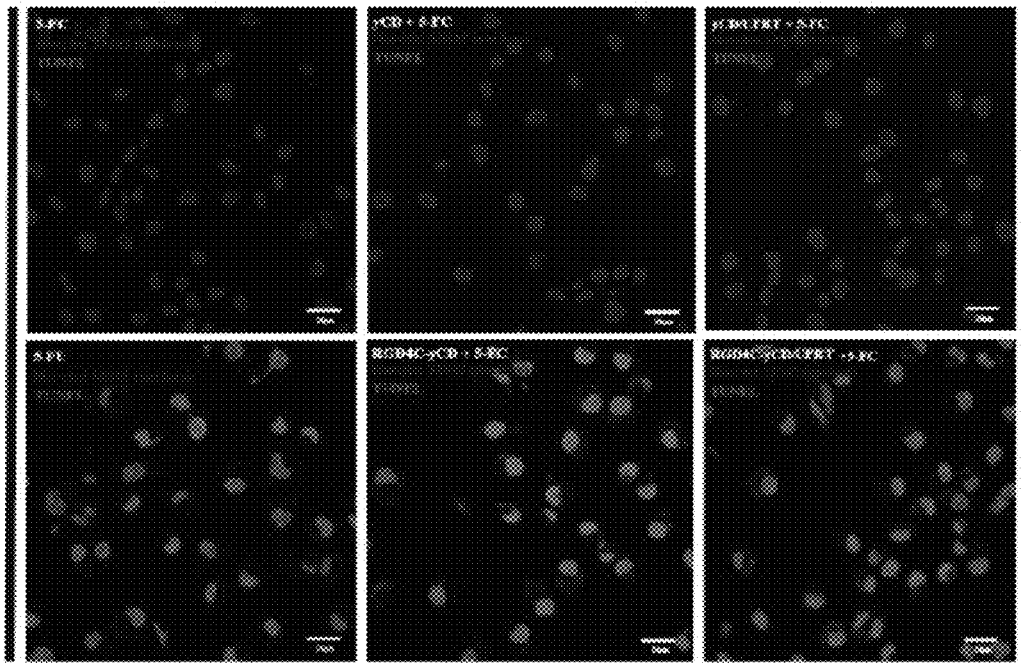
Figure 9B:
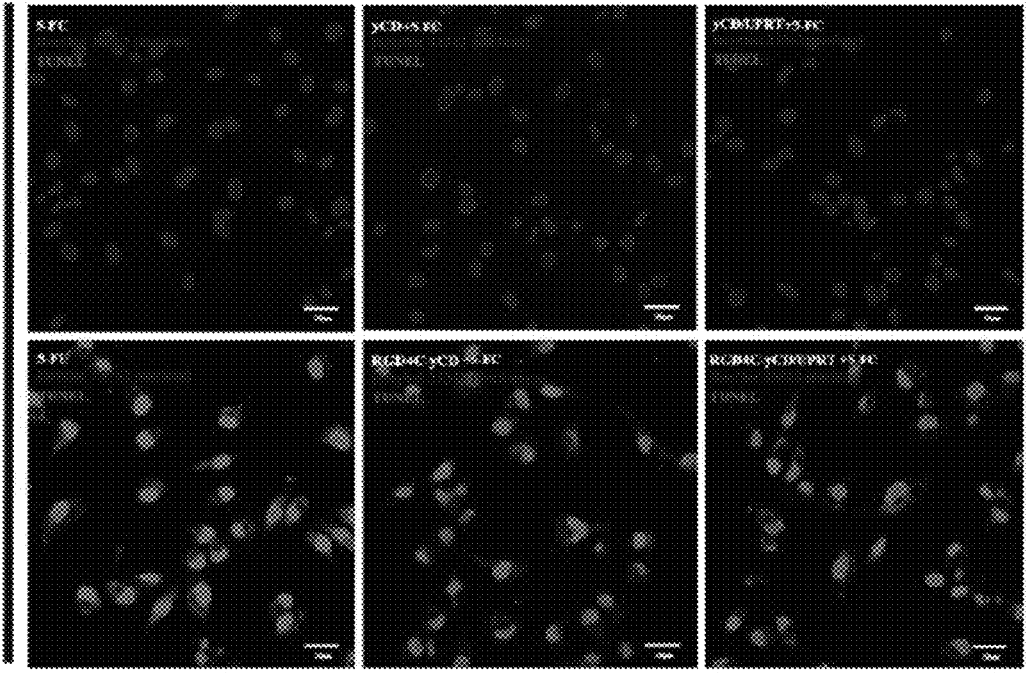
Figure 9C:
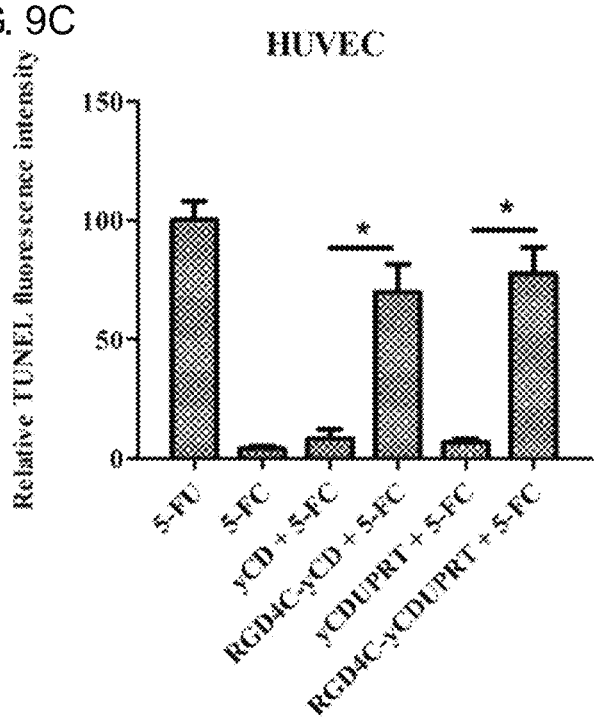
Figure 9D:
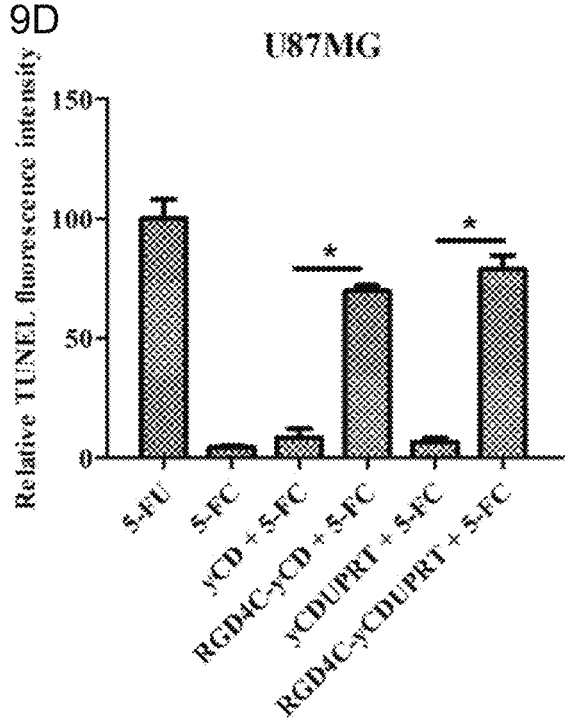

8. Analysis of Apoptosis Induced by RGD4C-yCD/5-FC and RGD4C-yCD/UPRT/5-FC Targeted Prodrug Enzyme Fusion Protein of Theranostic System Previous literature pointed out that 5-FU can promote apoptosis by inhibiting the synthesis of cellular DNA. This experiment is performed on apoptosis analysis to evaluate whether the enzyme precursor treatment system of RGD4C-yCD/5-FC and RGD4C-yCD/UPRT/5-FC can kill the cells by apoptotic mechanism. HUVEC and U87MG cells are co-cultured with culture medium containing 500 nM RGD4C-yCD and RGD4C-yCD/UPRT protein for 2 hours at 37° C., remove and wash the unbound or endocytic proteins, add 100 μM 5-FC or 5-FU, after acting for 72 hours, the DNA fragment of the apoptosis is stained with fluorescence by TUNEL assay analysis set, and the apoptosis is observed by conjugated fluorescence microscope. The results show that the groups treated with 5-FU, RGD4C-yCD/5-FC and RGD4C-yCD/UPRT/5-FC will cause a large amount of apoptosis in HUVEC and U87MG cells (see FIG. 9A and FIG. 9C, the red fluorescence position indicates the DNA fragments produced by apoptosis, and its signal mainly exists in the nucleus). Furthery, TUNEL fluorescence signals are quantified by image analysis software MetaMorph. The degree of apoptosis induced by the groups treated with RGD4C-yCD/5-FC and RGD4C-yCD/UPRT/5-FC respectly are significantly higher than that of the yCD/5-FC and yCD/UPRT/5-FC treatment group (*P<0.05) (see FIG. 9B and FIG. 9D). Moreover, the tendency of apoptosis for treated with RGD4C-yCD/UPRT/5-FC treatment is higher than that of RGD4C-yCD/5-FC (but no statistically significant difference). The results show that RGD4C-yCD/5-FC and RGD4C-yCD/UPRT/5-FC targeted prodrug enzyme fusion protein of theranostic system can induce death of the cells through apoptosis pathway.

Figure 10A:
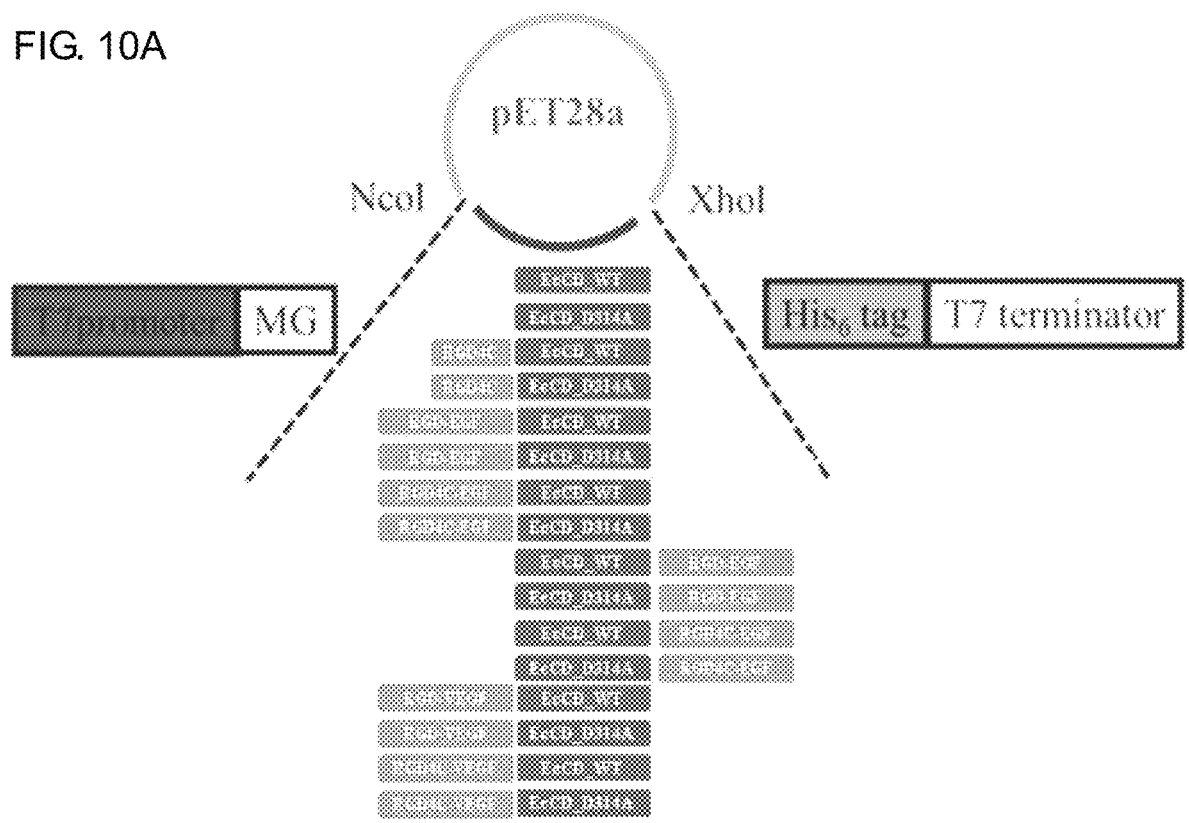
Figure 10B:
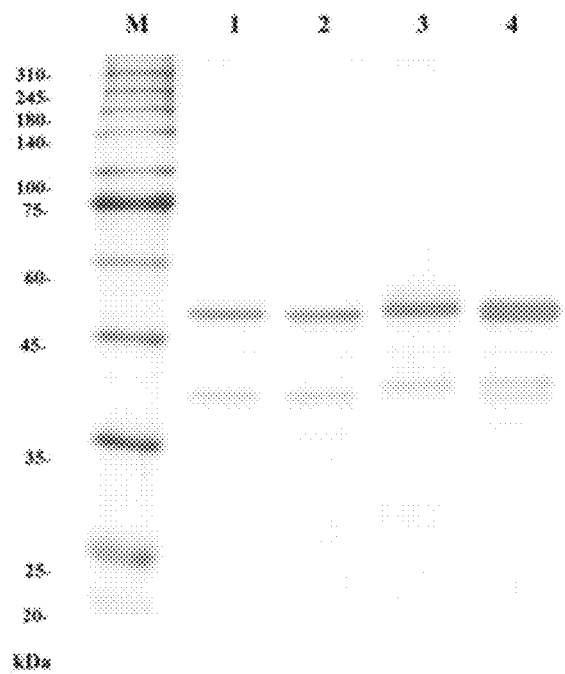
Figure 10C:
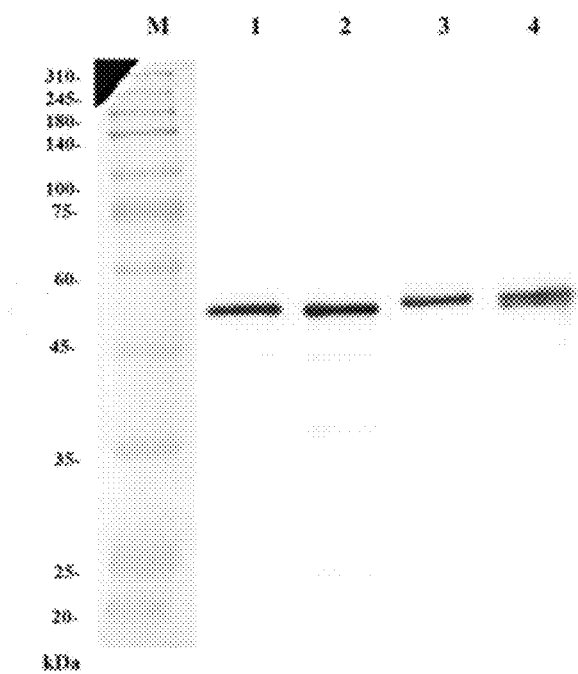

9. EcCD series fusion protein (EcCD_WT, RGD4C-EcCD_WT, EcCD_D314A, RGD4C-EcCD_D314A, RGD-VEGF-EcCD_WT, RGD4C-VEGF-EcCD_WT, RGD-EGF-EcCD_WT, RGD4C-EGF-EcCD_WT, EcCD_WT-RGD-EGF, EcCD_WT-RGD4C-EGF, RGD-VEGF-EcCD_D314A, RGD4C-VEGF-EcCD_D314A, EcCD_D314A-RGD-EGF, EcCD_D314A-RGD4C-EGF, RGD-EGF-EcCD_D314A and RGD4C-EGF-EcCD_D314A) design, expression and purification After the carrier construction is completed by pET28a(+)-EcCD_WT, pET28a(+)-RGD4C-EcCD_WT, pET28a(+)-EcCD_D314A, pET28a(+)-RGD4C-EcCD_D314A, pET28a(+)-RGD-VEGF-EcCD_WT, pET28a(+)-RGD4C-VEGF-EcCD_WT, pET28a(+)-RGD-EGF-EcCD_WT, pET28a(+)-RGD4C-EGF-EcCD_WT, pET28a(+)-EcCD_WT-RGD-EGF, pET28a(+)-EcCD_WT-RGD4C-EGF, pET28a(+)-RGD-VEGF-EcCD_D314A, pET28a(+)-RGD4C-VEGF-EcCD_D314A, pET28a(+)-RGD-EGF-EcCD_D314A, pET28a(+)-RGD4C-EGF-EcCD_D314A, pET28a(+)-EcCD_D314A-RGD-EGF and pET28a(+)-EcCD_D314A-RGD4C-EGF expression (see FIG. 10A), the E. coli RG2 (DE3) strains are fed by the heat shock, the protein expression is induced by IPTG. After purification, the purified protein is analyzed by SDS-PAGE and Western blot (see FIG. 10B and FIG. 10C). It can be observed from the SDS-PAGE results that all proteins meet the corresponding size positions. Then, the protein detected by anti-His6tag-HRP mab also meets the size position of the SDS-PAGE result.

10. Enzyme Kinetic Analysis of EcCD Series Fusion Proteins

Figure 11A:
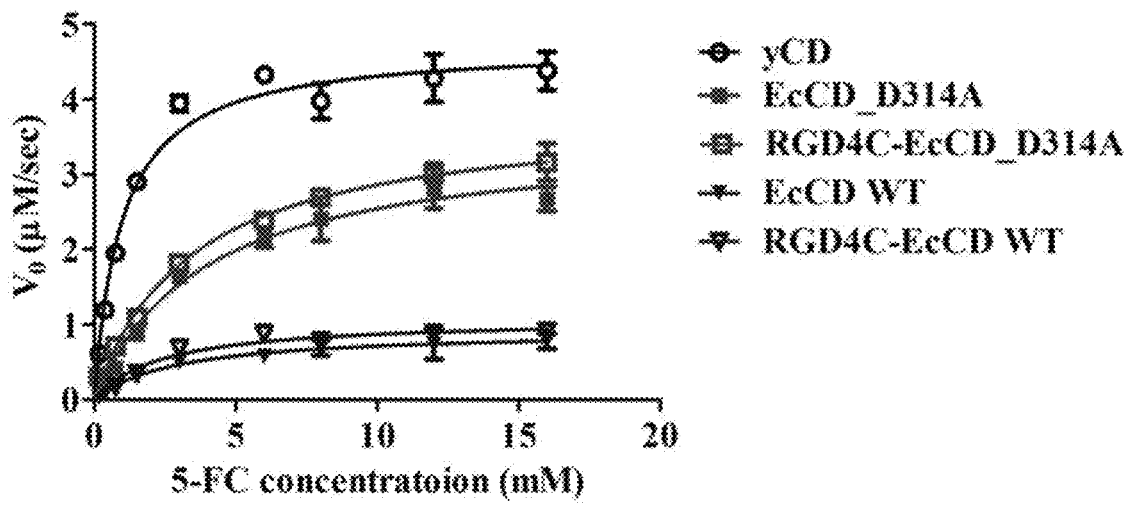
FIGS. 11A-11D show the activity and kinetics analysis of EcCD series fusion protein enzymes, and the EcCD series proteins are combined with 5-FC at different concentrations for reaction. Respectively calculate the 5-FU formation reaction rate shown in FIG. 11A, 5-FC consumption reaction rate shown in FIG. 10B, uracil formation reaction rate shown in FIG. 10C and cytosine consumption reaction rate shown in FIG. 10D, substitute Michaelis-Menten formula, and calculate the base mass ($K_{cat}$) and $K_m$ value catalyzed by each mol enzyme in unit time.
Figure 11B:
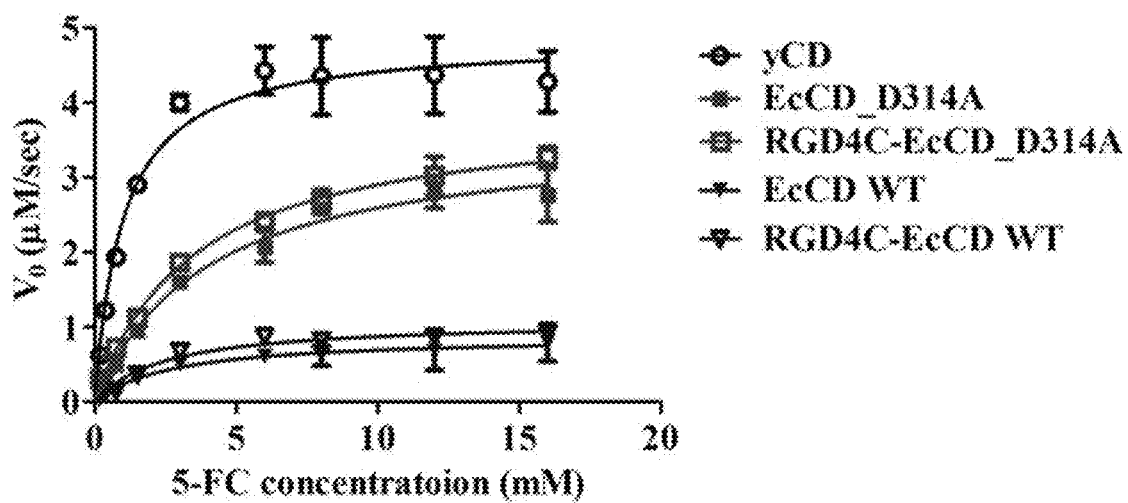

The EcCD series fusion protein is identified by purification and liquid chromatography mass spectrometry (LC/MS/MS) to confirm the correct protein, and the enzyme activity of cytosine deaminase is determined, that is, the ability that the protein converts the matrix (5-FC, cytosine) into (5-FU, uracil). The reaction rate of 5-FU generation and 5-FC consumption at different substrate concentrations are separately detected (see FIG. 11A, FIG. 11B, Table 4 and Table 5), and it can be found in the part detected by 5-FU generation that the $K_m$, $K_{cat}$ and $K_{cat}/K_m$ values of EcCD_WT are similar to that of RGD4C-EcCD_WT. The $K_m$ is 2.9±0.8 mM and 2.3±0.5 mM respectively, the $K_{cat}$ is 8.8±0.9 sec$^{-1}$ and 10.8±0.6 sec$^{-1}$ respectively, $K_{cat}/K_m$ is 3.0 and 4.7 respectively, the part of 5-FC consumption by detection is not much different from the result generated by 5-FU. $K_m$ is 2.8±0.7 mM and 2.3±0.4 mM respectively, $K_{cat}$ is 9.2±0.8 sec$^{-1}$ and 10.7±0.5 sec$^{-1}$ respectively, $K_{cat}/K_m$ is 3.3 and 4.7 respectively. And the $K_m$, $K_{cat}$ and $K_{cat}/K_m$ values of EcCD_D314A and RGD4C-EcCD_D314A in the 5-FU generation part by detection are also similar. $K_m$ is 3.9±0.6 mM and 3.5±0.3 mM respectively, $K_{cat}$ is 36.2±1.8 sec$^{-1}$ and 39.4±1.1 sec$^{-1}$ respectively, $K_{cat}/K_m$ is 9.3 and 11.3 respectively, the part of 5-FC consumption by detection is not much different from the result generated by 5-FU. $K_m$ is 3.8±0.6 mM and 3.5±0.2 mM respectively, $K_{cat}$ is 35.1±1.7 sec$^{-1}$ and 38.6±1.0 sec$^{-1}$ respectively, $K_{cat}/K_m$ is 9.2 and 11.0 respectively. The $K_{cat}/K_m$ of EcCD_D314A is about 3.1 times higher than that of EcCD_WT. The $K_{cat}/K_m$ of RGD4C-EcCD_D314A is about 2.4 times higher than that of RGD4C-EcCD_WT, which increase the activity of 5-FC.

TABLE 4

The generation reaction rate of 5-FU calculated by EcCD series proteins with 5-FC at different concentrations

| Protein | $K_m$ (mM) | $K_{cat}$ (sec$^{-1}$) | $K_{cat}/K_m$ (sec$^{-1}$ mM$^{-1}$) |
| --- | --- | --- | --- |
| yCD | 1.0 ± 0.1 | 47.2 ± 0.9 | 47.2 |
| EcCD_D314A | 3.9 ± 1.5 | 35.4 ± 0.8 | 9.1 |
| RGD4C-EcCD_D314A | 3.4 ± 0.8 | 38.4 ± 0.8 | 11.3 |
| EcCD_WT | 2.9 ± 0.6 | 9.2 ± 0.6 | 3.2 |
| RGD4C-EcCDWT | 2.4 ± 0.5 | 10.8 ± 0.5 | 4.5 |

TABLE 5

The consumption reaction rate of 5-FU calculated by EcCD series proteins with 5-FC at different concentrations

| Protein | $K_m$ (mM) | $K_{cat}$ (sec$^{-1}$) | $K_{cat}/K_m$ (sec$^{-1}$ mM$^{-1}$) |
| --- | --- | --- | --- |
| yCD | 1.0 ± 0.1 | 48.5 ± 1.3 | 48.5 |
| EcCD_D314A | 4.0 ± 10.5 | 36.2 ± 1.5 | 9.1 |
| RGD4C-EcCD_D314A | 3.5 ± 0.3 | 39.1 ± 1.0 | 11.2 |
| EcCD_WT | 2.7 ± 0.9 | 8.8 ± 0.8 | 3.3 |
| RGD4C-EcCDWT | 2.4 ± 0.4 | 10.9 ± 0.5 | 4.5 |

Figure 11C:
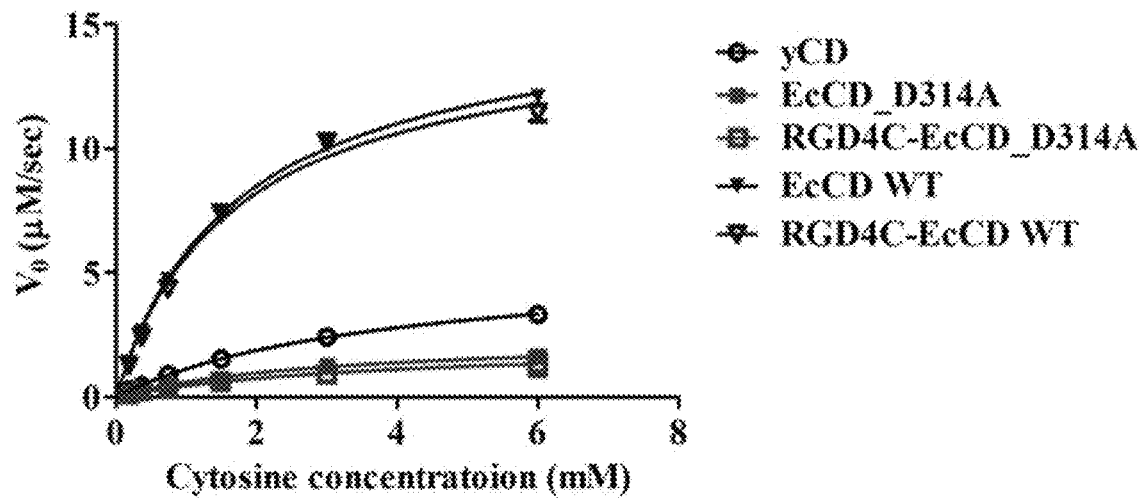
Figure 11D:
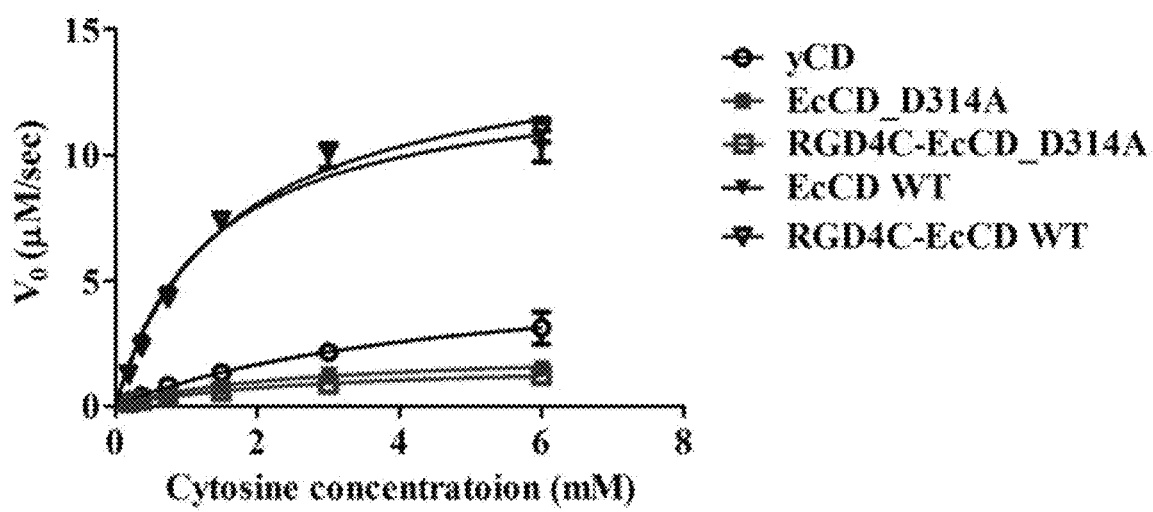

The reaction rate of uracil generation and cytosine consumption at different substrate concentrations is separately detected (see FIG. 11C, FIG. 11D, Table 6 and Table 7), and it can be found in the part detected by uracil generation that the $K_m$, $K_{cat}$ and $K_{cat}/K_m$ values of EcCD_WT are similar to that of RGD4C-EcCD_WT. $K_m$ is 1.6±0.1 mM and 1.5±0.2 mM respectively, $K_{cat}$ is 147.4±3.4 sec$^{-1}$ and 141.7±5.5 sec$^{-1}$ respectively, $K_{cat}/K_m$ is 92.1 and 94.5 respectively, the cytosine consumption part by detection is not much different from the result generated by uracil. $K_m$ is 1.7±0.1 mM and 1.7±0.2 mM respectively, $K_{cat}$ is 156.5±2.7 sec$^{-1}$ and 148.9±4.7 sec$^{-1}$ respectively, $K_{cat}/K_m$ is 92.1 and 87.6 respectively. And the $K_m$, $K_{cat}$ and $K_{cat}/K_m$ values of EcCD_D314A and RGD4C-EcCD_D314A in the uracil generation part by detection are also similar. $K_m$ is 3.0±0.4 mM and 2.9±0.6 mM respectively, $K_{cat}$ is 22.1±1.9 sec$^{-1}$ and 17.7±1.6 sec$^{-1}$ respectively, $K_{cat}/K_m$ is 7.4 and 6.1 respectively, the cytosine consumption part by detection is not much different from the result generated by uracil. $K_m$ is 2.8±0.5 mM and 3.0±0.6 mM respectively, $K_{cat}$ is 24.3±1.3 sec$^{-1}$ and 21.6±1.8 sec$^{-1}$ respectively, $K_{cat}/K_m$ is 8.7 and 7.2 respectively. The $K_{cat}/K_m$ of EcCD_D314A is about 12.5 times lower than that of EcCD_WT. The $K_{cat}/K_m$ of RGD4C-EcCD_D314A is about 15.5 times lower than that of RGD4C-EcCD_WT, which decrease the activity of cytosine and increase the selectivity to 5-FC. Evaluation of the relative substrate selectivity of cytosine deaminase enzyme for 5-FC and Cytosine can be expressed by the following formula 1, $$\frac{K_{cat}/K_m(5-FC)}{[K_{cat}/K_m(5-FC)] + [K_{cat}/K_m(\text{Cyosine})]} \quad \text{formula 1}$$

By substituting the previously measured enzyme $K_m$, $K_{cat}$ and $K_{cat}/K_m$ of 5-FC and cytosine into the above formula, you can obtain a value (see Table 8). The higher the value, the higher the selectivity of the enzyme to the 5-FC substrate. The relative substrate selectivity of EcCD_WT and RGD4C-EcCD_WT to 5-FC is similar from the results, 0.032 and 0.047 respectively are not much different from 0.027 in the literature. The relative substrate selectivity of EcCD_D314A and RGD4C-EcCD_D314A to 5-FC is also similar, 0.558 and 0.648 respectively are not much different from 0.513 in the literature. EcCD_D314A is significantly higher than EcCD_WT and the relative substrate selectivity to 5-FC is about 17.4 times. The relative substrate selectivity of RGD4C-EcCD_WT and RGD4C-EcCD_D314A is about 13.8 times significantly higher than that of 5-FC. It is confirmed by the above experiment that the EcCD series fusion protein to be produced has the enzyme activity of converting 5-FC into 5-FU, and also confirmed that RGD4C short peptide chains do not affect the enzyme activity.

TABLE 6

The generation reaction rate of uracil calculated by EcCD series protein with 5-FC at different concentrations

| Protein | $K_m$ (mM) | $K_{cat}$ (sec$^{-1}$) | $K_{cat}/K_m$ (sec$^{-1}$mM$^{-1}$) |
|---|---|---|---|
| yCD | 3.9 ± 0.2 | 54.6 ± 1.3 | 14.0 |
| EcCD_D314A | 3.1 ± 0.3 | 24.5 ± 1.1 | 7.9 |
| RGD4C-EcCD_D314A | 3.8 ± 1.7 | 21.7 ± 4.8 | 5.7 |
| EcCD_WT | 1.7 ± 0.1 | 157.3 ± 2.4 | 92.5 |
| RGD4C-EcCDWT | 1.7 ± 0.1 | 150.8 ± 4.4 | 88.7 |

TABLE 7

The consumption reaction rate of cytosine calculated by EcCD series protein with 5-FC at different concentrations

| Protein | $K_m$ (mM) | $K_{cat}$ (sec$^{-1}$) | $K_{cat}/K_m$ (sec$^{-1}$mM$^{-1}$) |
|---|---|---|---|
| yCD | 4.7 ± 1.3 | 55.6 ± 8.5 | 11.8 |
| EcCD_D314A | 2.6 ± 0.4 | 22.3 ± 1.6 | 8.6 |
| RGD4C-EcCD_D314A | 2.9 ± 0.5 | 17.7 ± 1.3 | 6.3 |
| EcCD_WT | 1.3 ± 0.1 | 132.0 ± 5.0 | 101.5 |
| RGD4C-EcCDWT | 1.6 ± 0.2 | 143.9 ± 5.1 | 89.9 |

TABLE 8

Comparing the relative substrate selectivity of enzyme to 5-FC and cytosine, the greater the value converted by formula 1, the higher the relative substrate selectivity of the enzyme to 5-FC

| Protein | $[K_{cat}/K_m(\text{5-FC})]/\{[K_{cat}/K_m(\text{cytosine})] + [K_{cat}/K_m(\text{5-FC})]\}$ |
|---|---|
| yCD | 0.771 |
| EcCD_D314A | 0.535 |
| RGD4C- EcCD_D314A | 0.664 |
| EcCDWT | 0.033 |
| RGD4C- EcCDWT | 0.048 |
| Biochemistry 2004, 43, 8957-8964EcCDWT | 0.027 |
| Biochemistry 2004, 43, 8957-8964D314A | 0.513 |

Figure 12A:
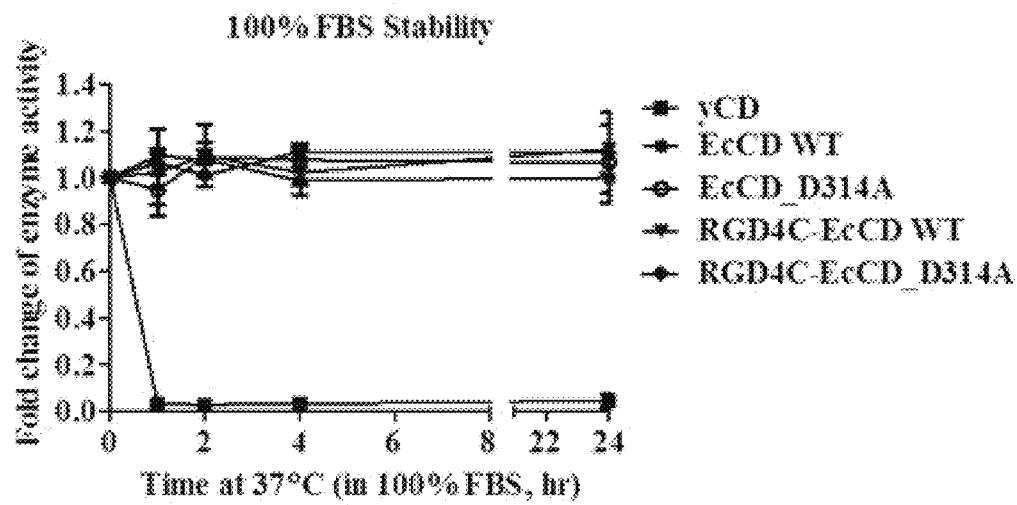
FIGS. 12A-12C show an enzyme stability analysis of EcCD series fusion protein and yCD protein.
Figure 12B:
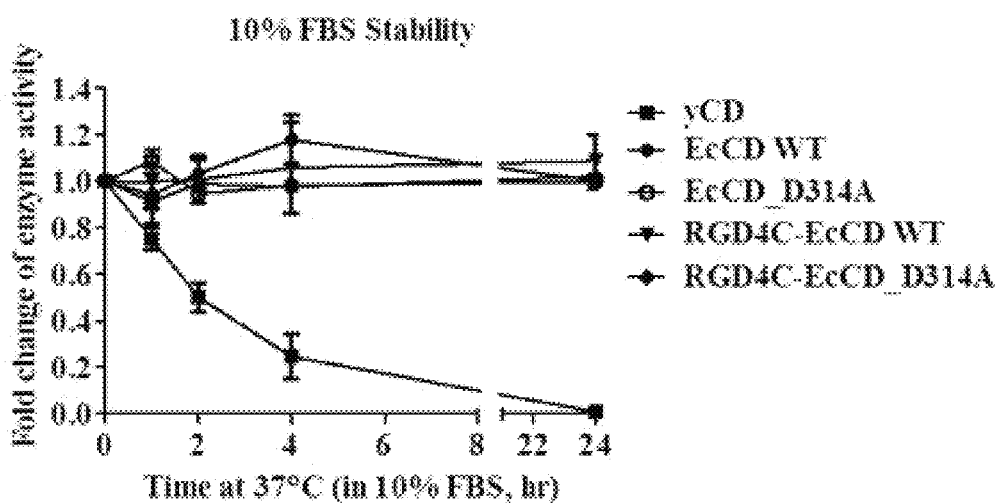
Figure 12C:
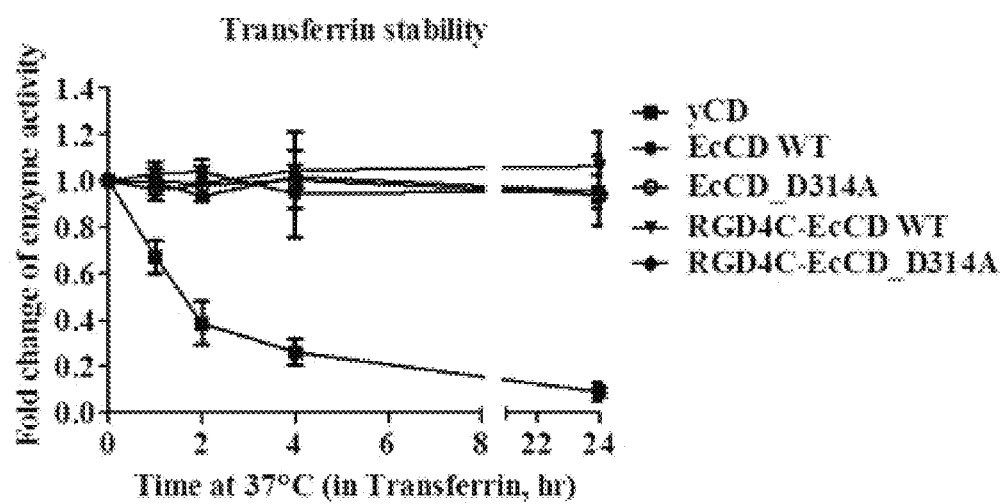

11. Comparative Analysis of Enzyme Stability Between EcCD Series Fusion Protein and yCD Protein Previous literature reports indicate that the thermostability of E. coli cytosine deaminase (EcCD) is better than that of yCD. In order to evaluate the stability of the enzymes of the EcCD series fusion protein and yCD protein expressed in this study and evaluate its stability in serum, in the experiment, EcCD_WT, EcCD_D314A, RGD4C-EcCD_WT, RGD4C-EcCD_D314A and yCD are diluted to 100% FBS (fetal bovine serum), after culturing at 37° C. for 0, 1, 2, 4, 24 hours, determine the enzyme kinetics, evaluate the enzyme stability of the EcCD series fusion protein and yCD protein by the $K_{cat}/K_m$ for showing the catalytic efficiency and specificity of the enzyme. It can be observed from the experimental results that the yCD protein is cultured in 100% FBS for 1 hour, the enzyme activity rapidly decreases to near inactivation, and the EcCD series fusion protein can maintain a relatively high enzyme activity (enzyme activity is close to 100%) (see FIG. 12A). In order to simulate the environment of the protein in the cell killing test, the EcCD series fusion protein and the yCD protein are cultured in 10% FBS at 37° C. for 0, 1, 2, 4, 24 hours, and then determine the enzyme kinetics. It can be observed from the results that the yCD protein is cultured in 10% FBS for 1 hour, the enzyme activity is reduced to 80%, and when cultured for 2 and 4 hours, the enzyme activity is reduced to 50% and 20%, respectively, and the enzyme activity is lost after culturing for 24 hours, while the EcCD series fusion protein is similar to the culture in 100% FBS, which can maintain the original enzyme activity (see FIG. 12B). The literature points out that the metal ion of the enzyme catalytic center will affect the stability of the enzyme. In the yCD protein involved in the enzyme reaction, the metal ion of the enzyme catalytic center has a considerable relationship with the enzyme activity. The protein associated with transporting metal ions in serum is transferrin. It is speculated that transferrin may be related to the enzyme activity of yCD protein. Therefore, the EcCD series fusion protein and yCD protein are co-cultured respectively with transferrin at a concentration of 3 mg/ml (normal concentration 2.1-3.4 mg/mL) at 37° C. for 0, 1, 2, 4, 24 hours, then determine the enzyme kinetics (see FIG. 12C), it is known from the results that the longer the yCD protein is cultured in the transferrin, the lower the enzyme activity will be. The enzyme activity will be close to the loss of activity after culturing for 24 hours. This trend is similar to the culture at 10% in FBS. It is speculated that the factor of reducing the activity of yCD protein in FBS has a great relationship with transferrin. The stability of yCD protein in FBS is poor, and the stability of EcCD series fusion protein is better, so the industrial use of EcCD series fusion protein in both sexual and therapeutic applications is better than that of yCD protein, and it is also confirmed that the mutation of RGD4C peptide and D314A will not affect the enzyme stability of EcCD protein.

Figure 13A:
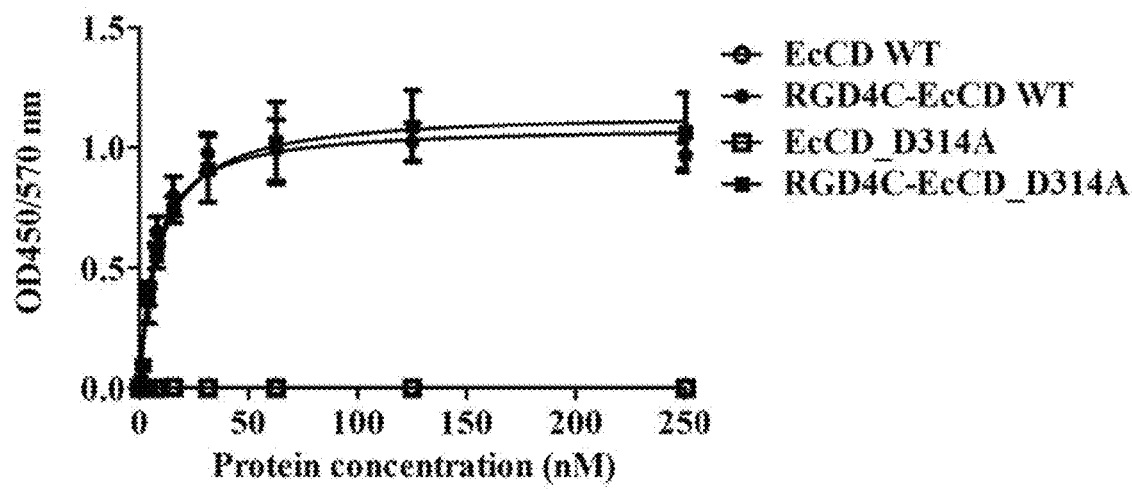
Figure 13B:
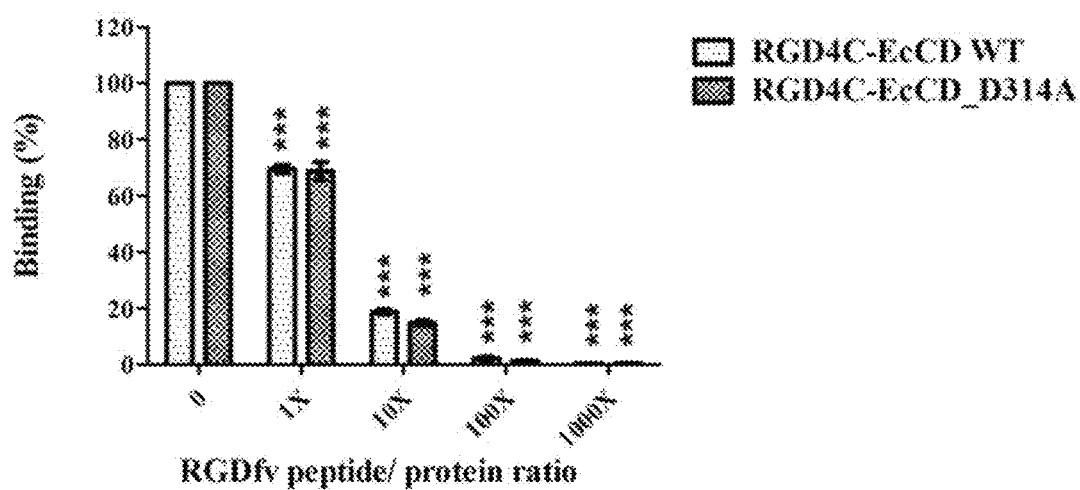

12. Binding Activity and Specificity Test of EcCD Series Fusion Protein and $\alpha_v\beta_3$ Integrin To confirm the binding ability of RGD4C peptide and $\alpha_v\beta_3$ integrin, the affinity of the protein and $\alpha_v\beta_3$ integrin is confirmed by ELISA method. It is confirmed that RGD4C-EcCD_WT and RGD4C-EcCD_D314A have the ability to bind to $\alpha_v\beta_3$ integrin relative to unfused EcCD_WT and EcCD_D314A (see FIG. 13A and Table 9), $K_d$ values are approximately 7.0±0.9 nM and 9.1±1.1 nM respectively. The RGDfv peptide at same concentration can inhibit about 30% binding capacity, while the RGDfv peptide at 10-fold concentration can inhibit about 80% binding capacity (see FIG. 13B). This experiment confirms that RGD4C-EcCD_WT and RGD4C-EcCD_D314A have the binding activity of $\alpha_v\beta_3$ integrin, and this binding has the specificity of RGD4C peptide $\alpha_v\beta_3$ integrin.

TABLE 9

The binding of EcCD series fusion protein and $\alpha_v\beta_3$ integrin receptor is analyzed by ELISA, and the bound $K_d$ value is calculated.

| Protein | $K_d$ (nM) |
| --- | --- |
| EcCD_WT | N/A |
| RGD4C- EcCDWT | 7.0 ± 0.9 |
| EcCD_D314A | N/A |
| RGD4C- EcCD_D314A | 9.1 ± 01.1 |

Figure 14A:
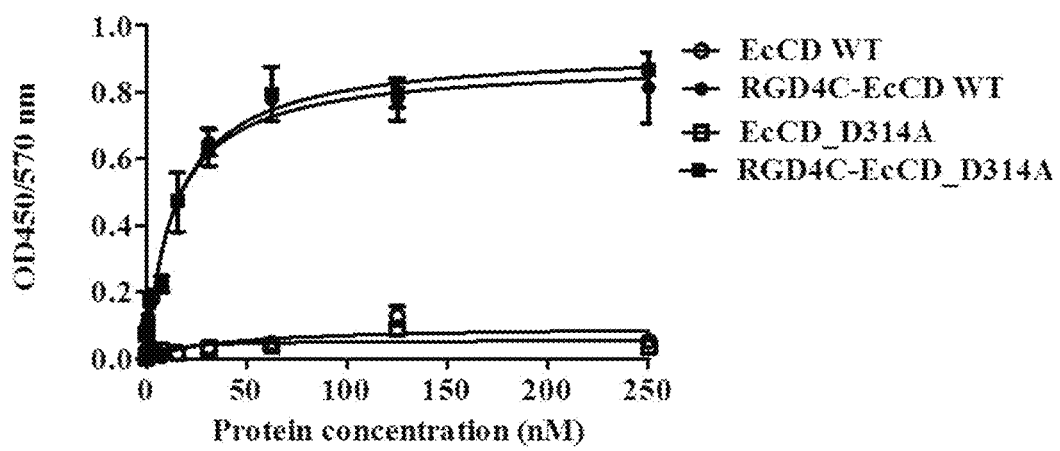
Figure 14B:
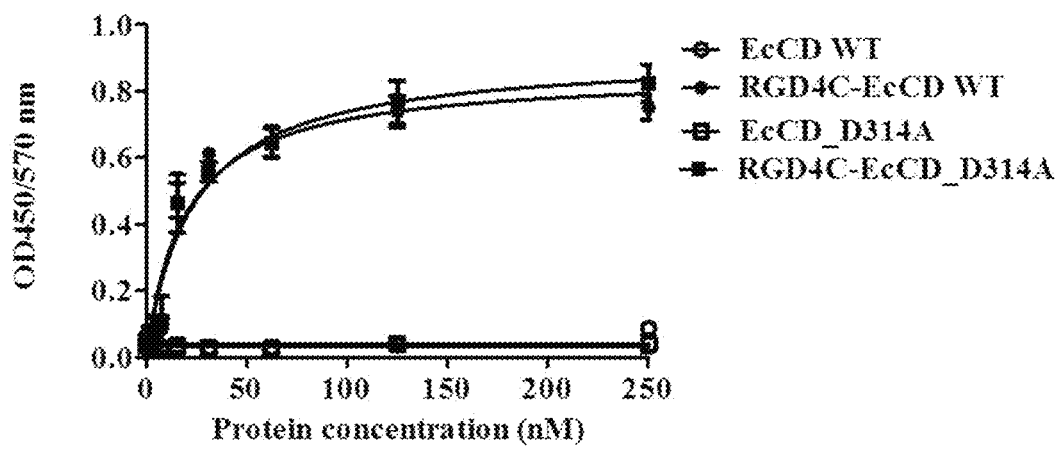
Figure 14C:
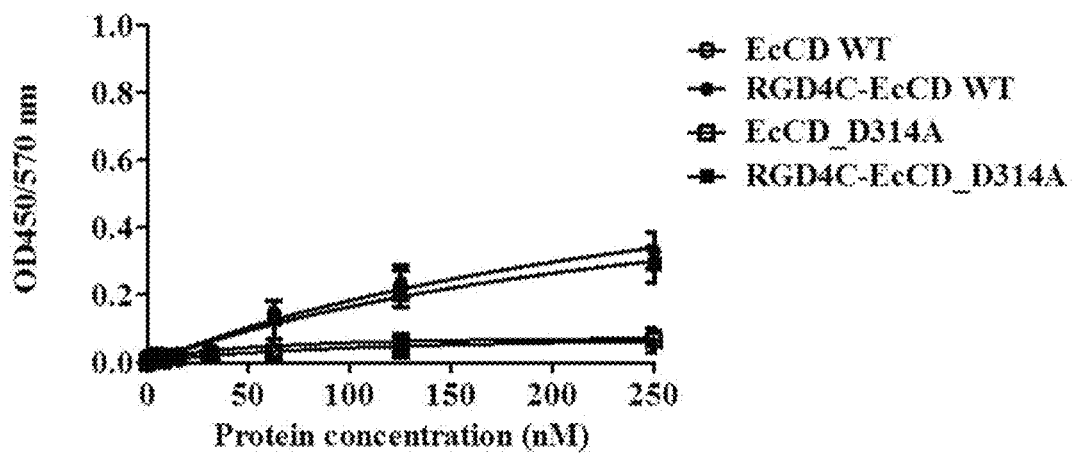
Figure 14D:
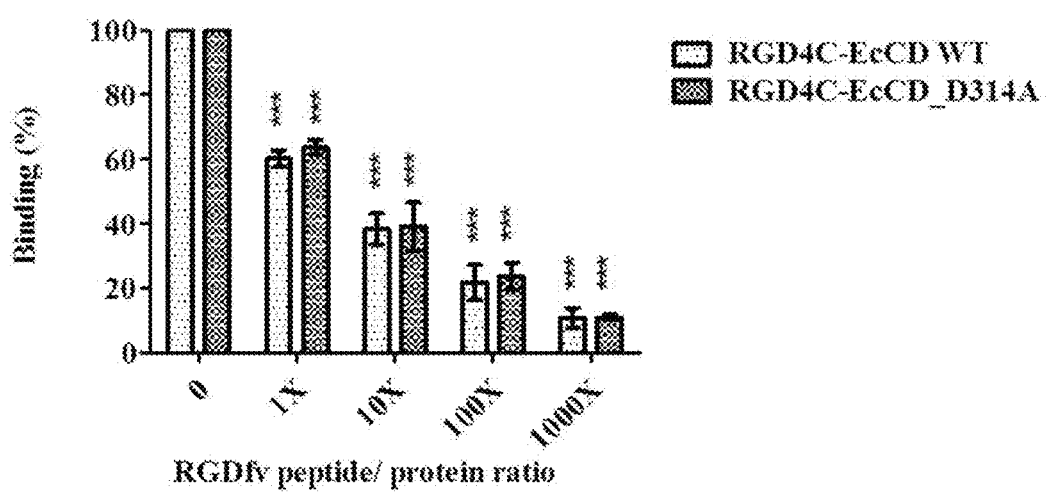
Figure 14E:
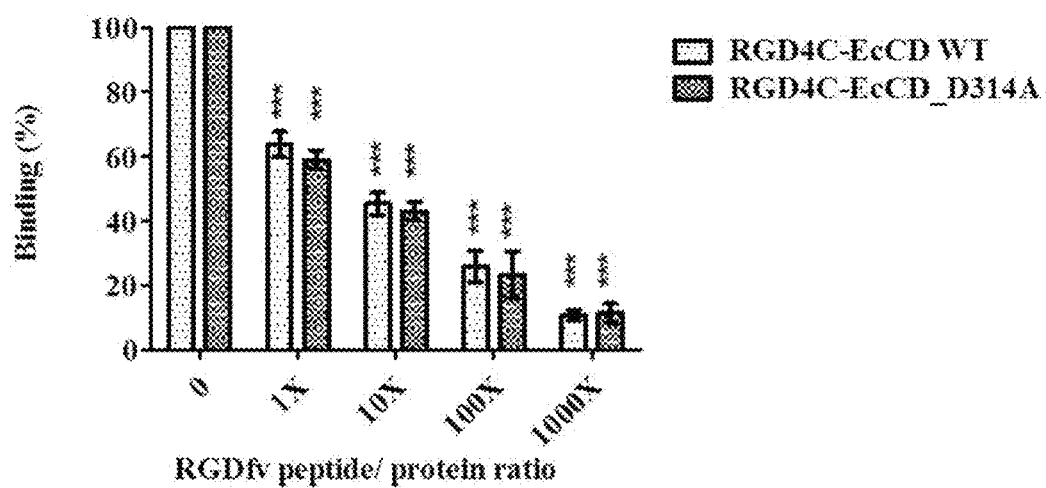

13. Binding Activity and Specificity Test of EcCD Series Fusion Protein and U87MG, HUVEC and MCF-7 Cell Strain To confirm whether RGD4C-EcCD_WT and RGD4C-EcCD D314A are bound to the $\alpha_v\beta_3$ integrin cell strain, ELISA is used to experiment that U87MG and HUVEC cells with high expression of $\alpha_v\beta_3$ integrin and MCF-7 cells with low expression of $\alpha_v\beta_3$ integrin are seeded in 96-well ELISA microplate, after the cells are fixed, add EcCD series fusion protein (0~250 nM) at different concentrations, then detect the protein with anti-His6tag-HRP Mab and color with TMB, stop the reaction and then measure the absorbed light reading value of OD450 nm/OD570 nm to quantify the amount of protein bound to the cell, and calculate the dissociation constant $K_d$ value of the protein-cell binding. The results show that RGD4C-EcCD_WT and RGD4C-EcCD_D314A have the ability to bind to U87MG and HUVEC cells relative to unfused EcCD_WT and EcCD_D314A of RGD4C peptide (see FIG. 14A, FIG. 14B and Table 10), and calculate the $K_d$ value of RGD4C-EcCD_WT bound with U87MG and HUVEC cells, which is 13.8±1.9 nM and 20.3±3.3 nM respectively, while the results of RGD4C-EcCD_D314A bound to U87MG and HUVEC cells are similar, the $K_d$ values are 15.1±1.8 nM and 23.3±3.4 nM respectively. As for the poor binding of RGD4C-EcCD_WT and RGD4C-EcCD_D314A to the negative control MCF-7 cells (see FIG. 14C and Table 10), the $K_d$ values are 327.1±119.5 nM and 299.9±126.2 nM respectively. It can be observed that the binding ability of RGD4C-EcCD_WT to U87MG and HUVEC cells is 23.7 and 16.1 times higher than that of MCF-7 respectively, and the results of RGD4C-EcCD_D314A are similar, which are 19.9 and 12.9 times higher than that of MCF-7 respectively, indicating that the binding ability of RGD4C to cells depends on the expression amount of $\alpha_v\beta_3$ integrin, RGDfv peptide competition at 10-fold relative concentration can inhibits about 50% binding (see FIG. 14D and FIG. 14E). It is confirmed from the above experimental results that the EcCD series protein fused to the RGD4C peptide has the binding activity with the expressing $\alpha_v\beta_3$ integrin cell strain, and the binding has the specificity of the RGD4C peptide and $\alpha_v\beta_3$ integrin of the cell expression, and also confirmed that the D314A mutation will not affect the binding activity of the RGD4C peptide and $\alpha_v\beta_3$ integrin.

TABLE 10

Binding activity and specificity test of EcCD series fusion protein with U87MG, HUVEC and MCF-7 cell strain

| Cell ($K_d$ value, nM) | RGD4C-EcCD_WT | RGD4C-EcCD_D314A | RGD4C-yCD |
| --- | --- | --- | --- |
| U87MG ($\alpha_v\beta_3$ integrin(+++)) | 13.8 ± 1.9 | 15.1 ± 1.8 | 53.7 ± 5.6 |
| HUVEC($\alpha_v\beta_3$ integrin(+++)) | 20.3 ± 3.3 | 23.3 ± 3.4 | 47.5 ± 7.4 |
| MCF-7($\alpha_v\beta_3$ integrin(−)) | 327.1 ± 119.5 | 299.9 ± 126.2 | 365.9 ± 104.1 |

Figure 15A:
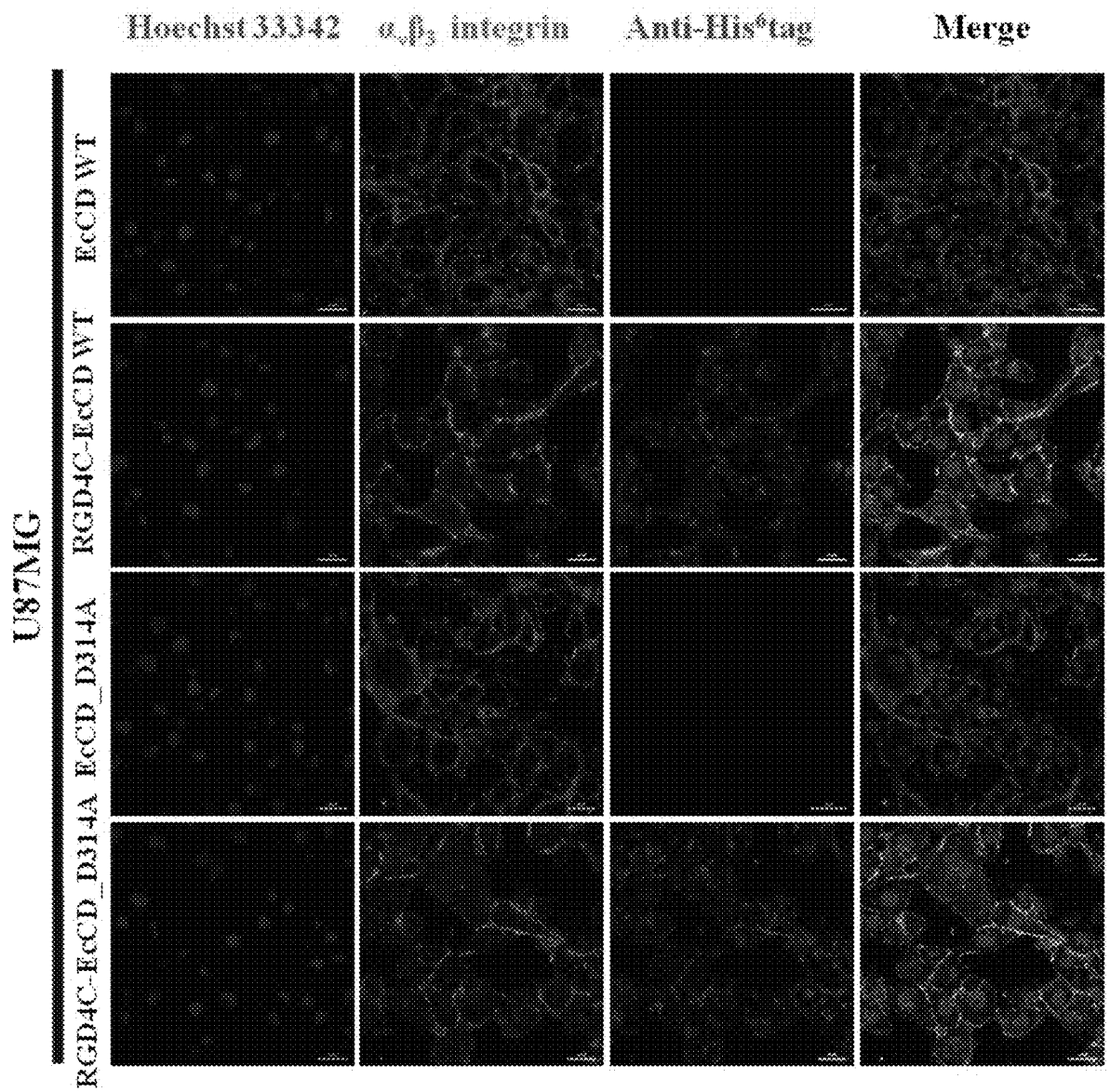
FIGS. 15A-15C show the binding and distribution of EcCD fusion proteins in U87MG, HUVEC and MCF-7 cell strain. The immunofluorescence staining is used to observe and experiment the EcCD fusion protein, which are respectively acted with U87MG cells in FIG. 15A, HUVEC cells in FIG. 15B and MCF-7 cells in FIG. 15C for 2 hours at 37° C., then fixed with 2% para-formadehyde, the fixed cells are first permeabilized with 0.1% Triton X-100 for 10 minutes, after that, cultured with 1% BSA blocking (dissolved in PBS containing $Ca^{2+}$, $Mg^{2+}$) for 1 hour at room temperature, then add a 1st antibody (Rabbit anti-His$^6$tag, Mouse anti-human CD51/61$α_vβ_3$ integrin), and then add a 2nd antibody (Anti-rabbit IgG-CF640R, Anti-mouse IgG-Alexa488), the protein distribution is observed by conjugated fluorescence microscope. (Green signal: $α_vβ_3$ integrin; red signal: anti-His$^6$tag; blue signal: Hoechst 33342 cell nucleus stain) (Scale bars: 20 μm)
Figure 15B:
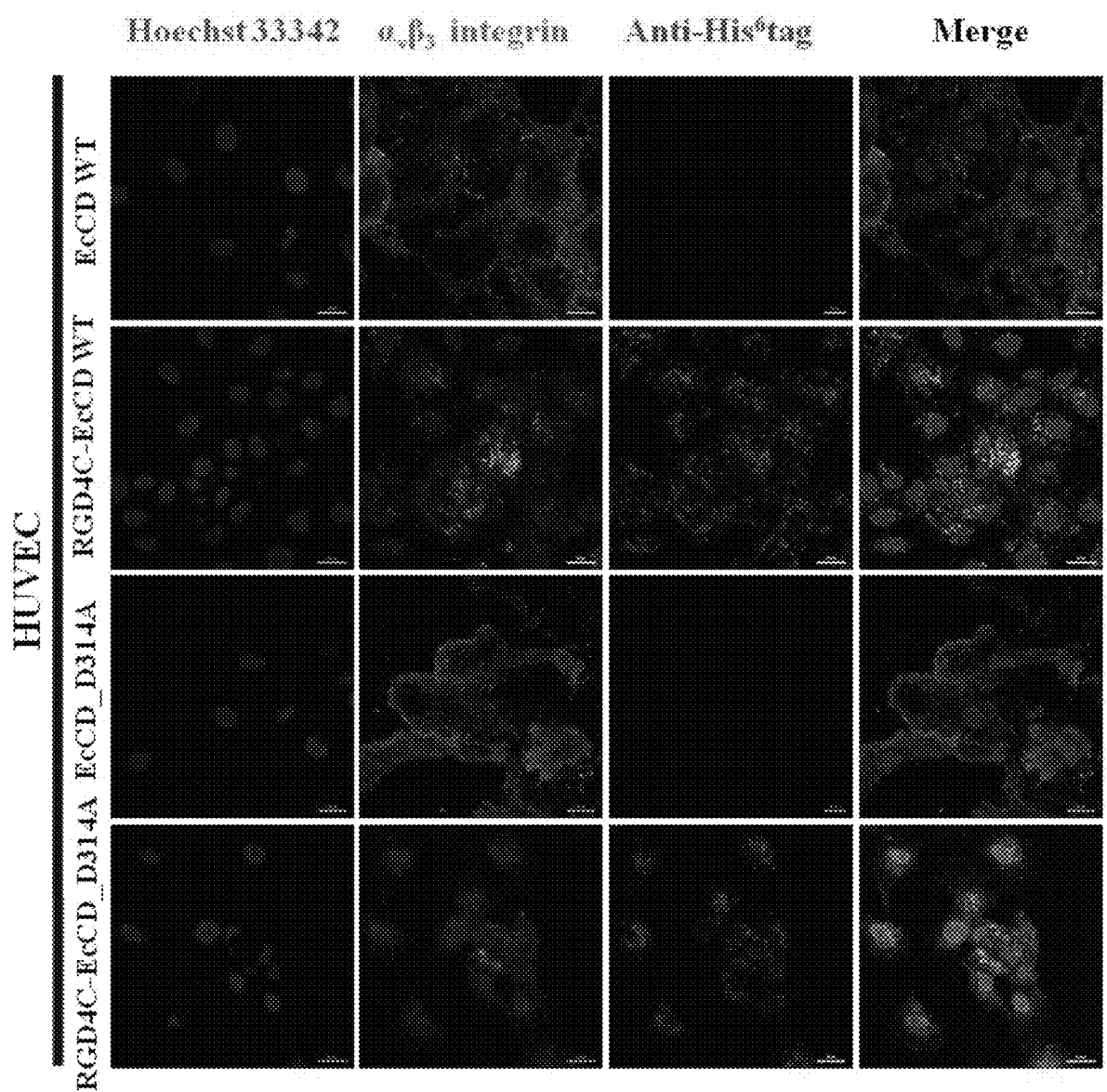
Figure 15C:
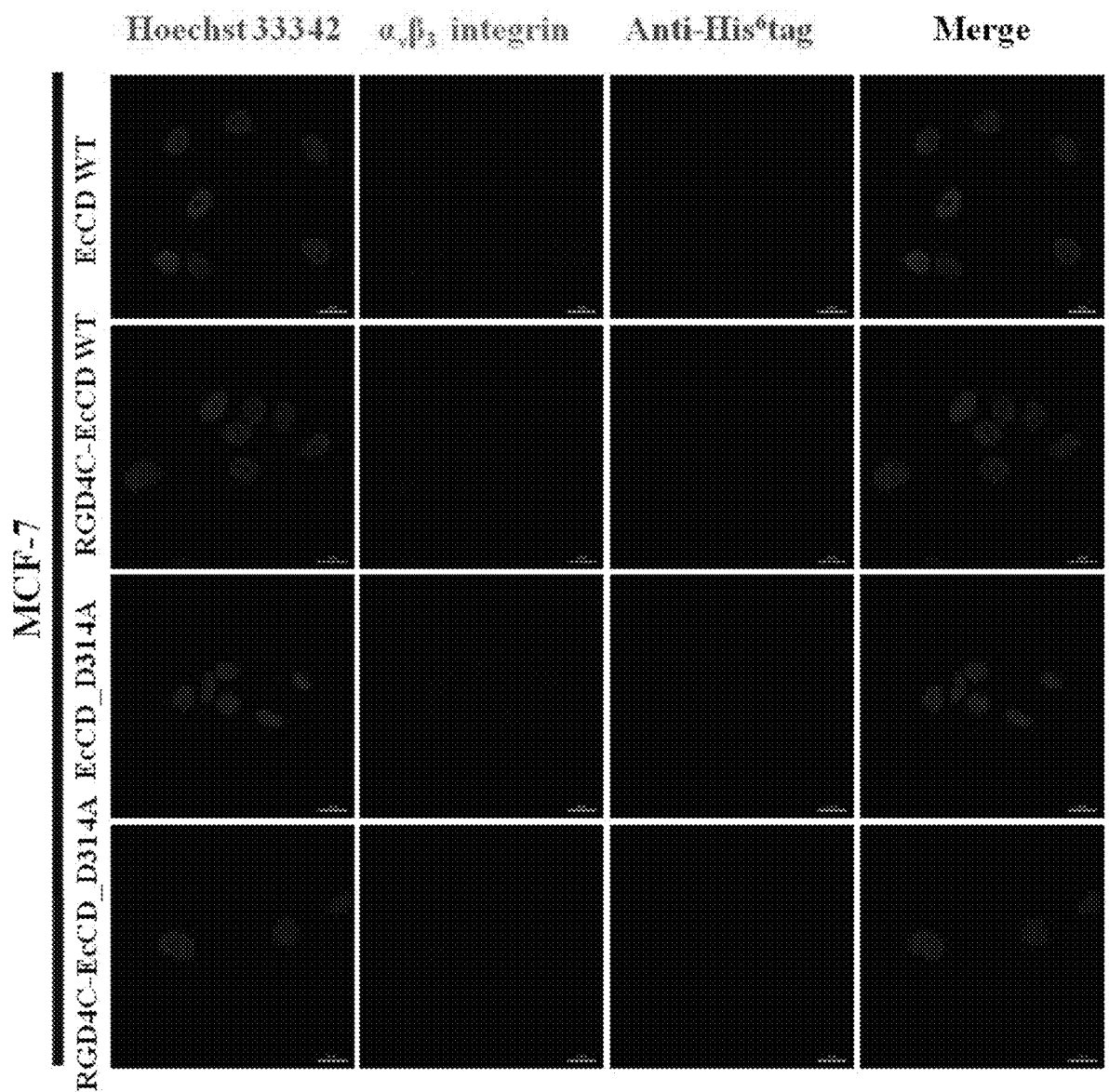

14. EcCD Series Fusion Protein Bound with U87MG, HUVEC and MCF-7 Cell Strain and Distributed in the Cells Immunofluorescence is used to observe the distribution of the protein bound with cell in the cell. U87MG, HUVEC and MCF-7 cells act with culture medium containing EcCD_WT, RGD4C-EcCD_WT, EcCD_D314A and RGD4C-EcCD_D314A proteins at 37° C. for 2 hours, stain the cell, and observe protein distribution by the conjugated fluorescence microscopy. It is known from the resulted that EcCD_WT and EcCD_D314A are not observed on the cell due to no red light signal (red light: anti-His6tag), only the green light signal of $\alpha_v\beta_3$ integrin is observed, which indicates that EcCD_WT and EcCD_D314A do not have the ability of binding with U87MG and HUVEC cells. Relative to EcCD_WT and EcCD_D314A, RGD4C-EcCD_WT and RGD4C-EcCD_D314A have the ability of binding with U87MG and HUVEC cells (see FIG. 15A and FIG. 15B). The binding of RGD4C-EcCD_WT and RGD4C-EcCD_D314A (red light: anti-His6tag) can be observed on the cell surface, and it is superimposed with the $\alpha_v\beta_3$ integrin (green light) detected by the antibody (yellow light), which indicates that its binding is specific. At the same time, it can be observed that RGD4C-EcCD_WT and RGD4C-EcCD_D314A will enter the internalization. It is proved from the above experiment that RGD4C-EcCD_WT and RGD4C-EcCD_D314A will enter the internalization by binding to $\alpha_v\beta_3$ integrin on U87MG and HUVEC cells, and this binding is specific; for MCF-7 cells, EcCD series fusion protein is not observed on the cells (due to that no red light signal is observed), and no green signal is observed, and MCF-7 cell is also shown to have low expression of $\alpha_v\beta_3$ integrin (see FIG. 15C).

Figure 16A:
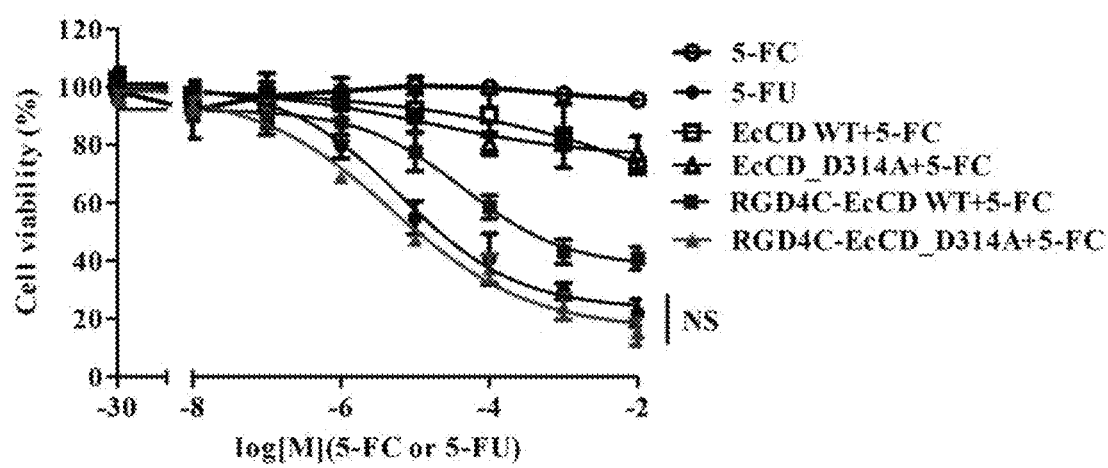
FIGS. 16A-16E show that in vitro cell killing effect of the EcCD fusion protein combined with 5-FC. Relative cell viability was measured by MTT assay. The 50 nM EcCD series fusion protein is applied to U87MG, HUVEC and MCF-7 cells at 37° C. for 2 hours, after washing the unbound protein with PBS. In combination with 5-FC at different concentrations, separately add the group of 5-FU and 5-FC at different concentrations as the positive control group and the negative control group, the cell survival proportion is expressed by the amount of live cell metabolite formazan in MTT, and calculate the $IC_{50}$ value of the 5-FC concentration.
Figure 16B:
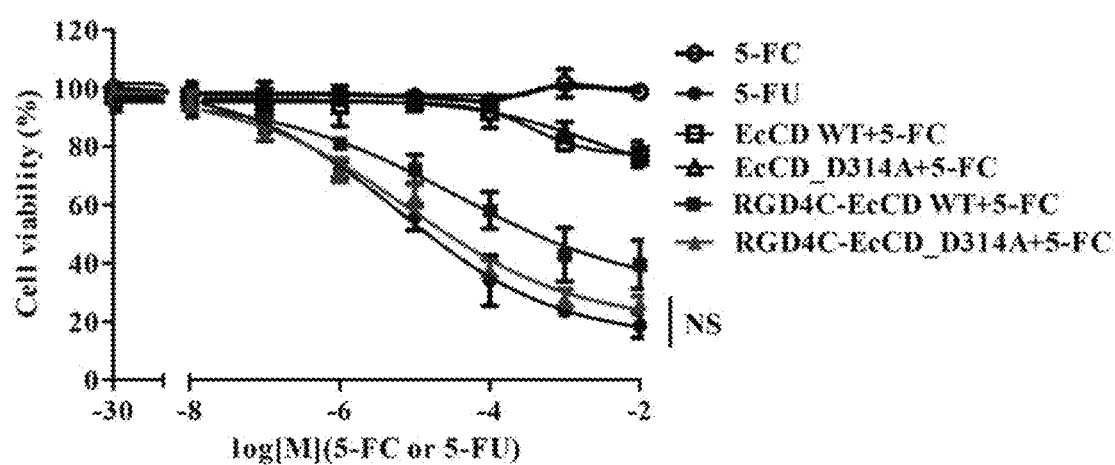
Figure 16C:
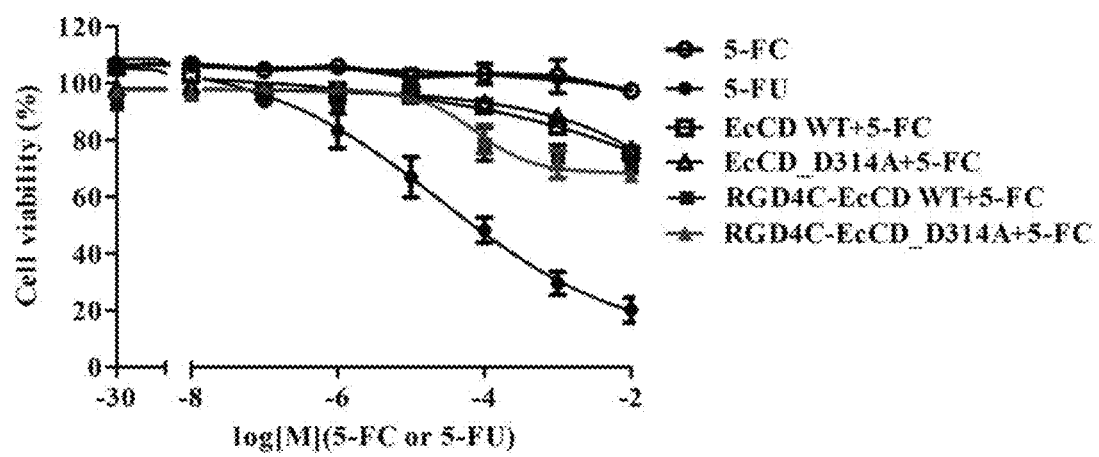

15. Cytotoxic Test of EcCD Series Fusion Protein Coupled with 5-FC to Treat with U87MG, HUVEC and MCF-7 Cells To confirm whether RGD4C-EcCD_WT and RGD4C-EcCD_D314A can kill the cells by the principle of enzyme prodrug system, so it is further tested by MTT assay. After the EcCD series fusion protein (50 nM) is dissolved in the cell culture medium and cultured at 37° C. for 2 hours, the protein of the unbound or un-endocytosed cells are washed out with PBS, and 5-FC and 5-FU at different concentrations are added and cultured at 37° C. for 72 hours, and the cell survival ratio is observed by MTT assay, and its IC50 (half maximal inhibitory concentration) is obtained (see FIG. 16A, FIG. 16B, FIG. 16C and Table 11). The results show that the survival rate of U87MG, HUVEC and MCF-7 cells in the negative control group treated separately with 5-FC is close to 100%, which indicates that 5-FC will not affect the cells, and EcCD_WT and EcCD_D314A treated with 5-FC also have no obvious killing effect (survival rate is higher than 75%), while the positive control group treated separately with 5-FU has the best effect. The $IC_{50}$ for U87MG, HUVEC and MCF-7 cells is: 6.5±0.2 μM, 6.5±1.3 μM and 25.6±0.3 μM respectively. As for the group of RGD4C-EcCD_WT treated with 5-FC, the $IC_{50}$ of U87MG and HUVEC cells is 44.1±1.5 μM and 35.9±2.6 μM respectively, although the effect is not as good as that of the positive control group directly treated with 5-FU, but there is also good killing ability, and the $IC_{50}$ of the group of RGD4C-EcCD D314A treated with 5-FC for U87MG and HUVEC cells is 5.0±1.4 μM and 8.2±1.5 μM respectively. The effect is significantly higher than that of RGD4C-EcCD_WT. The $IC_{50}$ is less 8.8 times and 4.4 times respectively. It showed that the 5-FC enzyme activity increased by D314A mutation may have the effect of increasing cell killing of EcCD/5-FC, the killing effect of RGD4C-EcCD_WT and RGD4C-EcCD_D314A for MCF-7 cell strain of $\alpha_v\beta_3$ integrin with low expression is worst, and $IC_{50}$ is greater than 10 mM. HUVEC is compared with U87MG the difference is more than 200 times. In terms of EcCD series fusion protein, although the killing effect of RGD4C-EcCD_WT combined with 5-FC does not meet the effect of 5-FC to be directly treated, but compared with the previous RGD4C-yCD, the effect is close, and RGD4C-EcCD_WT protein treatment concentration is 10 times lower than RGD4C-yCD, which indicates that RGD4C-EcCD_WT combined with 5-FC is better than RGD4C-yCD. The cell killing effect of RGD4C-EcCD_D314A combined with 5-FC is similar to that of 5-FU to be directly treated, which indicates that 5-FC enzyme activity increased by D314A mutation may improve the cell killing effect on EcCD/5-FC, while RGD4C-EcCD_WT and RGD4C-EcCD_D314A co-treated with 5-FC is safer than 5-FU, which indicates that this enzyme pro-system is safer.

concentrations are dissolved in cell culture medium and cultured at 37° C. for 2 hours, and then the unbound or un-endocytosed cells are washed with PBS, and cultured at 37° C. for 72 hours in 100 μM 5-FC. The cell survival ratio is observed by MTT assay. It was known from the results that RGD4C-EcCD_WT and RGD4C-EcCD_D314A have specific killing ability for U87MG and HUVEC cells of expressing αvβ3 integrin. The $IC_{50}$ of RGD4C-EcCD_WT for U87MG and HUVEC cells is 38.5±8.2 nM and 22.9±1.2 nM respectively. The $IC_{50}$ of RGD4C-EcCD_D314A is 4.0±1.4 nM and 9.8±1.5 nM respectively. The killing effect is obvious compared with RGD4C-EcCD_WT. As with the previous experimental results, the D314A mutation may improve the killing ability of EcCD/5-FC. The $IC_{50}$ of RGD4C-EcCD_WT and RGD4C-EcCD D314A relative to the RGD4C-yCD protein concentration is about 4.6~52.4 times, which shows that the killing ability of RGD4C-EcCD_WT and RGD4C-EcCD_D314A is better than RGD4C-yCD against U87MG and HUVEC cells. It is proved from the above experimental results that RGD4C-EcCD_WT and RGD4C-EcCD_D314A have specific killing ability for cells of expressing $\alpha_v\beta_3$ integrin, and are affected by the expression amount of $\alpha_v\beta_3$ integrin.

TABLE 12

Cytotoxic test of EcCD series fusion protein coupled with 5-FC for U87MG, HUVEC and MCF-7 cells. The protein reaction concentration $IC_{50}$ of cytotoxic effect of RGD4C-EcCD_WT and RGD4C-EcCD_D314A treated with U87MG and HUVEC cell are evaluated.

| Protein ($IC_{50}$) and 100 μM 5-FC | RGD4C-EcCD_WT | RGD4C-EcCD_D314A | RGD4C-yCD (500 nM) |
|---|---|---|---|
| U87MG | 38.5 ± 8.2 nM | 4.0 ± 1.4 nM | 177.0 ± 12.4 nM |
| HUVEC | 22.9 ± 1.2 nM | 9.8 ± 1.5 nM | 209.4 ± 16.8 nM |

16. Preparation of yCD Series Protein Modified by Bifunctional Base Metal Chelating Agent (DTPA)

Figure 16D:
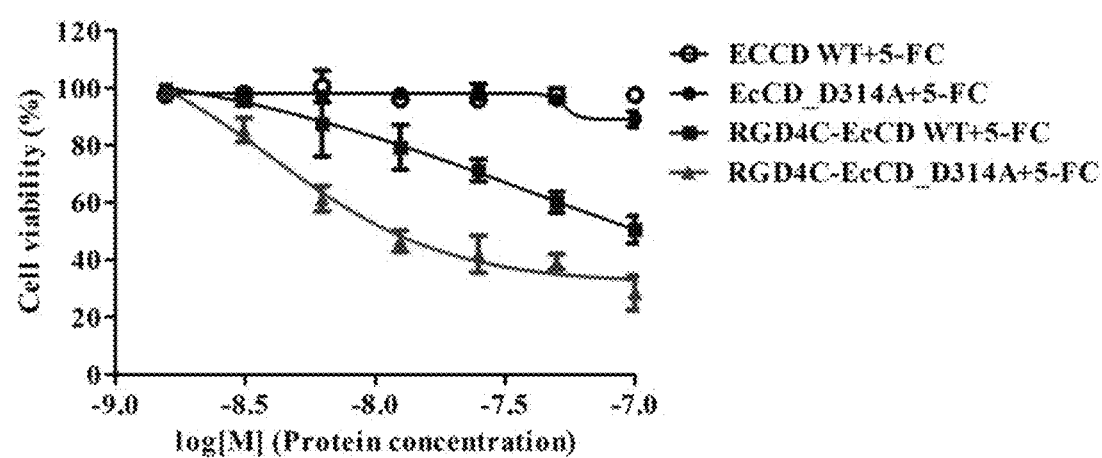
Figure 16E:
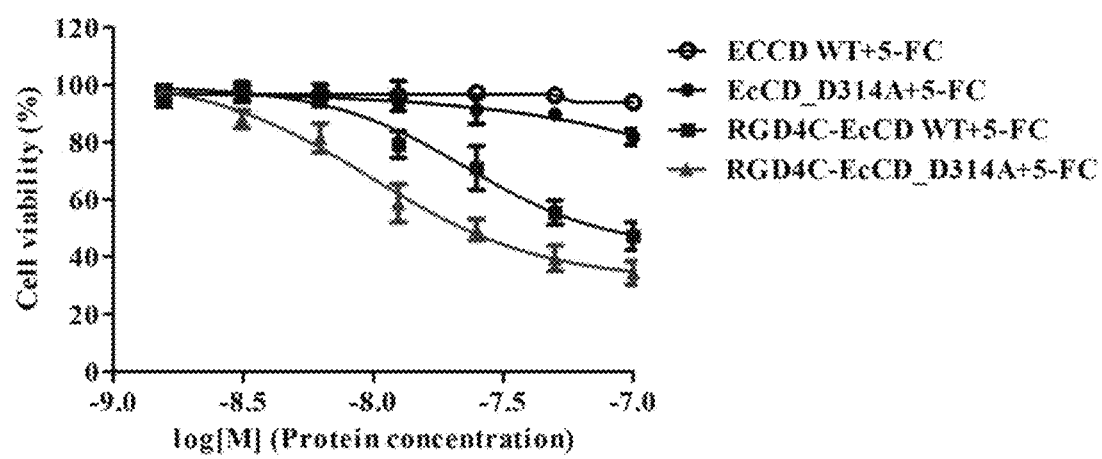
Figure 17A:
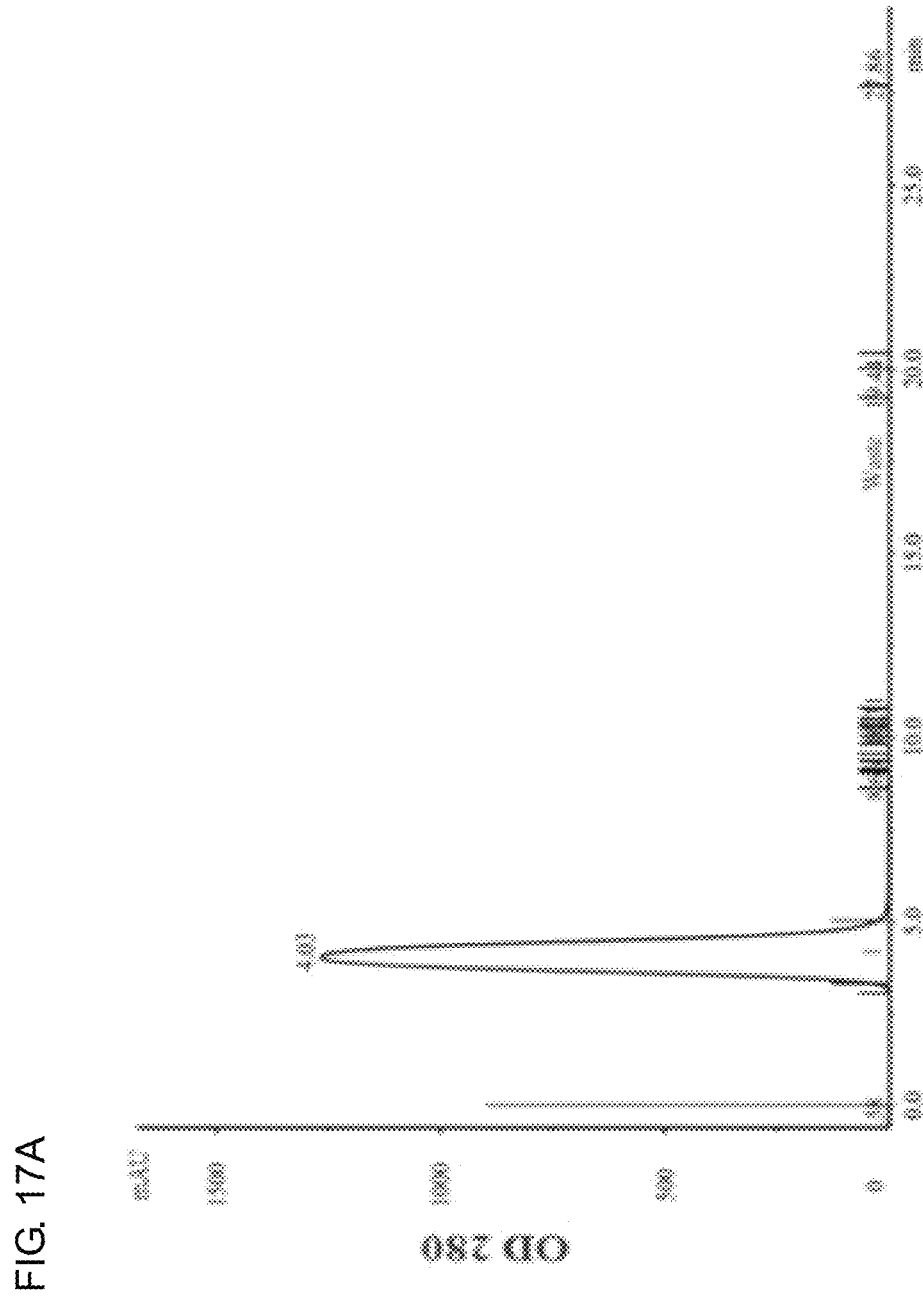
FIGS. 17A-17D show the elution curve of the protein reacted with DTPA dianhydride purified by AKTA FPLC desalting column.
Figure 17B:
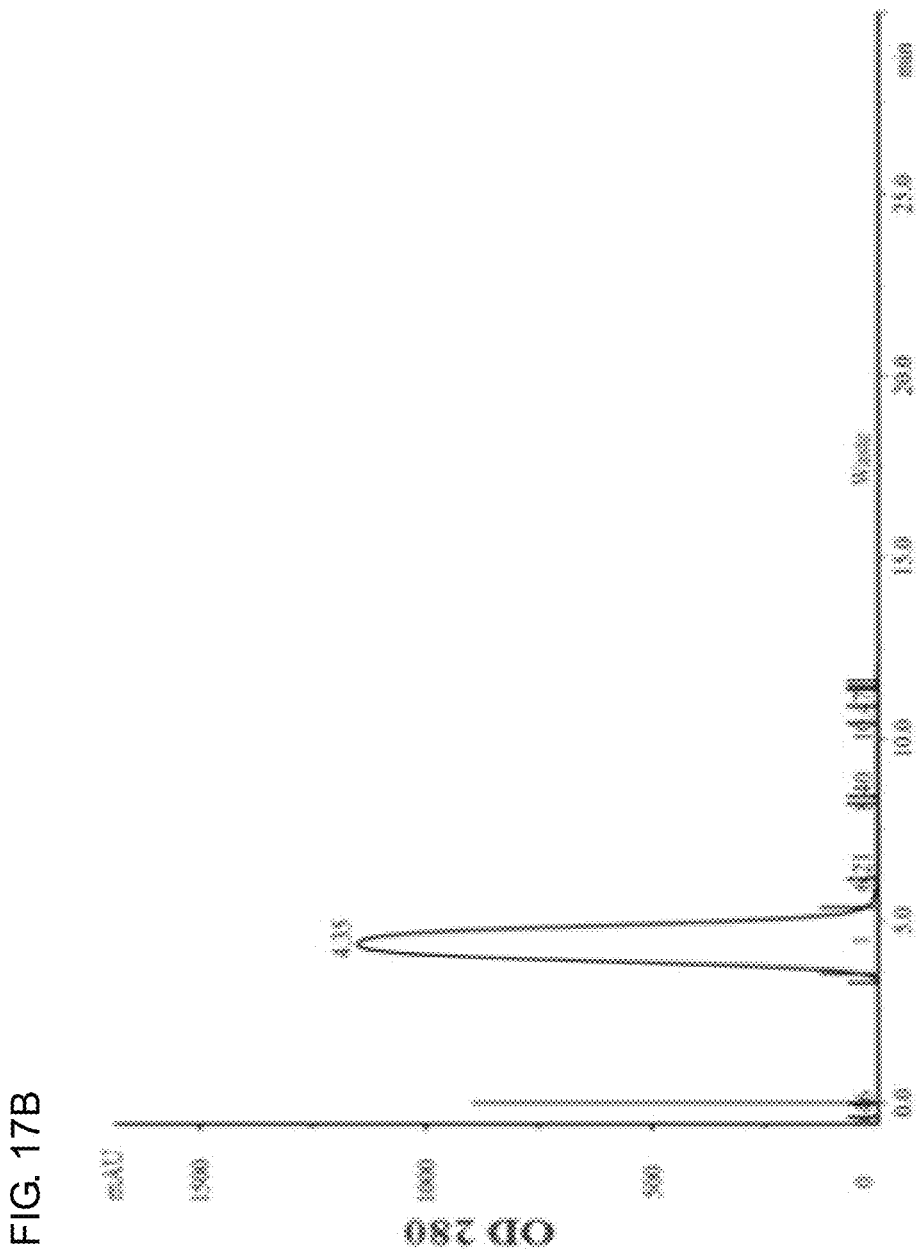
Figure 17C:
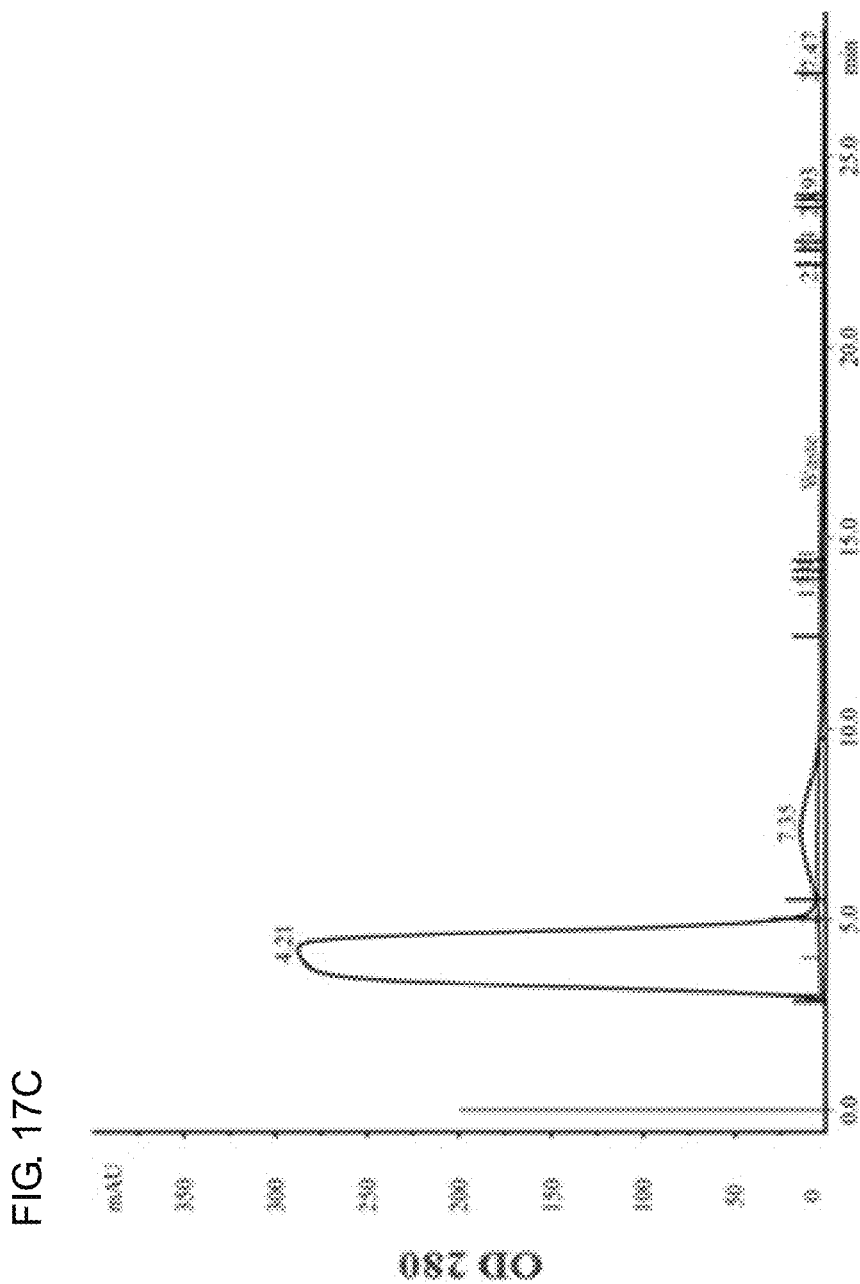
Figure 17D:
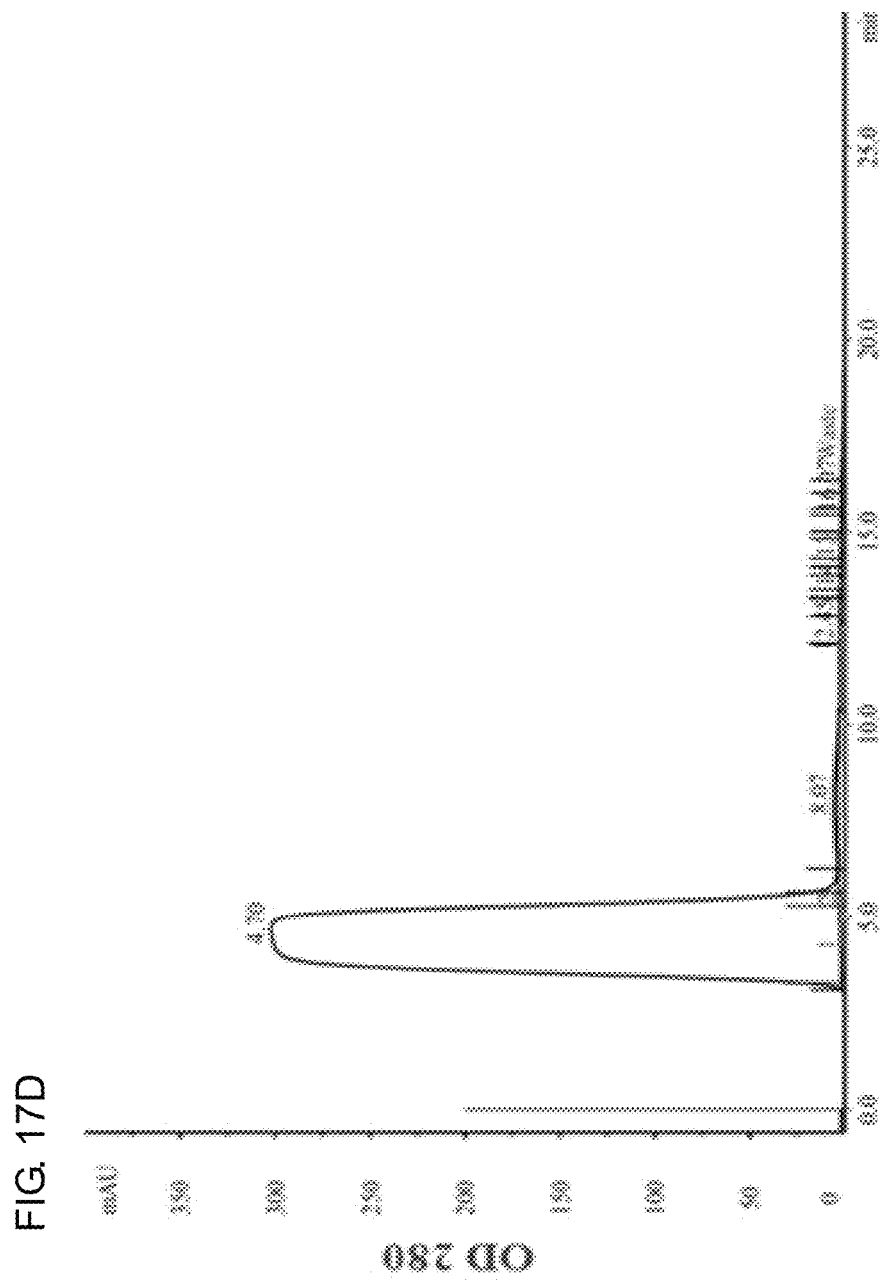

The protein and DTPA dianhydride are dissolved in 20 mM HEPES buffer (pH 7) solution at a molar ratio of 1:10, and reacted at room temperature for 1 hour. After the reaction is completed, the protein is separated by AKTA FPLC Desalting Column (Desalting HiPrep 26/10 column), and purified with small molecular weight salts. The tubular column material is G25 sephadex, the elution phase is 20 mM HEPES buffer (pH 7) solution, and the elution rate is set as 4.0 mL/min. FIG. 17A and FIG. 17B show yCD and RGD4C-yCD respectively. The two protein samples are eluted out at about 4 minutes when entering the tubular column (red vertical line); FIG. 17C and FIG. 17D respec- In order to confirm the protein reaction concentration $IC_{50}$ of killing effect of RGD4C-EcCD_WT and RGD4C-EcCD_D314A against U87MG and HUVEC cells (see FIG. 16D, FIG. 16E and Table 12), the proteins at different tively show DTPA-yCD and DTPA-RGD4C-yCD for modifying the metal chelating agent (DTPA). The two modified protein samples are eluted out at about $4^{th}$ to $5^{th}$ minute when entering the tubular column (red vertical line), and the light

TABLE 11

The EcCD series fusion protein is combined with 5-FC for U87MG cell cytotoxic test, HUVEC and MCF-7 cells, and the cell viability is detected by MTT assay for killing test, and find oud its $IC_{50}$ (half maximal inhibitory concentration).

| Protein (50 nM) and 5-FC or 5-FU ($IC_{50}$) | RGD4C-EcCD_WT | RGD4C-EcCD_D314A | RGD4C-yCD (500 nM) | 5-FU |
|---|---|---|---|---|
| U87MG | 44.1 ± 1.5 μM | 5.0 ± 1.4 μM | 37.1 ± 15.4 μM | 6.5 ± 0.2 μM |
| HUVEC | 35.9 ± 2.6 μM | 8.2 ± 1.5 μM | 23.6 ± 3.5 μM | 6.2 ± 1.3 μM |
| MCF-7 | >10 mM | >10 mM | 5130.7 ± 1002.4 μM | 25.6 ± 0.3 μM | absorption value measured at $7^{th}$ to $8^{th}$ minute is DTPA salts. The protein modified by metal chelating agent (DTPA) can be successfully purified by AKTA FPLC Desalting Column (Desalting HiPrep 26/10 column).

17. Enzyme Kinetic Analysis of yCD Series Proteins Modified by Metal Chelating Agent (DTPA)

Figure 18:
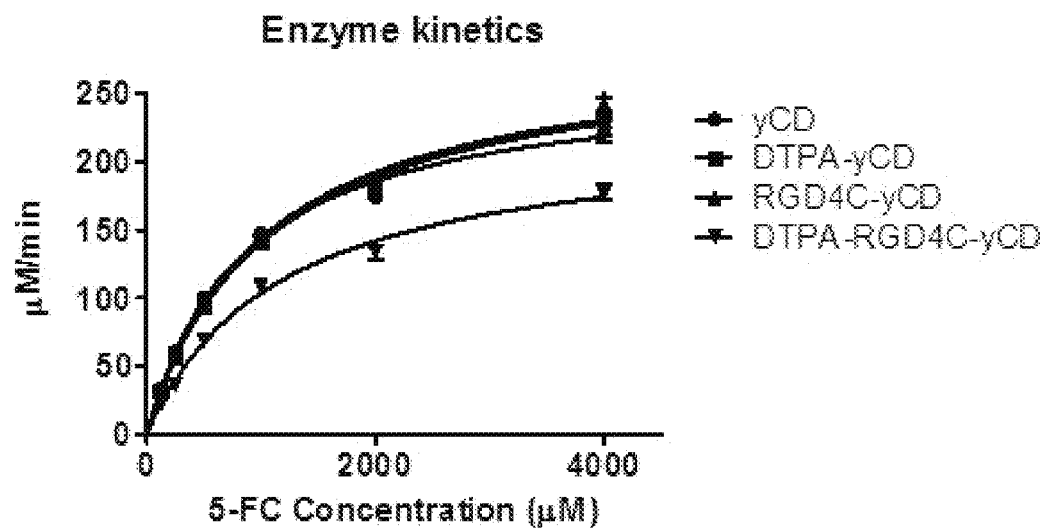
FIG. 18 shows the enzyme kinetic curve of DTPA-yCD and DTPA-RGD4C-yCD. The enzyme activity of yCD is not affected by DTPA modification. Compared with the original protein, DTPA-RGD4C-yCD is slightly reduced to 80%.

The curve and enzyme kinetic parameters (see FIG. 18 and Table 13) are fitted by the DNPA-modified protein enzyme kinetics through the Michaelis-Menten formula in the Graph prism program. The $V_{max}$ of DTPA-yCD is 286.8±10.80 μM/min, $K_m$ is 839.8±71.94 μM, which indicate that the enzyme activity of yCD is not affected by DTPA modification; the $V_{max}$ of DTPA-RGD4C-yCD is 224.6±8.408 μM/min, $K_m$ is 1163±107.8 μM; compared with the original protein, the enzyme activity is slightly affected by DTPA modification, and the $V_{max}$ of DTPA-RGD4C-yCD is reduced to 80%.

TABLE 13

Enzyme kinetic parameters $V_{max}$ and $K_m$

| Protein | $V_{max}$ (μM/min) | $K_m$ (μM) |
|---|---|---|
| yCD | 264.1 ± 8.256 | 839.8 ± 71.94 |
| DTPA-yCD | 286.8 ± 10.80 | 1038 ± 96.19 |
| RGD4C-yCD | 288.7 ± 8.883 | 1004 ± 73.19 |
| DTPA-RGD4C-yCD | 224.6 ± 8.408 | 1163 ± 107.8 |

Note: $V_{max}$ is the maximum initial velocity of the enzyme; $K_m$ is the concentration of the substrate required to reach half of $V_{max}$.

Figure 19:
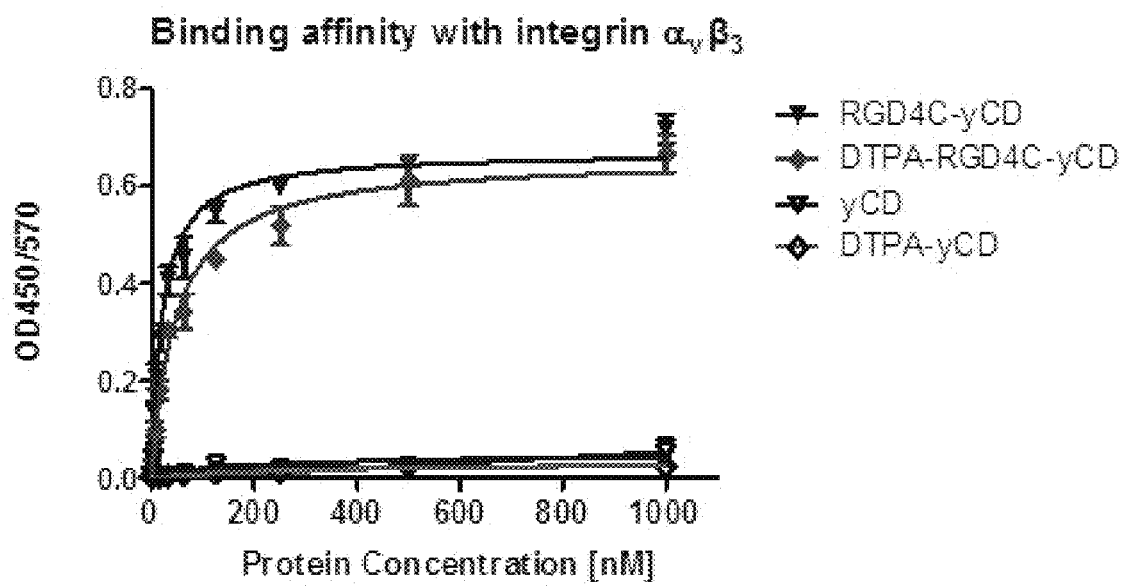
FIG. 19 shows a specific binding affinity analysis of DTPA-yCD and DTPA-RGD4C-yCD protein to integrin αvβ3 receptor by ELISA.

18. Binding Ability Analysis of yCD Series Protein and Integrin $\alpha_v\beta_3$ Receptor The curve and receptor binding ability parameters (see FIG. 19 and Table 14) are fitted by the binding ability of DTPA-modified protein and integrin $\alpha_v\beta_3$ receptor through the One site-Specific binding formula in the Graph prism program. Compared with RGD4C-yCD, the $K_d$ of DTPA-RGD4C-yCD is increased slightly to 47.6±5.9 nM, but it still has good receptor binding ability; yCD can not be bound with integrin $\alpha_v\beta_3$ receptor before and after modification.

TABLE 14

Binding ability parameters of DTPA-yCD and DTPA-RGD4C-yCD proteins and integrin $\alpha_v\beta_3$ receptor

| Protein | $K_d$ (nM) |
|---|---|
| yCD | N/A |
| DTPA-yCD | N/A |
| RGD4C-yCD | 20.7 ± 2.2 |
| DTPA-RGD4C-yCD | 47.6 ± 5.9 |

Note:
$K_d$ is the protein concentration required to reach half of $B_{max}$.

19. Physical Characterization Identification of yCD Series Proteins Modified by Metal Chelating Agent (DTPA)

Figure 20:
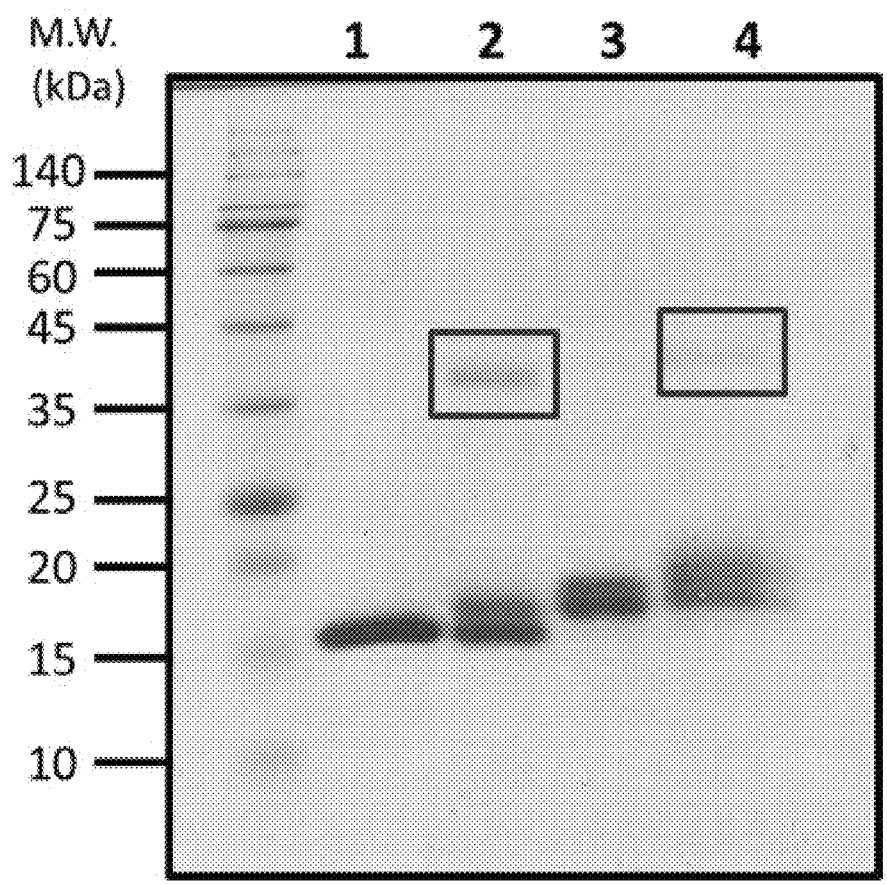
FIG. 20 shows the protein electrophoresis analysis of DTPA-yCD and DTPA-RGD4C-yCD. The molecular weights of DTPA-yCD (lane 2) and DTPA-RGD4C-yCD (lane 4) are higher than that of the original protein yCD (lane 1) and RGD4C-yCD (lane 3). DTPA-yCD formation dimer ratio is 8%. DTPA-RGD4C-yCD formation dimer ratio is 4%.
Figure 21:
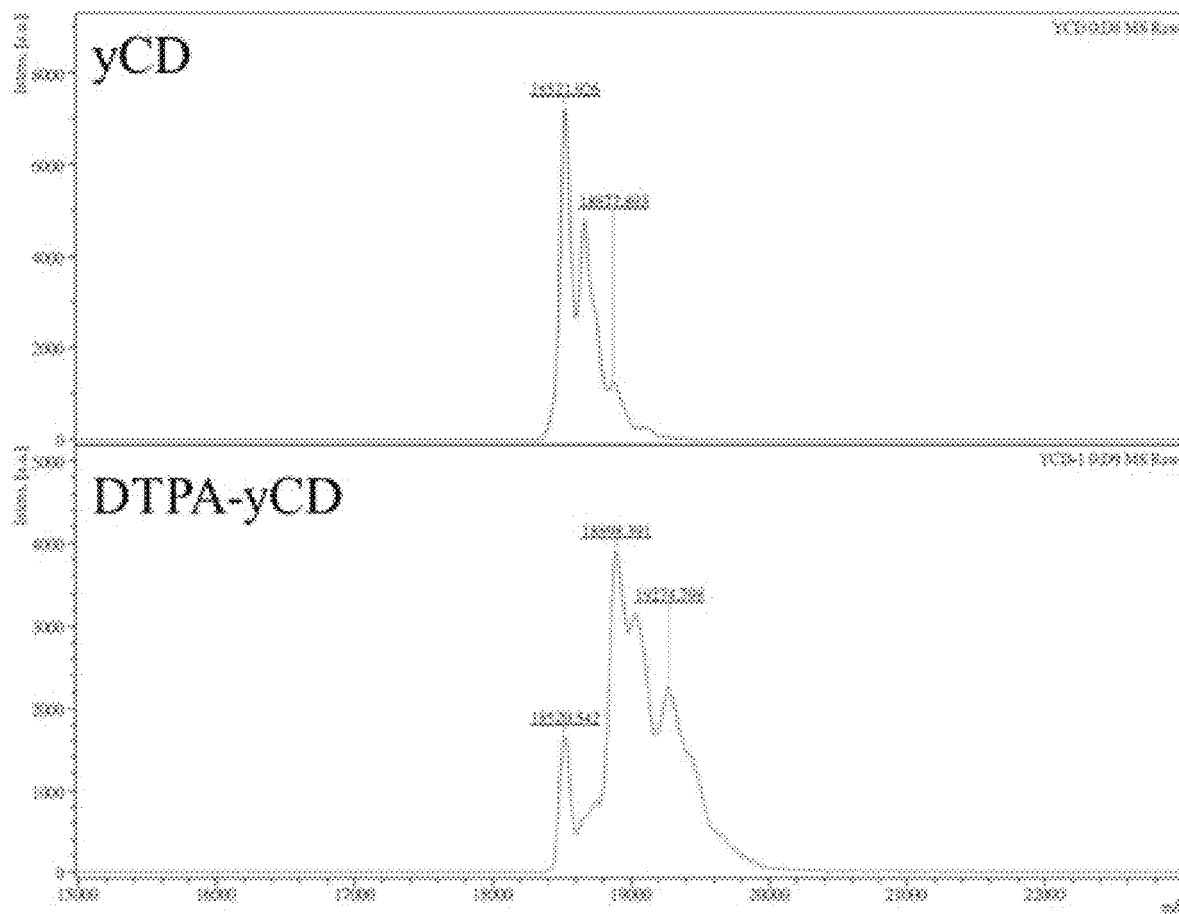
FIG. 21 shows the molecular weight and corresponding strength of the protein determined by using MALDI-TOF MS. The value indicated on the diagram is molecular weight, and the average yCD is modified by 1.16 DTPA.
Figure 22:
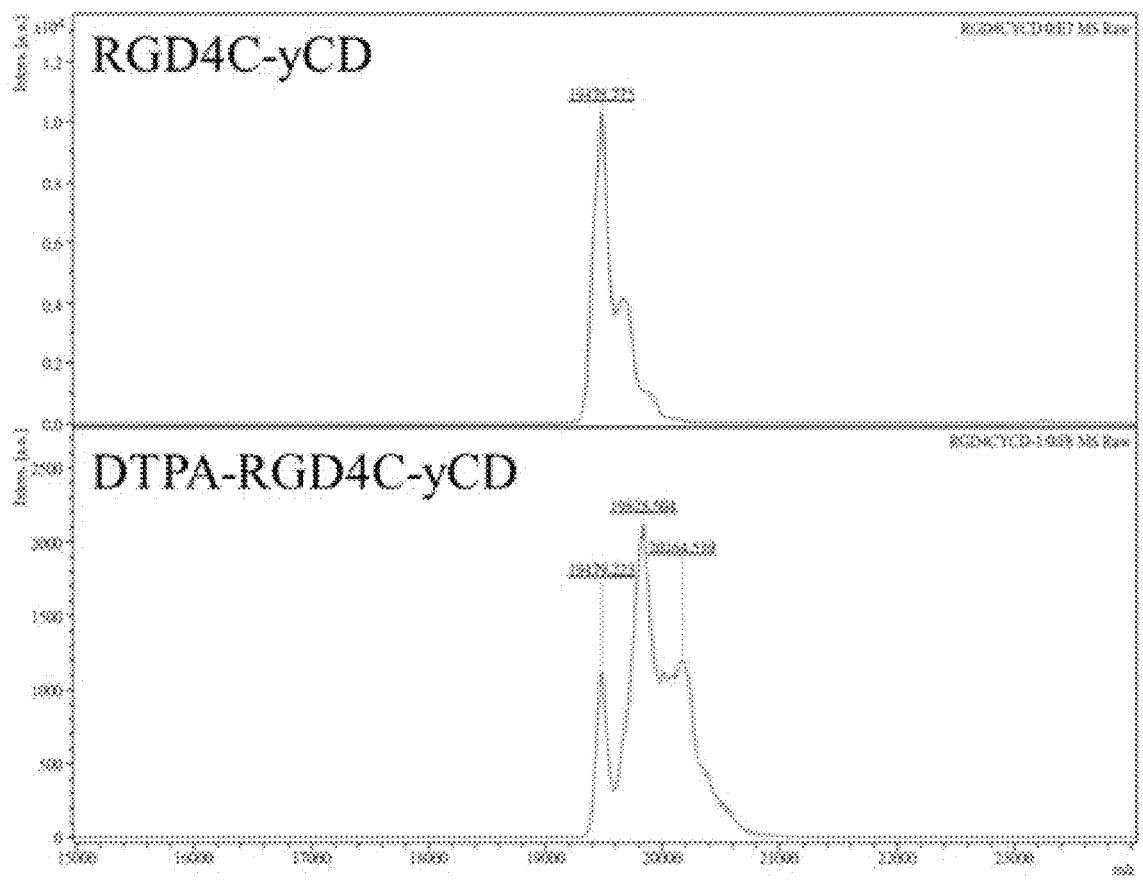
FIG. 22 shows the molecular weight and corresponding strength of the protein determined by using MALDI-TOF MS. The value indicated on the diagram is molecular weight, and the average RGD4C-yCD is modified by 0.94 DTPA.

DTPA is mainly modified on the primary amine of the protein. Since this DTPA is a di-anhydride type, the modification reaction has a chance to occur on the primary amine of two different proteins. If this reaction occurs, the molecular weight of the protein will increase by about twice, and the effectiveness of DTPA chelated metals (such as: Indium-111) may be affected. it can be seen from the results of protein electrophoresis (see FIG. 20), the molecular weights of DTPA-yCD (lane 2) and DTPA-RGD4C-yCD (lane 4) are larger than the original proteins yCD (lane 1) and RGD4C-yCD (lane 3). The ROI (red box) at twice the molecular weight (dimer) is selected by the software (Image J), and calculate its ratio in all the molecular weights, the ratio of DTPA-yCD forming dimer can be 8%; the ratio of DTPA-RGD4C-yCD forming dimer is 4%, both of which are less than 10%, which indicate that the DTPA simultaneous modification has no much reaction on the two proteins. In order to know the number of DTPA modifications on the protein, the molecular weight of the protein before and after the modification is measured by MALDI-TOF MS (Microflex MALDI-TOF MS (Bruker Daltonics), Mingxin Biotechnology Co., Ltd.) (see FIG. 21, Table 15, FIG. 22 and Table 16), by using the formula: (molecular weight after modification−molecular weight before modification)÷DTPA molecular weight after reaction (375 Da)×the ratio of the molecular weight intensity after modification accounting for all the intensities. After the modified protein signal is calculated by the formula, the modification number can be obtained. After calculation, yCD is modified to 1.16 DTPA on average; RGD4C-yCD is modified to 0.94 DTPA on average.

TABLE 15

Molecular weight and strength of yCD and DTPA-yCD determined by MALDI-TOF MS

| yCD | | DTPA-yCD | |
|---|---|---|---|
| Molecular weight m/z | Strength | Molecular weight m/z | Strength |
| 18521.926 | 7227 | 18520.542 | 1658 |
| 18662.807 | 4777 | 18898.391 | 3924 |
| 18877.983 | 1292 | 19029.247 | 3143 |
| 37180.566 | 384 | 19274.798 | 2277 |
| | | 37970.307 | 253 |

TABLE 16

Molecular weight and strength of RGD4C-yCD and DTPA-RGD4C-yCD determined by MALDI-TOF MS

| RGD4C-yCD | | DTPA-RGD4C-yCD | |
|---|---|---|---|
| Molecular weight m/z | Strength | Molecular weight m/z | Strength |
| 19478.775 | 10302 | 19479.223 | 1127 |
| 19662.162 | 4186 | 19828.504 | 2121 |
| 38950.150 | 905 | 20164.539 | 1206 |
| | | 39676.233 | 65 |

20. DTPA-yCD and DTPA-RGD4C-yCD Protein Labeled with Indium-111

Figure 23A:
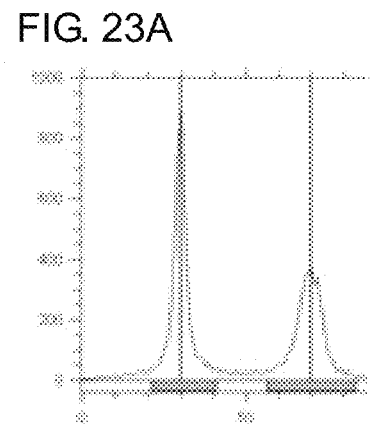
Figure 23C:
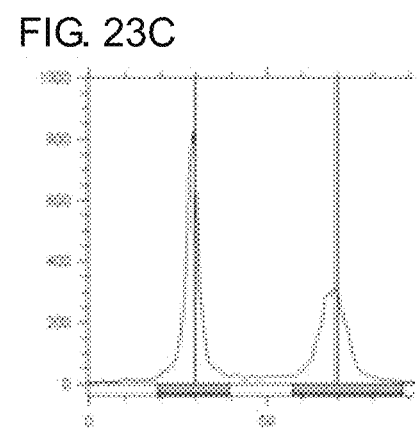
Figure 23B:
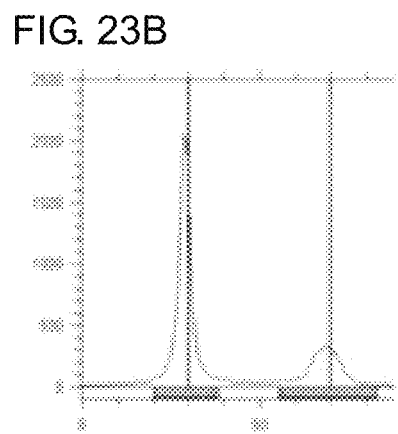
Figure 23D:
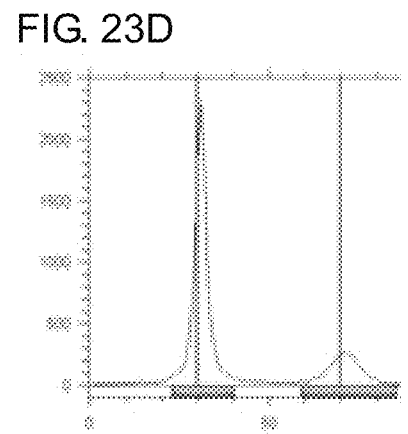
Figures 23E, 23G:
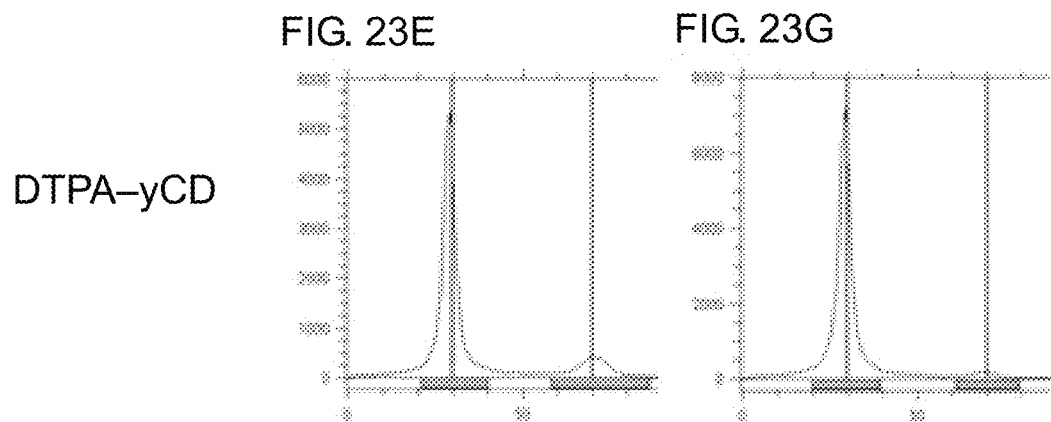
Figures 22H, 23F:
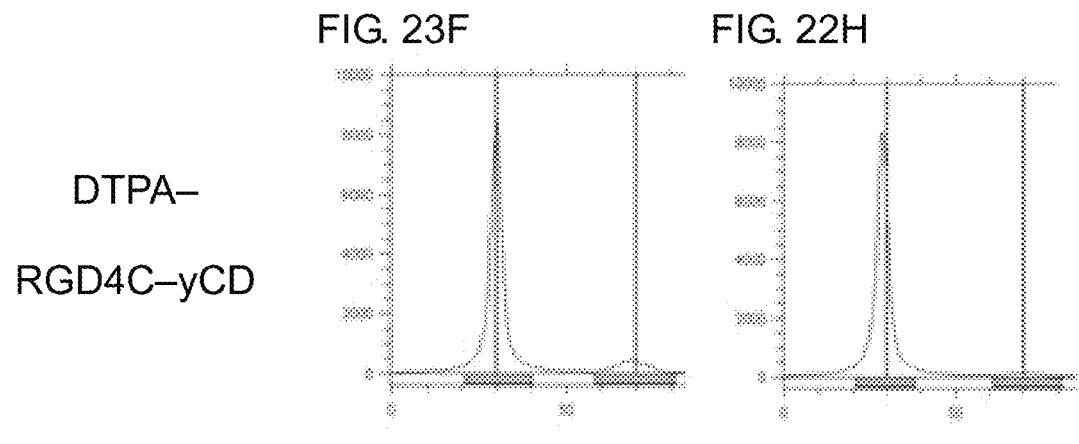
Figure 23I:
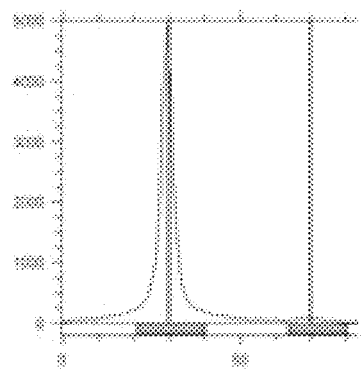
Figure 23J:
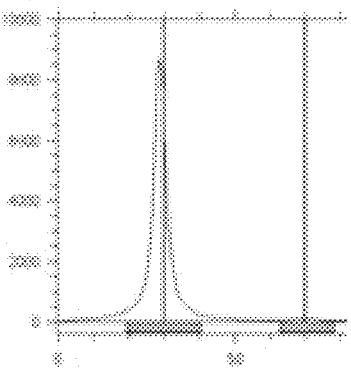

In the case of radiolabeling, the indium-111 was added to DTPA-yCD and DTPA-RGD4C-yCD protein (specific activity: 30 μCi/μg), and after reacting at 37° C. for 1 hour, the thin layer analysis method of ITLC-SG (Silica Gel) Media) is used to determine the radiochemical purity: the stationary phase is ITLC-SG (Silica Gel media), and the mobile phase is 0.5M, pH 4.6 citrate buffer solution. The indium-111 labeled protein will stay at origin, and the free indium-111 will be bound with citrate in the developing solution to form $^{111}$In-citrate and spread to solvent front. The indium-111 labeling efficiency of DTPA-yCD and DTPA-RGD4C-yCD is 54% and 73% respectively (see FIG. 23A and FIG. 23B). After that, EDTA added with a 10-fold molar excess of protein acts at room temperature for 1 hour to compete for indium-111 that un-chelated with DTPA. It can be seen that the radiochemical purity of $^{111}$In-DTPA-yCD and $^{111}$In-DTPA-RGD4C-yCD does not decrease significantly (see FIG. 23C and FIG. 23D). Finally, the centrifuge tube (3 kDa) of the membrane filtration concentration is used to separate the radioactive mark protein above 18 kDa and $^{111}$In-EDTA below 3 kDa. After $2^{nd}$ centrifugation, the radiochemical purity of $^{111}$In-DTPA-yCD and $^{111}$In-DTPA-RGD4C-yCD is 84% and 89% respectively (see FIG. 23E and FIG. 23F); after $4^{th}$ centrifugation, the radiochemical purity of both radioactive mark proteins can be more than 95% (see FIG. 23G and FIG. 23H); in the $5^{th}$ centrifugation, in addition to improving the radiochemical purity, it is mainly necessary that the solution is replaced from pH 5.5 to pH 7 HEPES buffer; and after analysis, $^{111}$In-DTPA-yCD and $^{111}$In-DTPA-RGD4C-yCD with high purity can be obtained. The final radiochemical purity is 96% and 97% respectively (see FIG. 23I and FIG. 23J). After purification, the protein is quantified and its specific activity is calculated. The recoveries are 64% and 57% respectively; the specific activity is 21 µCi/µg and 27 µCi/µg respectively.

Figure 24A:
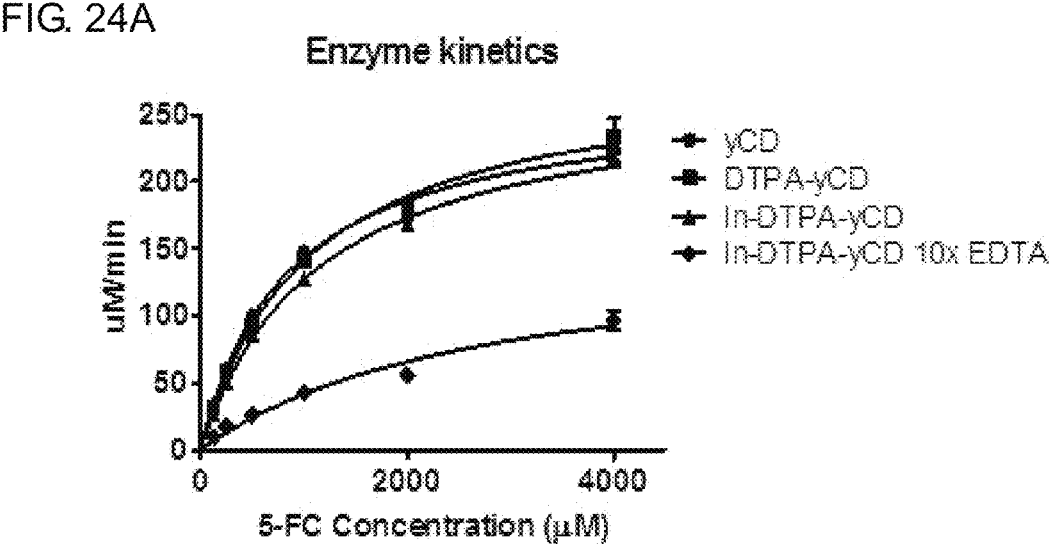
FIGS. 24A-24B show the kinetic curve of yCD series protein modified, labeled and purified by DTPA. The enzyme activity of the two proteins is not affected by the labeling conditions. After adding EDTA with a 10-fold molar excess of protein, and it is competitively purified, In-DTPA-yCD compared with the original enzyme activity. The Vmax in FIG. 24A is reduced to 47%; and the In-DTPA-RGD4C-yCD in FIG. 24B compared with the original enzyme activity, the Vmax is reduced to 40%.
Figure 24B:
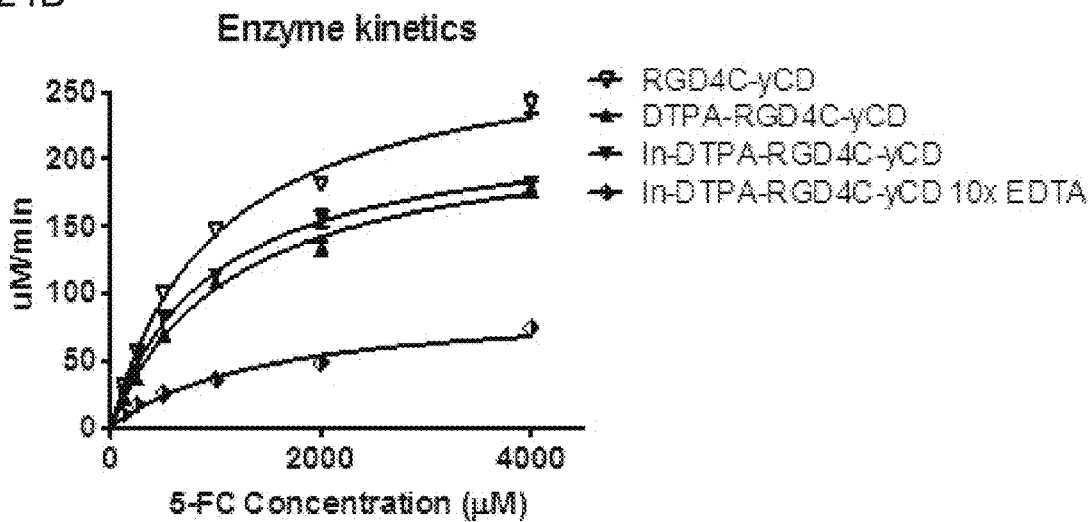
Figure 25:
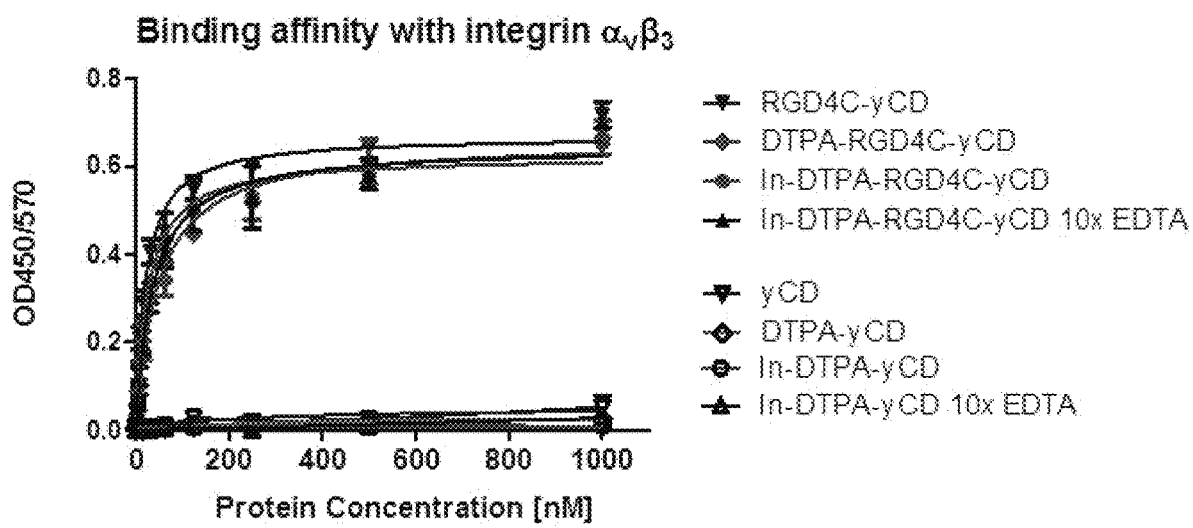
FIG. 25 shows the specific binding ability analysis of the DTPA modified and In-labeled yCD series protein to the integrin $\alpha_v\beta_3$ receptor by ELISA assay. In-DTPA-RGD4C-yCD under the condition of label, $K_d$ is 25.4±1.5 nM. After adding EDTA with a 10-fold molar excess of protein, the Kd of In-DTPA-RGD4C-yCD to the integrin $\alpha_v\beta_3$ receptor is 34.6±5.4 nM, indicating that the fusion protein is slightly affected by the reaction conditions. Wherein yCD can not be bound with the integrin $\alpha_v\beta_3$ receptor, with or without reaction conditions.

21. Biochemical Characteristics of DTPA Modified and Radiolabeled yCD Series Proteins Before the protein is labeled by radioisotope, its enzyme function must be determined, and based on the original enzyme function, it should be examined whether it will be affected during the radioactive marking process. The curve and enzyme kinetic parameters of protein are fitted by the Michaelis-Menten formula in the Graph prism program. The $V_{max}$ of yCD and RGD4C-yCD is 264.1±8.256 µM/min and 288.7±8.883 µM/min respectively, $K_m$ is 839.8±71.94 µM and 1004±73.19 µM respectively (see FIG. 24 and Table 17). Whether the yCD and RGD4C-yCD protein detected by the same method will be affected under the conditions of DTPA modification, marking and purification. Since the radioactive metal marking conditions will change the pH value to 5.5 and heat up to 37° C. for 1 hour, in order to evaluate the effect on the enzyme activity under these conditions, after simulating the same marking conditions, the stable isotope of indium is removed by membrane centrifugation, and the solution is replaced by pH 7.0 for enzyme activity analysis, and the $V_{max}$ and $K_m$ of In-DTPA-yCD and In-DTPA-RGD4C-yCD are obtained, which are similar to the enzyme activity after modification of DTPA, which indicates that this marking condition will not destroy the enzyme activity (see Table 24 and Table 17). After the completion of the radioactive metal mark, it is necessary to add EDTA of 10-fold protein Moire number and react at room temperature for 1 hour to compete for the radioactive metal isotope indium which is not chelated on DTPA. The EDTA in this step also has the chance to chelate the metal zinc ion of the enzyme catalytic center, the enzyme activity is impaired, so it is necessary to analyze the enzyme activity of In-DTPA-yCD and In-RGD4C-yCD protein after competition with EDTA. After the EDTA competitive reaction is completed, the enzyme kinetics analysis can be carried out by reducing the EDTA molecule weight through membrane centrifugation method and by replacing the solution with pH 7.0. As a result, the $V_{max}$ of In-DTPA-yCD and In-RGD4C-yCD is significantly reduced to 47% and 40%, and $K_m$ increases (see FIG. 24 and Table 17 below). The curve and receptor binding ability parameters of the protein and integrin $\alpha_v\beta_3$ are fitted under the conditions of DTPA modification, marking and purification by the One site-Specific binding formula in the Graph prism program (see FIG. 25 and Table 18). The $K_d$ of In-DTPA-RGD4C-yCD is 25.4±1.5 nM under simulated conditions. After challenged by the EDTA with a 10-fold molar excess of protein, the $K_d$ of In-DTPA-RGD4C-yCD is 34.6±5.4 nM, it still has good integrin $\alpha_v\beta_3$ receptor binding ability; Regardless of before and after modifying, marking and purifying DTPA, yCD can not be bound with integrin αvβ3 receptor. Although the two proteins after marking are greatly affected by the enzyme activity, they still have good binding ability to the integrin $\alpha_v\beta_3$ receptor. In consideration of the indispensability of EDTA for radiochemical purity, it retains a considerable amount of enzyme activity. In addition, the effect of integrin $\alpha_v\beta_3$ receptor binding ability is minimal, in combination of cell uptake, biodistribution and angiography experiment, focusing on the evaluation of target results, and the subsequent biological experiment is still carried out by the marking and purification conditions.

TABLE 17 yCD series protein enzyme kinetic parameters $V_{max}$ and $K_m$ after DTPA modification, marking and purification

| Protein | $V_{max}$ (µM/min) | $K_m$ (µM) |
|---|---|---|
| yCD | 264.1 ± 8.256 | 839.8 ± 71.94 |
| DTPA-yCD | 286.8 ± 10.80 | 1038 ± 96.19 |
| In- DTPA-yCD | 270.0 ± 6.165 | 1125 ± 58.72 |
| In- DTPA-yCD 10x EDTA | 125.2 ± 9.652 | 1932 ± 286.1 |
| RGD4C-yCD | 288.7 ± 8.883 | 1004 ± 73.19 |
| DTPA- RGD4C-yCD | 224.6 ± 8.408 | 1163 ± 107.8 |
| In-DTPA- RGD4C-yCD | 226.8 ± 6.918 | 956.4 ± 76.79 |
| In-DTPA- RGD4C-yCD 10x EDTA | 117.7 ± 9.510 | 1627 ± 273.1 |

Note:
$V_{max}$ is the maximum initial velocity of the enzyme; $K_m$ is the concentration of the substrate required to reach half of $V_{max}$.

TABLE 18

Binding ability parameters of yCD series protein and integrin $\alpha_v\beta_3$ receptor after DTPA modification, marking and purification

| Protein | $K_d$ (nM) |
|---|---|
| yCD | N/A |
| DTPA-yCD | N/A |
| In- DTPA-yCD | N/A |
| In- DTPA-yCD 10x EDTA | N/A |
| RGD4C-yCD | 20.7 ± 2.2 |
| DTPA- RGD4C-yCD | 47.6 ± 5.9 |
| In-DTPA- RGD4C-yCD | 25.4 ± 1.5 |
| In-DTPA- RGD4C-yCD 10x EDTA | 34.6 ± 5.4 |

Note:
$K_d$ is the protein concentration required to reach half of $B_{max}$.

Figure 26:
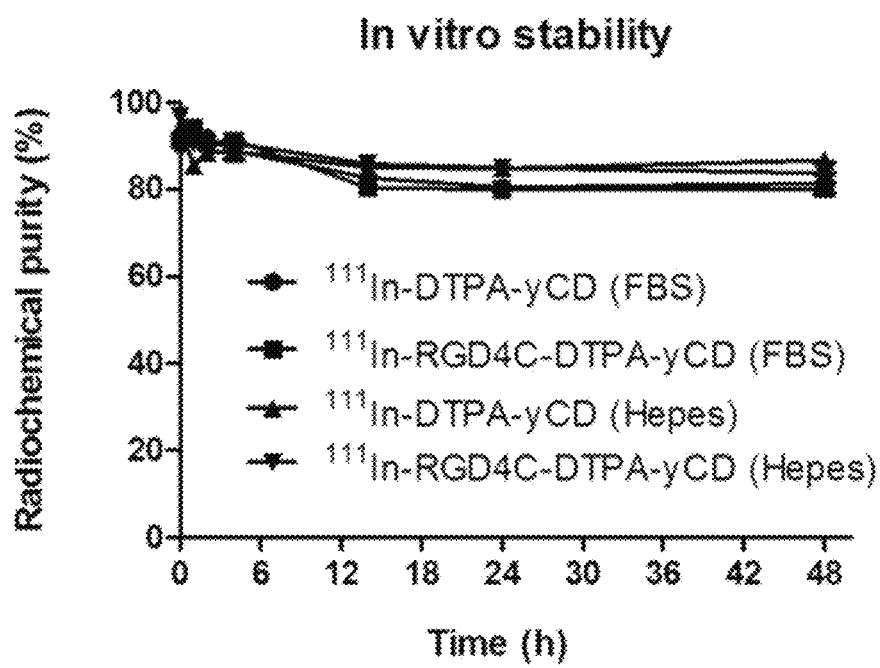
FIG. 26 shows the stability of $^{111}$In-DTPA-yCD and $^{111}$In-DTPA-RGD4C-yCD in HEPES buffer solution (4° C.) and fetal bovine serum (37° C.), part of the samples are respectively taken for radiochemical purity analysis at 1, 2, 4, 14, 24 and 48 hours.

22. In-Vitro Radiochemical Stability Test of In-DTPA-yCD and $^{111}$In-DTPA-RGD4C-yCD The radiochemical purity of $^{111}$In-DTPA-yCD and $^{111}$In-DTPA-RGD4C-yCD are greater than 95% after marking and purification. Both are stored in HEPES buffer liquid (4° C.) for 48 hours, and the radiochemical purity is still higher than 85% (see FIG. 26). Both are placed in fetal bovine serum (37° C.) to simulate their stability in vivo. After 48 hours, the radiochemical purity of both is about 80%. It is shown that radioactive metal indium-111 is stably chelated on DTPA.

23. Identification of Integrin Expression Amount in Different Cell Strains

Figure 27:
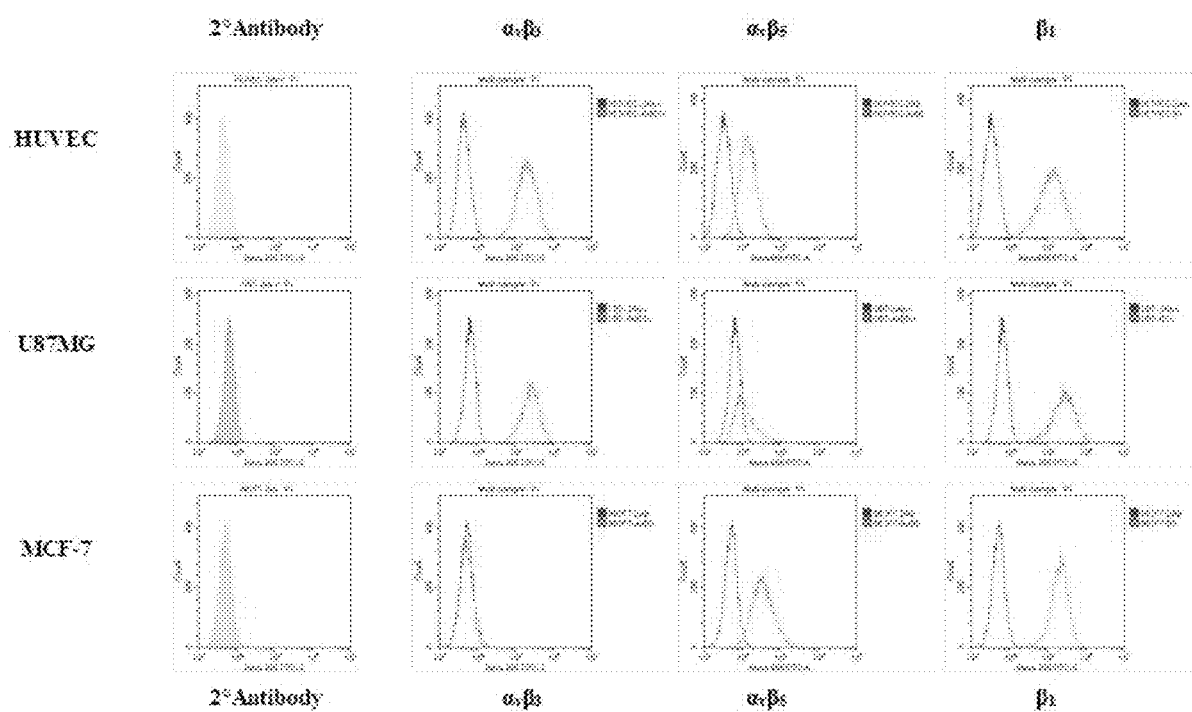
FIG. 27 shows the integrin expression level of different cell lines that identified by using flow cytometry. HUVEC and U87MG show high expression amount of integrin $\alpha_v\beta_3$, MCF-7 shows low expression level; MCF-7 shows moderate expression level of integrin $\alpha_v\beta_5$, HUVEC and U87MG show less expression level; all of three cell lines show a great expression level of integrin $\beta_1$.

Referring to FIG. 27, the three cells are the high-expression or low-expression cell strains of integrin $\alpha_v\beta_3$ frequently mentioned in the literature. HUVEC is the normal cell of human umbilical vein epithelium (high expression), and U87MG is human glioma cell strain (high expression). MCF-7 is a human breast adenoma cell (low expression). In order to know the integrin expression amount of other types, the flow cytometry is used to identify the expression amount of integrin $α_vβ_3$, integrin $α_vβ_5$ and integrin $β_1$ on three cells. The integrin $α_vβ_3$ expression amount of HUVEC and U87MG is high, MCF-7 has no expression; MCF-7 moderately expresses the integrin $α_vβ_5$, HUVEC and U87MG show less expression amount; all three cells greatly express the integrin $β_1$.

Figure 28:
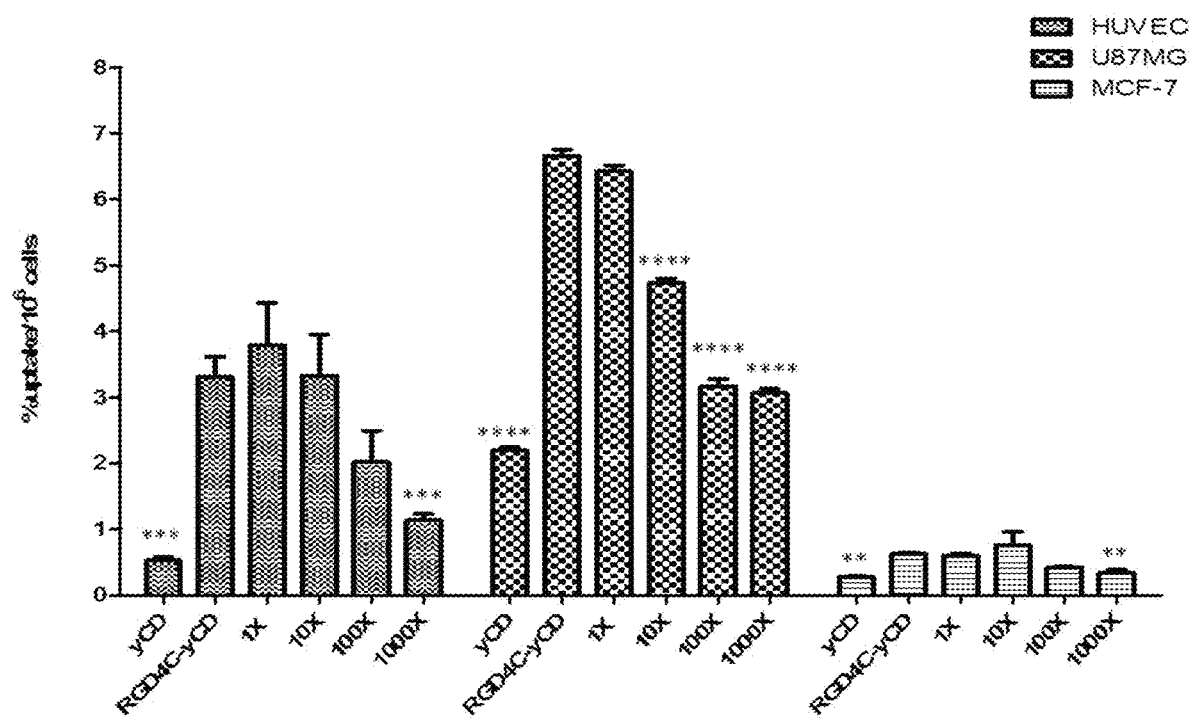
FIG. 28 shows a competitive cell uptake experiment of $^{111}$In-DTPA-yCD and $^{111}$In-DTPA-RGD4C-yCD in integrin $\alpha_v\beta_3$ high expressed (HUVEC, U87MG) or low expressed (MCF-7) cells. The uptake of $^{111}$In-DTPA-RGD4C-yCD in HUVEC and U87MG cells (high integrin $\alpha_v\beta_3$ expression) is significantly higher than that of MCF-7 (low integrin $\alpha_v\beta_3$ expression). The uptake of $^{111}$In-DTPA-yCD is low in the all three cell lines. After adding cRGDfk with a 1000-fold molar excess of protein, the uptake of $^{111}$In-DTPA-RGD4C-yCD in HUVEC, U87MG and MCF-7 cells is respectively decreased by about 65%, 55% and 45%. The decreased part after competition indicated that $^{111}$In-DTPA-RGD4C-yCD is specifically bound with the integrin receptor on the cell membrane. The uptake amount of $^{111}$In-DTPA-RGD4C-yCD by each cell strain is used as a control group, and analyzed by two sample t-test statistical methods, *P-value<0.05, P-value<0.01, *P-value<0.001, ****P-value<0.0001.

24. Competitive Cell Uptake Results of $^{111}$In-DTPA-yCD and $^{111}$In-DTPA-RGD4C-yCD by Different Integrin $α_vβ_3$ Expression Cells $^{111}$In-DTPA-yCD and $^{111}$In-DTPA-RGD4C-yCD (20 μCi/50 pmol/mL) are separately added to the 24-well plate of the seeded cells ($2.5×10^5$ cells/well) and cultured for 4 hours, and then the radioactivity of the cells and culture medium are separately measured, calculate the uptake amount of the drug by the cells (shown as % AD/$10^6$ cells). The uptake amount of HUVEC and U87MG cells of high expression integrin $α_vβ_3$ to $^{111}$In-DTPA-RGD4C-yCD is significantly higher than that of $^{111}$In-DTPA-yCD, although MCF-7 cells of integrin $α_vβ_3$ low expression have significant difference on uptake amount of both drugs, but its drug uptake amount is the lowest among the three cells (see FIG. 28). In the competitive cell uptake assay, $^{111}$In-DTPA-RGD4C-yCD (20 μCi/50 pmol/mL) is mixed with cRGDfk of the 1-fold, 10-fold, 100-fold or 1000-fold molar excess of protein, and cultured in 24-well plate added with the seeded cells ($2.5×10^5$ cells/well) for 4 hours, the results show that the uptake amount of $^{111}$In-DTPA-RGD4C-yCD by HUVEC and U87MG cells with high expression of integrin $α_vβ_3$ is gradually decreased along with the increase of the molar excess of the competitor cRGDfk, the uptake amount of $^{111}$In-DTPA-RGD4C-yCD by MCF-7 with low expression of integrin $α_vβ_3$ has no significant decrease. After adding the competition of cRGDfk with 1000-fold molar excess of protein, the uptake amount of $^{111}$In-DTPA-RGD4C-yCD by HUVEC, U87MG and MCF-7 cells is decreased by about 65%, 55% and 45% respectively (see FIG. 28), the decreased part after competition is the specific binding of $^{111}$In-DTPA-RGD4C-yCD and the integrin receptor on the cell.

25. Identification of Integrin Expression Amount in Ovarian Cancer Cells

Figure 29:
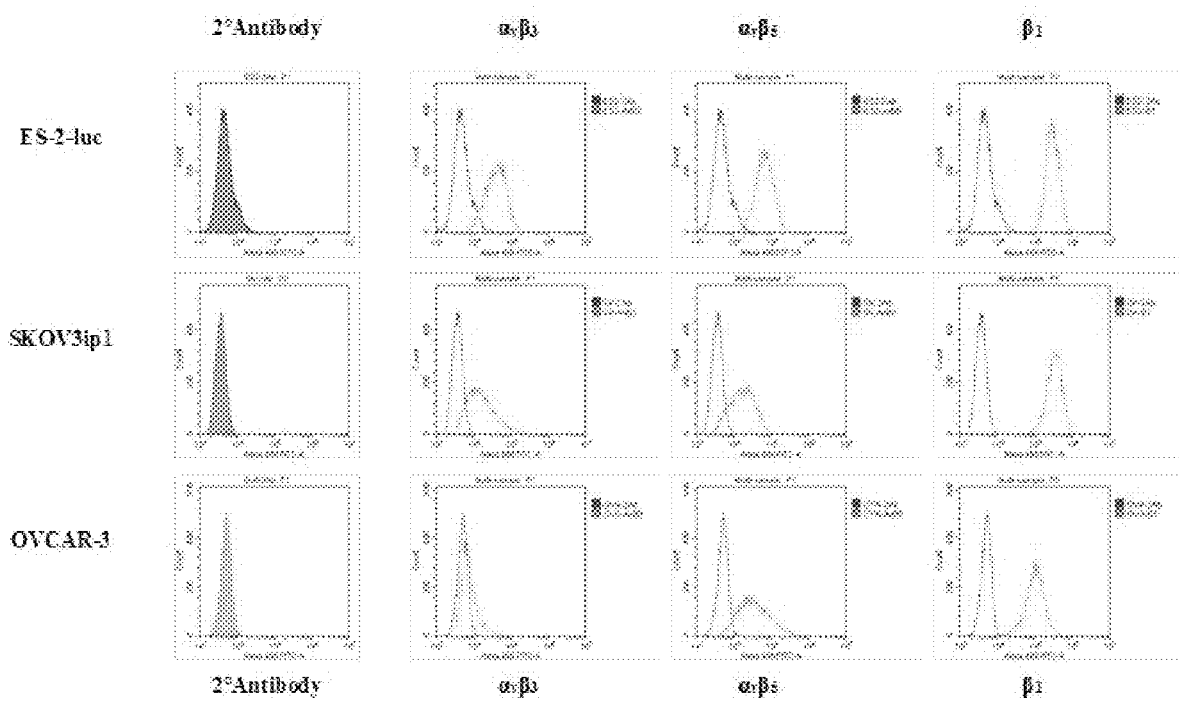
FIG. 29 shows the expression amount of integrin in different ovarian cancer cells that identified by flow cytometry. ES-2-luc and SKOV3ip1 express the integrin $\alpha_v\beta_3$ moderately and slightly, and OVCAR-3 shows no expression amount; ES-2-luc and OVCAR-3 moderately express the integrin $\alpha_v\beta_5$, SKOV3ip1 has less expression amount; all three cell strains have a great expression amount of integrin $\beta_1$.

The three cells are of the ovarian cancer cells as shown in FIG. 29. In order to screen out the cell strain with high expression amount of integrin, the expression amount of integrin $α_vβ_3$, integrin $α_vβ_5$ and integrin $β_1$ on the three cells is identified by flow cytometry. ES-2-luc and SKOV3ip1 express the integrin $α_vβ_3$ moderately and slightly, and OVCAR-3 has no expression; ES-2-luc and OVCAR-3 moderately expresses integrin $α_vβ_5$, SKOV3ip1 has less expression; all three cells greatly express integrin $β_1$. By summing the integrin expression amount of all kinds, the screened ES-2-luc is the cell strain of ovarian cancer peritoneal metastasis.

Figure 30:
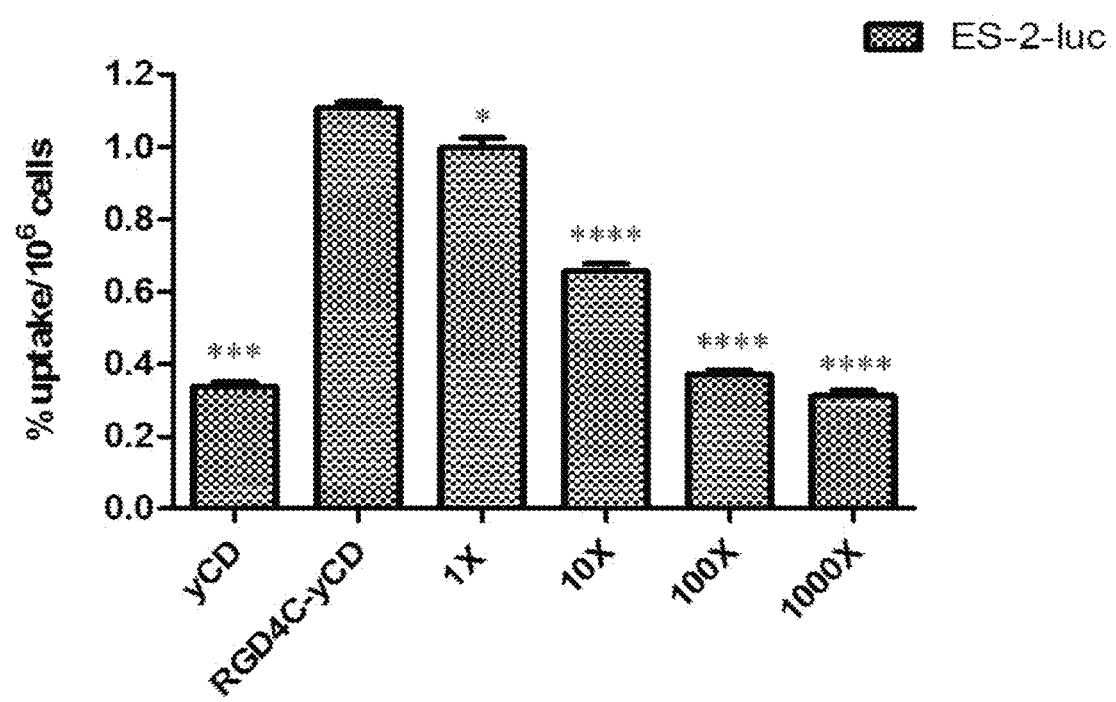
FIG. 30 shows a competitive cell uptake assay of $^{111}$In-DTPA-yCD and $^{111}$In-DTPA-RGD4C-yCD in ES-2-luc cells (moderate integrin $\alpha_v\beta_3$ expression). The uptake of $^{111}$In-DTPA-yCD and $^{111}$In-DTPA-RGD4C-yCD in ES-2-luc cells is significantly different. After adding cRGDfk with a 1000-fold molar excess of protein, the uptake of $^{111}$In-DTPA-RGD4C-yCD in ES-2-luc cells is decreased by about 70%. The decreased part after competition indicated that the $^{111}$In-DTPA-RGD4C-yCD is specifically bound with the integrin receptor on the cell membrane. The uptake amount of $^{111}$In-DTPA-RGD4C-yCD by cell is used as a control group, and analyzed by two sample t-test statistical methods, *P-value<0.05, P-value<0.01, *P-value<0.001, ****P-value<0.0001.

26. Competitive Cell Uptake Assay of $^{111}$In-DTPA-yCD and $^{111}$In-DTPA-RGD4C-yCD by ES-2-luc Cells $^{11}$In-DTPA-yCD and $^{111}$In-DTPA-RGD4C-yCD (20 μCi/50 pmol/mL) are separately added to a 24-well plate of the seeded ES-2-luc cells ($2.5×10^5$ cells/well) for 4 hours, and then the radioactivity in cells and culture medium is measured separately, and the uptake amount of the drug by the cells is calculated (shown as % AD/$10^6$ cells). The uptake amount of $^{111}$In-DTPA-RGD4C-yCD by cells is significantly higher than that of $^{111}$In-DTPA-yCD (see FIG. 30). In competitive cell uptake experiment, $^{111}$In-DTPA-RGD4C-yCD (20 μCi/) 50 pmol/mL) is mixed with cRGDfk of the 1-fold, 10-fold, 100-fold or 1000-fold molar excess of protein, and cultured in 24-well plate added with the seeded cells ($2.5×10^5$ cells/well) for 4 hours. The results show that the uptake amount of $^{111}$In-DTPA-RGD4C-yCD by ES-2-luc cells is gradually decreased along with the increase of the molar excess of the competitor cRGDfk. After adding the competition of cRGDfk with with a 1000-fold molar excess of protein, the uptake amount of $^{111}$In-DTPA-RGD4C-yCD by ES-2-luc cells is decreased by about 70% (see FIG. 30), the decreased part after competition is the specific binding of $^{111}$In-DTPA-RGD4C-yCD and the integrin receptor on the cell.

Figure 31:
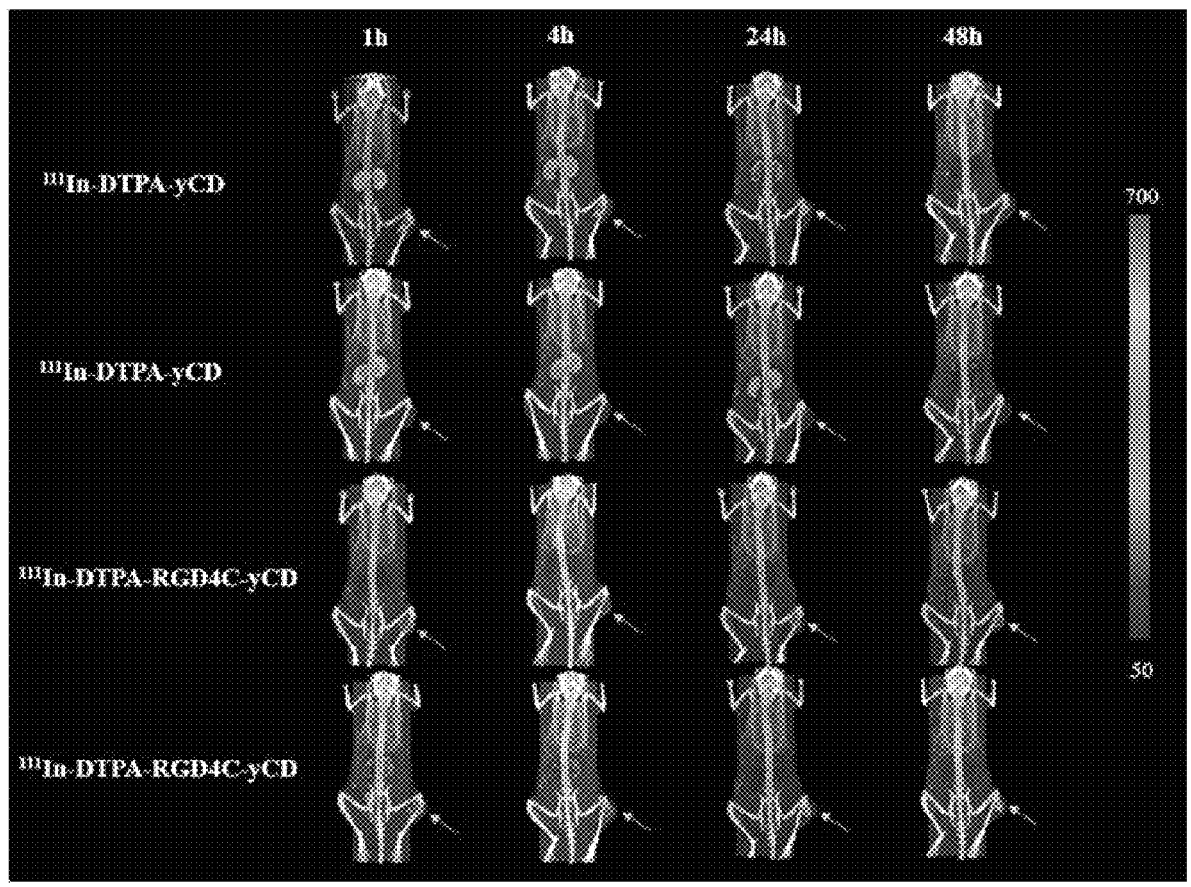
FIG. 31 shows microSPECT/CT angiography at 1, 4, 24 and 48 hours after intratumoral injection of $^{111}$In-DTPA-yCD and $^{111}$In-DTPA-RGD4C-yCD in U87MG tumor-bearing nude mice. The arrow is marked as a tumor.

27. Intratumoral Injection of $^{111}$in-DTPA-yCD and $^{111}$in-DTPA-RGD4C-yCD into U87MG Tumor Nude Mice was Performed by Single-Photon and Computed Tomography In in-vitro cell experiment, the binding ability of $^{111}$In-DTPA-RGD4C-yCD and the integrin $α_vβ_3$ receptor on the cell membrane has been verified. In order to know whether the drug can show its target effect in vivo, integrin $α_vβ_3$ is seeded subcutaneously in the right side of nude mice. After the high-expression U87MG tumor cells are grown to 100 mm$^3$, 60-70 μCi (3-3.5 μg) of $^{111}$In-DTPA-yCD and $^{111}$In-DTPA-RGD4C-yCD are injected directly into the tumor, the images are collected by microSPECT/CT after 1, 4, 24, 48 hours. It can be seen from the image (see FIG. 31) that the drug retention in the $^{111}$In-DTPA-RGD4C-yCD group (orange arrow) is better than that in the $^{111}$In-DTPA-yCD, and the target ligand RGD4C is missing. $^{111}$In-DTPA-yCD enters the systemic blood circulation system within 1 hour and is metabolized by normal organs. From FIG. 31, it can be seen that the kidney is the main metabolic organ of these two drugs. The amount of $^{111}$In-DTPA-yCD accumulated in the tumor is gradually decreased with time. After 24-48 hours, the amount of accumulation in the tumor is running out. On the contrary, $^{111}$In-DTPA-RGD4C-yCD is bound with integrin αvβ3 on tumor cells, then the ratio of drug entering the systemic blood circulation is reduced, and the metabolic rate is slow. At $48^{th}$ hour, there is still considerable drug accumulation in the tumor.

28. Biodistribution Experiment of Intraperitoneal Injection of $^{111}$In-DTPA-yCD and $^{111}$In-DTPA-RGD4C-yCD in ES-2-luc Tumor Nude Mice ES-2-luc tumor nude mice is intraperitoneally injected with 50 μCi (2.5 μg) $^{111}$In-DTPA-yCD and $^{111}$In-DTPA-RGD4C-yCD for 1, 4 and 24 hours, then organs are collected and their radioactivity is measured to obtain biodistribution, as shown in Table 19 and Table 20. It can be seen from the results that the radioactivity of $^{111}$In-DTPA-yCD and $^{111}$In-DTPA-RGD4C-yCD in the peritoneal cavity is decreased rapidly with time, and there are 2.18±0.62% ID and 4.20±1.05% ID at 1 hour after injection, which has been reduced to ½ and ¼ in 4 hours after injection, which shows that the drug stays in the abdominal cavity for a short time. $^{111}$In-DTPA-yCD and $^{111}$In-DTPA-RGD4C-yCD are injected in the abdominal cavity, a part is accumulated on tumor cells after 1 hour, the radioactivity is 10.50±3.57% ID/g and 24.32±2.58% ID/g respectively. After 4 hours, the radioactivity of $^{111}$In-DTPA-RGD4C-yCD in tumor is approximately 3 times higher than that of $^{111}$In-DTPA-yCD (10.48±4.33% ID/g), which indicatinges that $^{111}$In-DTPA-RGD4C-yCD is assuredly bound with integrin $α_vβ_3$ on tumor cells; after 24 hours, the accumulation amount of both drugs in tumor cells is decreased. In addition to the part accumulated in the tumor, another part of the drug is absorbed back into the blood circulation system by the peritoneal blood vessels. After 1 hour of injection of $^{111}$In-DTPA-yCD and $^{111}$In-DTPA-RGD4C-yCD, the radioactivity in the kidney is 55.73±3.57% ID/g and 48.60±2.98% ID/g respectively, it is maintained at 50~60% ID/g after 24 hours of injection, which indicates that once the two drugs return to the blood, they are quickly metabolized by the kidneys; after 24 hours of injection, the blood radioactivity is less than 1% ID/g. When the organs are collected, it is found that the appearance of the pancreas is erosive and swollen. The pancreatic radioactivity of the two drugs is observed after 1 hour of injection. The pancreatic radioactivity of $^{111}$In-DTPA-RGD4C-yCD (8.06±0.88% ID/g) is higher than that of $^{111}$In-DTPA-yCD (3.91±0.36% ID/g), it is suspected that tumor cells invade the pancreas.

TABLE 19

Biodistribution of ES-2-luc tumor nude mice after intraperitoneal injection of $^{111}$In-DTPA-yCD

|  | 1 hour | 4 hours | 24 hours |
| --- | --- | --- | --- |
| Blood | 1.07 ± 0.20 | 1.30 ± 0.74 | 0.28 ± 0.23 |
| Heart | 0.57 ± 0.07 | 0.51 ± 0.05 | 0.51 ± 0.01 |
| Lung | 1.19 ± 0.25 | 0.96 ± 0.25 | 1.18 ± 0.30 |
| Liver | 4.27 ± 0.91 | 4.22 ± 0.31 | 3.51 ± 0.21 |
| Stomach | 2.27 ± 0.61 | 2.31 ± 0.30 | 2.97 ± 0.04 |
| S. intestine | 2.39 ± 1.05 | 2.00 ± 0.44 | 1.98 ± 0.21 |
| L. intestine | 3.35 ± 0.76 | 3.54 ± 0.96 | 3.39 ± 2.17 |
| Pancreas | 3.91 ± 0.36 | 5.72 ± 0.57 | 3.82 ± 0.69 |
| Spleen | 2.43 ± 0.50 | 2.31 ± 0.30 | 2.97 ± 0.04 |
| Muscle | 0.29 ± 0.04 | 0.25 ± 0.05 | 0.21 ± 0.01 |
| Bone | 0.43 ± 0.10 | 0.45 ± 0.20 | 0.34 ± 0.18 |
| Bladder | 3.61 ± 0.80 | 5.35 ± 1.27 | 3.17 ± 0.96 |
| Kidney | 55.73 ± 3.57 | 47.40 ± 4.22 | 68.84 ± 6.61 |
| Urine | 75.03 ± 10.81 | 48.48 ± 34.28 | 17.17 ± 1.86 |
| Feces | 0.62 ± 0.63 | 1.94 ± 1.68 | 1.50 ± 0.65 |
| Tumor | 10.50 ± 3.57 | 10.48 ± 4.33 | 7.38 ± 0.47 |
| Ascites (% ID) | 2.18 ± 0.62 | 0.97 ± 0.15 | 0.13 ± 0.02 |

TABLE 20

Biodistribution of ES-2-luc tumor nude mice after intraperitoneal injection of $^{111}$In-DTPA- RGD4C-yCD

|  | 1 hour | 4 hours | 24 hours |
| --- | --- | --- | --- |
| Blood | 1.53 ± 0.87 | 1.07 ± 0.48 | 0.85 ± 0.32 |
| Heart | 0.44 ± 0.03 | 0.40 ± 0.01 | 0.35 ± 0.05 |
| Lung | 0.89 ± 017 | 0.94 ± 0.10 | 1.91 ± 0.54 |
| Liver | 4.77 ± 0.35 | 5.59 ± 0.17 | 3.71 ± 0.92 |
| Stomach | 2.31 ± 0.48 | 1.87 ± 0.24 | 1.84 ± 0.09 |
| S. intestine | 3.37 ± 0.80 | 3.05 ± 0.87 | 2.28 ± 0.53 |
| L. intestine | 2.73 ± 0.45 | 2.47 ± 0.12 | 1.87 ± 0.42 |
| Pancreas | 8.06 ± 0.88 | 6.85 ± 0.29 | 6.10 ± 0.70 |
| Spleen | 2.81 ± 0.61 | 2.89 ± 0.16 | 3.30 ± 0.40 |
| Muscle | 0.34 ± 0.15 | 0.23 ± 0.01 | 0.14 ± 0.03 |
| Bone | 0.30 ± 0.17 | 0.21 ± 0.15 | 0.13 ± 0.03 |
| Bladder | 3.03 ± 0.26 | 3.73 ± 0.87 | 3.52 ± 0.79 |
| Kidney | 48.60 ± 2.98 | 56.73 ± 0.02 | 51.16 ± 2.63 |
| Urine | 167.93 ± 16.37 | 70.60 ± 57.04 | 16.19 ± 5.47 |
| Feces | 1.32 ± 0.71 | 1.94 ± 0.27 | 1.00 ± 0.07 |
| Tumor | 24.32 ± 2.58 | 30.48 ± 9.64 | 17.63 ± 3.78 |
| Ascites (% ID) | 4.20 ± 1.05 | 0.70 ± 0.12 | 0.76 ± 0.22 |

The technical features of the invention disclosed in all specifications can be combined in any manner. Each of the technical features disclosed in the specifications can be replaced by other means of the same, equivalent or similar purpose. Therefore, unless otherwise stated, all the features disclosed herein are only the example of the general series of equivalent or similar features.

It is known from the above that those skilled in the art can readily understand the essential features of the present invention, and can make many changes and adjustments to the present invention for different uses and conditions without departing from the spirit and scope thereof.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A targeted prodrug enzyme fusion carrier for identifying and binding a tumor cell or/and an angiogenic endothelial cell of tumor tissues, and diagnosing and treating cancer, comprising a prodrug enzyme at least,
   wherein the prodrug enzyme is selected from the group consisting of yeast cytosine deaminase (yCD) (SEQ ID NO: 1), *E. coli.* cytosine deaminase (EcCD) (SEQ ID NO: 17), and EcCD_D314A (SEQ ID NO: 18),
   when the prodrug enzyme is yCD (SEQ ID NO: 1), the targeted prodrug enzyme fusion carrier is consisting of RGD4C-yCD (SEQ ID NO: 3) and RGD4C_yCD_yUPRT (SEQ ID NO: 4),
   when the prodrug enzyme is EcCD (SEQ ID NO: 17), the targeted prodrug enzyme fusion carrier is consisting of RGD4C_EcCD_WT (SEQ ID NO: 19),
   when the prodrug enzyme is EcCD_D314A (SEQ ID NO: 18), the targeted prodrug enzyme fusion carrier is consisting of RGD4C_EcCD_D314A (SEQ ID NO: 20),
   wherein the targeted prodrug enzyme fusion carrier can convert a 5-fluorocytosine (5-FC) into a 5-fluorouracil (5-FU),
   wherein the targeted prodrug enzyme fusion carrier is administered a therapeutically effective amount to a subject in need thereof, wherein the subject is diagnosed with cancer.

2. A targeted prodrug enzyme fusion carrier for identifying and binding a tumor cell or/and an angiogenic endothelial cell of tumor tissues, and diagnosing and treating cancer, comprising at least a prodrug enzyme, wherein the prodrug enzyme is selected from the group consisting of yeast cytosine deaminase (yCD) (SEQ ID NO: 1), *E. coli.* cytosine deaminase (EcCD) (SEQ ID NO: 17), and EcCD_D314A (SEQ ID NO: 18),
   when the prodrug enzyme is yCD (SEQ ID NO: 1), the targeted prodrug enzyme fusion carrier is selected from the group consisting of RGD_EGF_yCD (SEQ ID NO: 5), RGD4C_EGF_yCD (SEQ ID NO: 7), yCD_RGD_EGF (SEQ ID NO: 9), yCD_RGD4C_EGF (SEQ ID NO: 11), RGD_VEGF_yCD (SEQ ID NO: 13), RGD4C_VEGF_yCD (SEQ ID NO: 15), RGD_EGF_yCD_yUPRT (SEQ ID NO: 6), RGD4C_EGF_yCD_yUPRT (SEQ ID NO: 8), yCD_yUPRT_RGD_EGF (SEQ ID NO: 10), yCD_yUPRT_RGD4C_EGF (SEQ ID NO: 12), RGD_VEGF_yCD_yUPRT (SEQ ID NO: 14), and RGD4C_VEGF_yCD_yUPRT (SEQ ID NO: 16),
   when the prodrug enzyme is EcCD (SEQ ID NO: 17), the targeted prodrug enzyme fusion carrier is further selected from the group consisting of RGD_EGF_EcCD_WT (SEQ ID NO: 21), RGD4C_EGF_EcCD_WT (SEQ ID NO: 23), EcCD_WT_RGD_EGF (SEQ ID NO: 25), EcCD_WT_RGD4C_EGF (SEQ ID NO: 27), RGD_VEGF_EcCD_WT (SEQ ID NO: 29), RGD4C_VEGF_EcCD_WT (SEQ ID NO: 31),
   when the prodrug enzyme is EcCD_D314A (SEQ ID NO: 18), the targeted prodrug enzyme fusion carrier is further selected from the group consisting of RGD_EGF_EcCD_D314A (SEQ ID NO: 22), RGD4C_EGF_EcCD_D314A (SEQ ID NO: 24), EcCD_D314A_RGD_EGF (SEQ ID NO: 26), EcCD_D314A_RGD4C_EGF (SEQ ID NO: 28), RGD_VEGF_EcCD_D314A (SEQ ID NO: 30), and RGD4C_VEGF_EcCD_D314A (SEQ ID NO: 32),
   wherein the targeted prodrug enzyme fusion carrier can convert a 5-fluorocytosine (5-FC) into a 5-fluorouracil (5-FU),
   wherein the targeted prodrug enzyme fusion carrier is administered a therapeutically effective amount to a subject in need thereof, wherein the subject is diagnosed with cancer.

3. The targeted prodrug enzyme fusion carrier according to claim 1, further comprises a marker molecule.

4. The targeted prodrug enzyme fusion carrier according to claim 3, wherein the marker molecule is selected from the group consisting of a radionuclide and a fluorescent protein.

5. The targeted prodrug enzyme fusion carrier according to claim 4, wherein the radionuclide is selected from the indium-111 ($^{111}$In), gallium-67, gallium-68, yttrium-90 and lutetium-177.

6. The targeted prodrug enzyme fusion carrier according to claim 5, further comprises a metal chelating agent.

7. The targeted prodrug enzyme fusion carrier according to claim 6, wherein the metal chelating agent is selected from the group consisting of DTPA, NOTA and DOTA.

8. The targeted prodrug enzyme fusion carrier according to claim 7, wherein the molar ratio of the prodrug enzyme and the metal chelating agent is less than 20%.

9. A kit comprising the targeted prodrug enzyme fusion carrier of claim 1 and a prodrug, wherein the prodrug is 5 fluorocytosine (5-FC).

* * * * *

SEQUENCE LISTING

<160> NUMBER OF SEQ ID NOS: 32

<210> SEQ ID NO 1
<211> LENGTH: 167
<212> TYPE: PRT
<213> ORGANISM: Artificial Sequence
<220> FEATURE:
<223> OTHER INFORMATION: yCD

<400> SEQUENCE: 1

Met Val Val Thr Gly Gly Met Ala Ser Lys Trp Asp Gln Lys Gly Met
1               5                   10                  15

Asp Ile Ala Tyr Glu Glu Ala Ala Leu Gly Tyr Lys Glu Gly Gly Val
                20                  25                  30

Pro Ile Gly Gly Cys Leu Ile Asn Asn Lys Asp Gly Ser Val Leu Gly
                35                  40                  45

Arg Gly His Asn Met Arg Phe Gln Lys Gly Ser Ala Thr Leu His Gly
            50                  55                  60

Glu Ile Ser Thr Leu Glu Asn Cys Gly Arg Leu Glu Gly Lys Val Tyr
65                  70                  75                  80

Lys Asp Thr Thr Leu Tyr Thr Thr Leu Ser Pro Cys Asp Met Cys Thr
                85                  90                  95

```
Gly Ala Ile Ile Met Tyr Gly Ile Pro Arg Cys Val Val Gly Glu Asn
                100                 105                 110

Val Asn Phe Lys Ser Lys Gly Glu Lys Tyr Leu Gln Thr Arg Gly His
                115                 120                 125

Glu Val Val Val Asp Asp Glu Arg Cys Lys Lys Ile Met Lys Gln
130                 135                 140

Phe Ile Asp Glu Arg Pro Gln Asp Trp Phe Glu Asp Ile Gly Glu Leu
145                 150                 155                 160

Glu His His His His His
                165
```

<210> SEQ ID NO 2
<211> LENGTH: 382
<212> TYPE: PRT
<213> ORGANISM: Artificial Sequence
<220> FEATURE:
<223> OTHER INFORMATION: yCD_yUPRT
<400> SEQUENCE: 2

```
Met Val Val Thr Gly Gly Met Ala Ser Lys Trp Asp Gln Lys Gly Met
1               5                   10                  15

Asp Ile Ala Tyr Glu Glu Ala Ala Leu Gly Tyr Lys Glu Gly Gly Val
                20                  25                  30

Pro Ile Gly Gly Cys Leu Ile Asn Asn Lys Asp Gly Ser Val Leu Gly
                35                  40                  45

Arg Gly His Asn Met Arg Phe Gln Lys Gly Ser Ala Thr Leu His Gly
            50                  55                  60

Glu Ile Ser Thr Leu Glu Asn Cys Gly Arg Leu Glu Gly Lys Val Tyr
65                  70                  75                  80

Lys Asp Thr Thr Leu Tyr Thr Thr Leu Ser Pro Cys Asp Met Cys Thr
                85                  90                  95

Gly Ala Ile Ile Met Tyr Gly Ile Pro Arg Cys Val Val Gly Glu Asn
                100                 105                 110

Val Asn Phe Lys Ser Lys Gly Glu Lys Tyr Leu Gln Thr Arg Gly His
                115                 120                 125

Glu Val Val Val Asp Asp Glu Arg Cys Lys Lys Ile Met Lys Gln
130                 135                 140

Phe Ile Asp Glu Arg Pro Gln Asp Trp Phe Glu Asp Ile Gly Glu Ala
145                 150                 155                 160

Ser Glu Pro Phe Lys Asn Val Tyr Leu Leu Pro Gln Thr Asn Gln Leu
                165                 170                 175

Leu Gly Leu Tyr Thr Ile Ile Arg Asn Lys Asn Thr Thr Arg Pro Asp
                180                 185                 190

Phe Ile Phe Tyr Ser Asp Arg Ile Ile Arg Leu Leu Val Glu Glu Gly
                195                 200                 205

Leu Asn His Leu Pro Val Gln Lys Gln Ile Val Glu Thr Asp Thr Asn
                210                 215                 220

Glu Asn Phe Glu Gly Val Ser Phe Met Gly Lys Ile Cys Gly Val Ser
225                 230                 235                 240

Ile Val Arg Ala Gly Glu Ser Met Glu Gln Gly Leu Arg Asp Cys Cys
                245                 250                 255

Arg Ser Val Arg Ile Gly Lys Ile Leu Ile Gln Arg Asp Glu Glu Thr
                260                 265                 270

Ala Leu Pro Lys Leu Phe Tyr Glu Lys Leu Pro Glu Asp Ile Ser Glu
                275                 280                 285
```

```
Arg Tyr Val Phe Leu Leu Asp Pro Met Leu Ala Thr Gly Gly Ser Ala
        290                 295                 300

Ile Met Ala Thr Glu Val Leu Ile Lys Arg Gly Val Lys Pro Glu Arg
305                 310                 315                 320

Ile Tyr Phe Leu Asn Leu Ile Cys Ser Lys Glu Gly Ile Glu Lys Tyr
                325                 330                 335

His Ala Ala Phe Pro Glu Val Arg Ile Val Thr Gly Ala Leu Asp Arg
                340                 345                 350

Gly Leu Asp Glu Asn Lys Tyr Leu Val Pro Gly Leu Gly Asp Phe Gly
            355                 360                 365

Asp Arg Tyr Tyr Cys Val Leu Glu His His His His His His
        370                 375                 380
```

<210> SEQ ID NO 3
<211> LENGTH: 176
<212> TYPE: PRT
<213> ORGANISM: Artificial Sequence
<220> FEATURE:
<223> OTHER INFORMATION: RGD4C_yCD

<400> SEQUENCE: 3

```
Met Ala Cys Asp Cys Arg Gly Asp Cys Phe Cys Val Thr Gly Gly Met
1               5                   10                  15

Ala Ser Lys Trp Asp Gln Lys Gly Met Asp Ile Ala Tyr Glu Glu Ala
            20                  25                  30

Ala Leu Gly Tyr Lys Glu Gly Gly Val Pro Ile Gly Gly Cys Leu Ile
        35                  40                  45

Asn Asn Lys Asp Gly Ser Val Leu Gly Arg Gly His Asn Met Arg Phe
50                  55                  60

Gln Lys Gly Ser Ala Thr Leu His Gly Glu Ile Ser Thr Leu Glu Asn
65                  70                  75                  80

Cys Gly Arg Leu Glu Gly Lys Val Tyr Lys Asp Thr Thr Leu Tyr Thr
                85                  90                  95

Thr Leu Ser Pro Cys Asp Met Cys Thr Gly Ala Ile Ile Met Tyr Gly
            100                 105                 110

Ile Pro Arg Cys Val Val Gly Glu Asn Val Asn Phe Lys Ser Lys Gly
        115                 120                 125

Glu Lys Tyr Leu Gln Thr Arg Gly His Glu Val Val Val Asp Asp
    130                 135                 140

Glu Arg Cys Lys Lys Ile Met Lys Gln Phe Ile Asp Glu Arg Pro Gln
145                 150                 155                 160

Asp Trp Phe Glu Asp Ile Gly Glu Leu Glu His His His His His His
                165                 170                 175
```

<210> SEQ ID NO 4
<211> LENGTH: 391
<212> TYPE: PRT
<213> ORGANISM: Artificial Sequence
<220> FEATURE:
<223> OTHER INFORMATION: RGD4C_yCD_yUPRT

<400> SEQUENCE: 4

```
Met Ala Cys Asp Cys Arg Gly Asp Cys Phe Cys Val Thr Gly Gly Met
1               5                   10                  15

Ala Ser Lys Trp Asp Gln Lys Gly Met Asp Ile Ala Tyr Glu Glu Ala
            20                  25                  30

Ala Leu Gly Tyr Lys Glu Gly Gly Val Pro Ile Gly Gly Cys Leu Ile
```

```
                35                  40                  45
Asn Asn Lys Asp Gly Ser Val Leu Gly Arg Gly His Asn Met Arg Phe
 50                  55                  60

Gln Lys Gly Ser Ala Thr Leu His Gly Glu Ile Ser Thr Leu Glu Asn
 65                  70                  75                  80

Cys Gly Arg Leu Glu Gly Lys Val Tyr Lys Asp Thr Thr Leu Tyr Thr
                 85                  90                  95

Thr Leu Ser Pro Cys Asp Met Cys Thr Gly Ala Ile Ile Met Tyr Gly
                100                 105                 110

Ile Pro Arg Cys Val Val Gly Glu Asn Val Asn Phe Lys Ser Lys Gly
                115                 120                 125

Glu Lys Tyr Leu Gln Thr Arg Gly His Glu Val Val Val Asp Asp
    130                 135                 140

Glu Arg Cys Lys Lys Ile Met Lys Gln Phe Ile Asp Glu Arg Pro Gln
145                 150                 155                 160

Asp Trp Phe Glu Asp Ile Gly Glu Ala Ser Glu Pro Phe Lys Asn Val
                165                 170                 175

Tyr Leu Leu Pro Gln Thr Asn Gln Leu Leu Gly Leu Tyr Thr Ile Ile
                180                 185                 190

Arg Asn Lys Asn Thr Thr Arg Pro Asp Phe Ile Phe Tyr Ser Asp Arg
                195                 200                 205

Ile Ile Arg Leu Leu Val Glu Glu Gly Leu Asn His Leu Pro Val Gln
                210                 215                 220

Lys Gln Ile Val Glu Thr Asp Thr Asn Glu Asn Phe Glu Gly Val Ser
225                 230                 235                 240

Phe Met Gly Lys Ile Cys Gly Val Ser Ile Val Arg Ala Gly Glu Ser
                245                 250                 255

Met Glu Gln Gly Leu Arg Asp Cys Cys Arg Ser Val Arg Ile Gly Lys
                260                 265                 270

Ile Leu Ile Gln Arg Asp Glu Glu Thr Ala Leu Pro Lys Leu Phe Tyr
                275                 280                 285

Glu Lys Leu Pro Glu Asp Ile Ser Glu Arg Tyr Val Phe Leu Leu Asp
                290                 295                 300

Pro Met Leu Ala Thr Gly Gly Ser Ala Ile Met Ala Thr Glu Val Leu
305                 310                 315                 320

Ile Lys Arg Gly Val Lys Pro Glu Arg Ile Tyr Phe Leu Asn Leu Ile
                325                 330                 335

Cys Ser Lys Glu Gly Ile Glu Lys Tyr His Ala Ala Phe Pro Glu Val
                340                 345                 350

Arg Ile Val Thr Gly Ala Leu Asp Arg Gly Leu Asp Glu Asn Lys Tyr
                355                 360                 365

Leu Val Pro Gly Leu Gly Asp Phe Gly Asp Arg Tyr Tyr Cys Val Leu
                370                 375                 380

Glu His His His His His His
385                 390

<210> SEQ ID NO 5
<211> LENGTH: 228
<212> TYPE: PRT
<213> ORGANISM: Artificial Sequence
<220> FEATURE:
<223> OTHER INFORMATION: RGD_EGF_yCD

<400> SEQUENCE: 5

Met Ala Arg Gly Asp Asn Ser Asp Ser Glu Cys Pro Leu Ser His Asp
```

```
1               5                   10                  15
Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
            35                  40                  45

Tyr Arg Asp Leu Lys Trp Trp Glu Leu Arg Pro Gly Gly Gly Gly Val
        50                  55                  60

Thr Gly Gly Met Ala Ser Lys Trp Asp Gln Lys Gly Met Asp Ile Ala
65                  70                  75                  80

Tyr Glu Glu Ala Ala Leu Gly Tyr Lys Glu Gly Val Pro Ile Gly
                85                  90                  95

Gly Cys Leu Ile Asn Asn Lys Asp Gly Ser Val Leu Gly Arg Gly His
            100                 105                 110

Asn Met Arg Phe Gln Lys Gly Ser Ala Thr Leu His Gly Glu Ile Ser
            115                 120                 125

Thr Leu Glu Asn Cys Gly Arg Leu Glu Gly Lys Val Tyr Lys Asp Thr
130                 135                 140

Thr Leu Tyr Thr Thr Leu Ser Pro Cys Asp Met Cys Thr Gly Ala Ile
145                 150                 155                 160

Ile Met Tyr Gly Ile Pro Arg Cys Val Val Gly Glu Asn Val Asn Phe
                165                 170                 175

Lys Ser Lys Gly Glu Lys Tyr Leu Gln Thr Arg Gly His Glu Val Val
            180                 185                 190

Val Val Asp Asp Glu Arg Cys Lys Lys Ile Met Lys Gln Phe Ile Asp
        195                 200                 205

Glu Arg Pro Gln Asp Trp Phe Glu Asp Ile Gly Glu Leu His His
    210                 215                 220

His His His His
225

<210> SEQ ID NO 6
<211> LENGTH: 443
<212> TYPE: PRT
<213> ORGANISM: Artificial Sequence
<220> FEATURE:
<223> OTHER INFORMATION: RGD_EGF_yCD_yUPRT

<400> SEQUENCE: 6

Met Ala Arg Gly Asp Asn Ser Asp Ser Glu Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
            35                  40                  45

Tyr Arg Asp Leu Lys Trp Trp Glu Leu Arg Pro Gly Gly Gly Gly Val
        50                  55                  60

Thr Gly Gly Met Ala Ser Lys Trp Asp Gln Lys Gly Met Asp Ile Ala
65                  70                  75                  80

Tyr Glu Glu Ala Ala Leu Gly Tyr Lys Glu Gly Val Pro Ile Gly
                85                  90                  95

Gly Cys Leu Ile Asn Asn Lys Asp Gly Ser Val Leu Gly Arg Gly His
            100                 105                 110

Asn Met Arg Phe Gln Lys Gly Ser Ala Thr Leu His Gly Glu Ile Ser
            115                 120                 125

Thr Leu Glu Asn Cys Gly Arg Leu Glu Gly Lys Val Tyr Lys Asp Thr
```

```
            130                 135                 140
Thr Leu Tyr Thr Thr Leu Ser Pro Cys Asp Met Cys Thr Gly Ala Ile
145                 150                 155                 160

Ile Met Tyr Gly Ile Pro Arg Cys Val Val Gly Glu Asn Val Asn Phe
                165                 170                 175

Lys Ser Lys Gly Glu Lys Tyr Leu Gln Thr Arg Gly His Glu Val Val
            180                 185                 190

Val Val Asp Asp Glu Arg Cys Lys Lys Ile Met Lys Gln Phe Ile Asp
        195                 200                 205

Glu Arg Pro Gln Asp Trp Phe Glu Asp Ile Gly Glu Ala Ser Glu Pro
    210                 215                 220

Phe Lys Asn Val Tyr Leu Leu Pro Gln Thr Asn Gln Leu Leu Gly Leu
225                 230                 235                 240

Tyr Thr Ile Ile Arg Asn Lys Asn Thr Thr Arg Pro Asp Phe Ile Phe
                245                 250                 255

Tyr Ser Asp Arg Ile Ile Arg Leu Leu Val Glu Glu Gly Leu Asn His
            260                 265                 270

Leu Pro Val Gln Lys Gln Ile Val Glu Thr Asp Thr Asn Glu Asn Phe
        275                 280                 285

Glu Gly Val Ser Phe Met Gly Lys Ile Cys Gly Val Ser Ile Val Arg
    290                 295                 300

Ala Gly Glu Ser Met Glu Gln Gly Leu Arg Asp Cys Cys Arg Ser Val
305                 310                 315                 320

Arg Ile Gly Lys Ile Leu Ile Gln Arg Asp Glu Glu Thr Ala Leu Pro
                325                 330                 335

Lys Leu Phe Tyr Glu Lys Leu Pro Glu Asp Ile Ser Glu Arg Tyr Val
            340                 345                 350

Phe Leu Leu Asp Pro Met Leu Ala Thr Gly Gly Ser Ala Ile Met Ala
        355                 360                 365

Thr Glu Val Leu Ile Lys Arg Gly Val Lys Pro Glu Arg Ile Tyr Phe
    370                 375                 380

Leu Asn Leu Ile Cys Ser Lys Glu Gly Ile Glu Lys Tyr His Ala Ala
385                 390                 395                 400

Phe Pro Glu Val Arg Ile Val Thr Gly Ala Leu Asp Arg Gly Leu Asp
                405                 410                 415

Glu Asn Lys Tyr Leu Val Pro Gly Leu Gly Asp Phe Gly Asp Arg Tyr
            420                 425                 430

Tyr Cys Val Leu Glu His His His His His
        435                 440

<210> SEQ ID NO 7
<211> LENGTH: 234
<212> TYPE: PRT
<213> ORGANISM: Artificial Sequence
<220> FEATURE:
<223> OTHER INFORMATION: RGD4C_EGF_yCD

<400> SEQUENCE: 7

Met Ala Cys Asp Cys Arg Gly Asp Cys Phe Cys Asn Ser Asp Ser Glu
1               5                   10                  15

Cys Pro Leu Ser His Asp Gly Tyr Cys Leu His Asp Gly Val Cys Met
                20                  25                  30

Tyr Ile Glu Ala Leu Asp Lys Tyr Ala Cys Asn Cys Val Val Gly Tyr
            35                  40                  45

Ile Gly Glu Arg Cys Gln Tyr Arg Asp Leu Lys Trp Trp Glu Leu Arg
```

```
            50                  55                  60
Pro Gly Gly Gly Gly Val Thr Gly Gly Met Ala Ser Lys Trp Asp Gln
 65                  70                  75                  80

Lys Gly Met Asp Ile Ala Tyr Glu Glu Ala Ala Leu Gly Tyr Lys Glu
                 85                  90                  95

Gly Gly Val Pro Ile Gly Gly Cys Leu Ile Asn Asn Lys Asp Gly Ser
                100                 105                 110

Val Leu Gly Arg Gly His Asn Met Arg Phe Gln Lys Gly Ser Ala Thr
                115                 120                 125

Leu His Gly Glu Ile Ser Thr Leu Glu Asn Cys Gly Arg Leu Glu Gly
            130                 135                 140

Lys Val Tyr Lys Asp Thr Thr Leu Tyr Thr Thr Leu Ser Pro Cys Asp
145                 150                 155                 160

Met Cys Thr Gly Ala Ile Ile Met Tyr Gly Ile Pro Arg Cys Val Val
                165                 170                 175

Gly Glu Asn Val Asn Phe Lys Ser Lys Gly Glu Lys Tyr Leu Gln Thr
                180                 185                 190

Arg Gly His Glu Val Val Val Asp Asp Glu Arg Cys Lys Lys Ile
            195                 200                 205

Met Lys Gln Phe Ile Asp Glu Arg Pro Gln Asp Trp Phe Glu Asp Ile
210                 215                 220

Gly Glu Leu Glu His His His His His His
225                 230
```

<210> SEQ ID NO 8
<211> LENGTH: 449
<212> TYPE: PRT
<213> ORGANISM: Artificial Sequence
<220> FEATURE:
<223> OTHER INFORMATION: RGD4C_EGF_yCD_yUPRT

<400> SEQUENCE: 8

```
Met Ala Cys Asp Cys Arg Gly Asp Cys Phe Cys Asn Ser Asp Ser Glu
 1               5                  10                  15

Cys Pro Leu Ser His Asp Gly Tyr Cys Leu His Asp Gly Val Cys Met
                20                  25                  30

Tyr Ile Glu Ala Leu Asp Lys Tyr Ala Cys Asn Cys Val Val Gly Tyr
             35                  40                  45

Ile Gly Glu Arg Cys Gln Tyr Arg Asp Leu Lys Trp Trp Glu Leu Arg
         50                  55                  60

Pro Gly Gly Gly Gly Val Thr Gly Gly Met Ala Ser Lys Trp Asp Gln
 65                  70                  75                  80

Lys Gly Met Asp Ile Ala Tyr Glu Glu Ala Ala Leu Gly Tyr Lys Glu
                 85                  90                  95

Gly Gly Val Pro Ile Gly Gly Cys Leu Ile Asn Asn Lys Asp Gly Ser
                100                 105                 110

Val Leu Gly Arg Gly His Asn Met Arg Phe Gln Lys Gly Ser Ala Thr
                115                 120                 125

Leu His Gly Glu Ile Ser Thr Leu Glu Asn Cys Gly Arg Leu Glu Gly
            130                 135                 140

Lys Val Tyr Lys Asp Thr Thr Leu Tyr Thr Thr Leu Ser Pro Cys Asp
145                 150                 155                 160

Met Cys Thr Gly Ala Ile Ile Met Tyr Gly Ile Pro Arg Cys Val Val
                165                 170                 175

Gly Glu Asn Val Asn Phe Lys Ser Lys Gly Glu Lys Tyr Leu Gln Thr
```

```
              180                 185                 190
Arg Gly His Glu Val Val Val Asp Asp Glu Arg Cys Lys Lys Ile
            195                 200                 205
Met Lys Gln Phe Ile Asp Glu Arg Pro Gln Asp Trp Phe Glu Asp Ile
        210                 215                 220
Gly Glu Ala Ser Glu Pro Phe Lys Asn Val Tyr Leu Leu Pro Gln Thr
225                 230                 235                 240
Asn Gln Leu Leu Gly Leu Tyr Thr Ile Ile Arg Asn Lys Asn Thr Thr
                245                 250                 255
Arg Pro Asp Phe Ile Phe Tyr Ser Asp Arg Ile Ile Arg Leu Leu Val
                260                 265                 270
Glu Glu Gly Leu Asn His Leu Pro Val Gln Lys Gln Ile Val Glu Thr
                275                 280                 285
Asp Thr Asn Glu Asn Phe Glu Gly Val Ser Phe Met Gly Lys Ile Cys
            290                 295                 300
Gly Val Ser Ile Val Arg Ala Gly Glu Ser Met Glu Gln Gly Leu Arg
305                 310                 315                 320
Asp Cys Cys Arg Ser Val Arg Ile Gly Lys Ile Leu Ile Gln Arg Asp
                325                 330                 335
Glu Glu Thr Ala Leu Pro Lys Leu Phe Tyr Glu Lys Leu Pro Glu Asp
                340                 345                 350
Ile Ser Glu Arg Tyr Val Phe Leu Leu Asp Pro Met Leu Ala Thr Gly
                355                 360                 365
Gly Ser Ala Ile Met Ala Thr Glu Val Leu Ile Lys Arg Gly Val Lys
370                 375                 380
Pro Glu Arg Ile Tyr Phe Leu Asn Leu Ile Cys Ser Lys Glu Gly Ile
385                 390                 395                 400
Glu Lys Tyr His Ala Ala Phe Pro Glu Val Arg Ile Val Thr Gly Ala
                405                 410                 415
Leu Asp Arg Gly Leu Asp Glu Asn Lys Tyr Leu Val Pro Gly Leu Gly
                420                 425                 430
Asp Phe Gly Asp Arg Tyr Tyr Cys Val Leu Glu His His His His His
            435                 440                 445
His

<210> SEQ ID NO 9
<211> LENGTH: 228
<212> TYPE: PRT
<213> ORGANISM: Artificial Sequence
<220> FEATURE:
<223> OTHER INFORMATION: yCD_RGD_EGF

<400> SEQUENCE: 9

Met Val Val Thr Gly Gly Met Ala Ser Lys Trp Asp Gln Lys Gly Met
1               5                   10                  15
Asp Ile Ala Tyr Glu Glu Ala Ala Leu Gly Tyr Lys Glu Gly Gly Val
            20                  25                  30
Pro Ile Gly Gly Cys Leu Ile Asn Asn Lys Asp Gly Ser Val Leu Gly
        35                  40                  45
Arg Gly His Asn Met Arg Phe Gln Lys Gly Ser Ala Thr Leu His Gly
    50                  55                  60
Glu Ile Ser Thr Leu Glu Asn Cys Gly Arg Leu Glu Gly Lys Val Tyr
65                  70                  75                  80
Lys Asp Thr Thr Leu Tyr Thr Thr Leu Ser Pro Cys Asp Met Cys Thr
                85                  90                  95
```

Gly Ala Ile Ile Met Tyr Gly Ile Pro Arg Cys Val Gly Glu Asn
                100                 105                 110

Val Asn Phe Lys Ser Lys Gly Glu Lys Tyr Leu Gln Thr Arg Gly His
                115                 120                 125

Glu Val Val Val Asp Asp Glu Arg Cys Lys Lys Ile Met Lys Gln
130                 135                 140

Phe Ile Asp Glu Arg Pro Gln Asp Trp Phe Glu Asp Ile Gly Glu Pro
145                 150                 155                 160

Gly Gly Gly Gly Arg Gly Asp Asn Ser Asp Ser Glu Cys Pro Leu Ser
                165                 170                 175

His Asp Gly Tyr Cys Leu His Asp Gly Val Cys Met Tyr Ile Glu Ala
                180                 185                 190

Leu Asp Lys Tyr Ala Cys Asn Cys Val Val Gly Tyr Ile Gly Glu Arg
                195                 200                 205

Cys Gln Tyr Arg Asp Leu Lys Trp Trp Glu Leu Arg Leu Glu His His
                210                 215                 220

His His His His
225

<210> SEQ ID NO 10
<211> LENGTH: 443
<212> TYPE: PRT
<213> ORGANISM: Artificial Sequence
<220> FEATURE:
<223> OTHER INFORMATION: yCD_yUPRT_RGD_EGF

<400> SEQUENCE: 10

Met Val Val Thr Gly Gly Met Ala Ser Lys Trp Asp Gln Lys Gly Met
1               5                   10                  15

Asp Ile Ala Tyr Glu Glu Ala Ala Leu Gly Tyr Lys Glu Gly Gly Val
                20                  25                  30

Pro Ile Gly Gly Cys Leu Ile Asn Asn Lys Asp Gly Ser Val Leu Gly
                35                  40                  45

Arg Gly His Asn Met Arg Phe Gln Lys Gly Ser Ala Thr Leu His Gly
                50                  55                  60

Glu Ile Ser Thr Leu Glu Asn Cys Gly Arg Leu Glu Gly Lys Val Tyr
65                  70                  75                  80

Lys Asp Thr Thr Leu Tyr Thr Thr Leu Ser Pro Cys Asp Met Cys Thr
                85                  90                  95

Gly Ala Ile Ile Met Tyr Gly Ile Pro Arg Cys Val Val Gly Glu Asn
                100                 105                 110

Val Asn Phe Lys Ser Lys Gly Glu Lys Tyr Leu Gln Thr Arg Gly His
                115                 120                 125

Glu Val Val Val Asp Asp Glu Arg Cys Lys Lys Ile Met Lys Gln
130                 135                 140

Phe Ile Asp Glu Arg Pro Gln Asp Trp Phe Glu Asp Ile Gly Glu Ala
145                 150                 155                 160

Ser Glu Pro Phe Lys Asn Val Tyr Leu Leu Pro Gln Thr Asn Gln Leu
                165                 170                 175

Leu Gly Leu Tyr Thr Ile Ile Arg Asn Lys Asn Thr Thr Arg Pro Asp
                180                 185                 190

Phe Ile Phe Tyr Ser Asp Arg Ile Ile Arg Leu Leu Val Glu Glu Gly
                195                 200                 205

Leu Asn His Leu Pro Val Gln Lys Gln Ile Val Glu Thr Asp Thr Asn
210                 215                 220

```
Glu Asn Phe Glu Gly Val Ser Phe Met Gly Lys Ile Cys Gly Val Ser
225                 230                 235                 240

Ile Val Arg Ala Gly Glu Ser Met Glu Gln Gly Leu Arg Asp Cys Cys
                245                 250                 255

Arg Ser Val Arg Ile Gly Lys Ile Leu Ile Gln Arg Asp Glu Thr
            260                 265                 270

Ala Leu Pro Lys Leu Phe Tyr Glu Lys Leu Pro Glu Asp Ile Ser Glu
            275                 280                 285

Arg Tyr Val Phe Leu Leu Asp Pro Met Leu Ala Thr Gly Gly Ser Ala
            290                 295                 300

Ile Met Ala Thr Glu Val Leu Ile Lys Arg Gly Val Lys Pro Glu Arg
305                 310                 315                 320

Ile Tyr Phe Leu Asn Leu Ile Cys Ser Lys Glu Gly Ile Glu Lys Tyr
                325                 330                 335

His Ala Ala Phe Pro Glu Val Arg Ile Val Thr Gly Ala Leu Asp Arg
                340                 345                 350

Gly Leu Asp Glu Asn Lys Tyr Leu Val Pro Gly Leu Gly Asp Phe Gly
            355                 360                 365

Asp Arg Tyr Tyr Cys Val Pro Gly Gly Gly Arg Gly Asp Asn Ser
370                 375                 380

Asp Ser Glu Cys Pro Leu Ser His Asp Gly Tyr Cys Leu His Asp Gly
385                 390                 395                 400

Val Cys Met Tyr Ile Glu Ala Leu Asp Lys Tyr Ala Cys Asn Cys Val
                405                 410                 415

Val Gly Tyr Ile Gly Glu Arg Cys Gln Tyr Arg Asp Leu Lys Trp Trp
                420                 425                 430

Glu Leu Arg Leu Glu His His His His His
            435                 440

<210> SEQ ID NO 11
<211> LENGTH: 234
<212> TYPE: PRT
<213> ORGANISM: Artificial Sequence
<220> FEATURE:
<223> OTHER INFORMATION: yCD_RGD4C_EGF

<400> SEQUENCE: 11

Met Val Val Thr Gly Gly Met Ala Ser Lys Trp Asp Gln Lys Gly Met
1               5                   10                  15

Asp Ile Ala Tyr Glu Glu Ala Leu Gly Tyr Lys Glu Gly Gly Val
            20                  25                  30

Pro Ile Gly Gly Cys Leu Ile Asn Asn Lys Asp Gly Ser Val Leu Gly
            35                  40                  45

Arg Gly His Asn Met Arg Phe Gln Lys Gly Ser Ala Thr Leu His Gly
        50                  55                  60

Glu Ile Ser Thr Leu Glu Asn Cys Gly Arg Leu Glu Gly Lys Val Tyr
65                  70                  75                  80

Lys Asp Thr Thr Leu Tyr Thr Thr Leu Ser Pro Cys Asp Met Cys Thr
                85                  90                  95

Gly Ala Ile Ile Met Tyr Gly Ile Pro Arg Cys Val Val Gly Glu Asn
            100                 105                 110

Val Asn Phe Lys Ser Lys Gly Glu Lys Tyr Leu Gln Thr Arg Gly His
            115                 120                 125

Glu Val Val Val Val Asp Asp Glu Arg Cys Lys Lys Ile Met Lys Gln
130                 135                 140
```

```
Phe Ile Asp Glu Arg Pro Gln Asp Trp Phe Glu Asp Ile Gly Glu Pro
145                 150                 155                 160

Gly Gly Gly Gly Cys Asp Cys Arg Gly Asp Cys Phe Cys Asn Ser Asp
                165                 170                 175

Ser Glu Cys Pro Leu Ser His Asp Gly Tyr Cys Leu His Asp Gly Val
            180                 185                 190

Cys Met Tyr Ile Glu Ala Leu Asp Lys Tyr Ala Cys Asn Cys Val Val
        195                 200                 205

Gly Tyr Ile Gly Glu Arg Cys Gln Tyr Arg Asp Leu Lys Trp Trp Glu
    210                 215                 220

Leu Arg Leu Glu His His His His His His
225                 230
```

<210> SEQ ID NO 12
<211> LENGTH: 449
<212> TYPE: PRT
<213> ORGANISM: Artificial Sequence
<220> FEATURE:
<223> OTHER INFORMATION: yCD_yUPRT_RGD4C_EGF

<400> SEQUENCE: 12

```
Met Val Val Thr Gly Met Ala Ser Lys Trp Asp Gln Lys Gly Met
1               5                   10                  15

Asp Ile Ala Tyr Glu Glu Ala Leu Gly Tyr Lys Glu Gly Gly Val
            20                  25                  30

Pro Ile Gly Gly Cys Leu Ile Asn Asn Lys Asp Gly Ser Val Leu Gly
                35                  40                  45

Arg Gly His Asn Met Arg Phe Gln Lys Gly Ser Ala Thr Leu His Gly
    50                  55                  60

Glu Ile Ser Thr Leu Glu Asn Cys Gly Arg Leu Glu Gly Lys Val Tyr
65                  70                  75                  80

Lys Asp Thr Thr Leu Tyr Thr Thr Leu Ser Pro Cys Asp Met Cys Thr
                85                  90                  95

Gly Ala Ile Ile Met Tyr Gly Ile Pro Arg Cys Val Val Gly Glu Asn
            100                 105                 110

Val Asn Phe Lys Ser Lys Gly Glu Lys Tyr Leu Gln Thr Arg Gly His
        115                 120                 125

Glu Val Val Val Asp Asp Glu Arg Cys Lys Lys Ile Met Lys Gln
    130                 135                 140

Phe Ile Asp Glu Arg Pro Gln Asp Trp Phe Glu Asp Ile Gly Glu Ala
145                 150                 155                 160

Ser Glu Pro Phe Lys Asn Val Tyr Leu Leu Pro Gln Thr Asn Gln Leu
                165                 170                 175

Leu Gly Leu Tyr Thr Ile Ile Arg Asn Lys Asn Thr Thr Arg Pro Asp
            180                 185                 190

Phe Ile Phe Tyr Ser Asp Arg Ile Ile Arg Leu Leu Val Glu Glu Gly
        195                 200                 205

Leu Asn His Leu Pro Val Gln Lys Gln Ile Val Glu Thr Asp Thr Asn
    210                 215                 220

Glu Asn Phe Glu Gly Val Ser Phe Met Gly Lys Ile Cys Gly Val Ser
225                 230                 235                 240

Ile Val Arg Ala Gly Glu Ser Met Glu Gln Gly Leu Arg Asp Cys Cys
                245                 250                 255

Arg Ser Val Arg Ile Gly Lys Ile Leu Ile Gln Arg Asp Glu Glu Thr
            260                 265                 270
```

```
Ala Leu Pro Lys Leu Phe Tyr Glu Lys Leu Pro Glu Asp Ile Ser Glu
        275                 280                 285

Arg Tyr Val Phe Leu Leu Asp Pro Met Leu Ala Thr Gly Gly Ser Ala
    290                 295                 300

Ile Met Ala Thr Glu Val Leu Ile Lys Arg Gly Val Lys Pro Glu Arg
305                 310                 315                 320

Ile Tyr Phe Leu Asn Leu Ile Cys Ser Lys Glu Gly Ile Glu Lys Tyr
                325                 330                 335

His Ala Ala Phe Pro Glu Val Arg Ile Val Thr Gly Ala Leu Asp Arg
            340                 345                 350

Gly Leu Asp Glu Asn Lys Tyr Leu Val Pro Gly Leu Gly Asp Phe Gly
        355                 360                 365

Asp Arg Tyr Tyr Cys Val Pro Gly Gly Gly Cys Asp Cys Arg Gly
    370                 375                 380

Asp Cys Phe Cys Asn Ser Asp Ser Glu Cys Pro Leu Ser His Asp Gly
385                 390                 395                 400

Tyr Cys Leu His Asp Gly Val Cys Met Tyr Ile Glu Ala Leu Asp Lys
                405                 410                 415

Tyr Ala Cys Asn Cys Val Val Gly Tyr Ile Gly Glu Arg Cys Gln Tyr
            420                 425                 430

Arg Asp Leu Lys Trp Trp Glu Leu Arg Leu Glu His His His His
        435                 440                 445

His

<210> SEQ ID NO 13
<211> LENGTH: 296
<212> TYPE: PRT
<213> ORGANISM: Artificial Sequence
<220> FEATURE:
<223> OTHER INFORMATION: RGD_VEGF_yCD

<400> SEQUENCE: 13

Met Gly Arg Gly Asp Ala Pro Met Ala Glu Gly Gly Gly Gln Asn His
1               5                   10                  15

His Glu Val Val Lys Phe Met Asp Val Tyr Gln Arg Ser Tyr Cys His
            20                  25                  30

Pro Ile Glu Thr Leu Val Asp Ile Phe Gln Glu Tyr Pro Asp Glu Ile
        35                  40                  45

Glu Tyr Ile Phe Lys Pro Ser Cys Val Pro Leu Met Arg Cys Gly Gly
    50                  55                  60

Cys Cys Asn Asp Glu Gly Leu Glu Cys Val Pro Thr Glu Glu Ser Asn
65                  70                  75                  80

Ile Thr Met Gln Ile Met Arg Ile Lys Pro His Gln Gly Gln His Ile
                85                  90                  95

Gly Glu Met Ser Phe Leu Gln His Asn Lys Cys Glu Cys Arg Pro Lys
            100                 105                 110

Lys Asp Arg Ala Arg Gln Glu Lys Cys Asp Lys Pro Arg Arg Pro Gly
        115                 120                 125

Gly Gly Gly Val Thr Gly Gly Met Ala Ser Lys Trp Asp Gln Lys Gly
    130                 135                 140

Met Asp Ile Ala Tyr Glu Glu Ala Ala Leu Gly Tyr Lys Glu Gly Gly
145                 150                 155                 160

Val Pro Ile Gly Gly Cys Leu Ile Asn Asn Lys Asp Gly Ser Val Leu
                165                 170                 175
```

Gly Arg Gly His Asn Met Arg Phe Gln Lys Gly Ser Ala Thr Leu His
            180                 185                 190

Gly Glu Ile Ser Thr Leu Glu Asn Cys Gly Arg Leu Glu Gly Lys Val
        195                 200                 205

Tyr Lys Asp Thr Thr Leu Tyr Thr Thr Leu Ser Pro Cys Asp Met Cys
    210                 215                 220

Thr Gly Ala Ile Ile Met Tyr Gly Ile Pro Arg Cys Val Val Gly Glu
225                 230                 235                 240

Asn Val Asn Phe Lys Ser Lys Gly Glu Lys Tyr Leu Gln Thr Arg Gly
                245                 250                 255

His Glu Val Val Val Val Asp Glu Arg Cys Lys Lys Ile Met Lys
        260                 265                 270

Gln Phe Ile Asp Glu Arg Pro Gln Asp Trp Phe Glu Asp Ile Gly Glu
        275                 280                 285

Leu Glu His His His His His His
        290                 295

```
<210> SEQ ID NO 14
<211> LENGTH: 511
<212> TYPE: PRT
<213> ORGANISM: Artificial Sequence
<220> FEATURE:
<223> OTHER INFORMATION: RGD_VEGF_yCD_yUPRT

<400> SEQUENCE: 14
```

Met Gly Arg Gly Asp Ala Pro Met Ala Glu Gly Gly Gly Gln Asn His
1               5                   10                  15

His Glu Val Val Lys Phe Met Asp Val Tyr Gln Arg Ser Tyr Cys His
            20                  25                  30

Pro Ile Glu Thr Leu Val Asp Ile Phe Gln Glu Tyr Pro Asp Glu Ile
        35                  40                  45

Glu Tyr Ile Phe Lys Pro Ser Cys Val Pro Leu Met Arg Cys Gly Gly
    50                  55                  60

Cys Cys Asn Asp Glu Gly Leu Glu Cys Val Pro Thr Glu Glu Ser Asn
65                  70                  75                  80

Ile Thr Met Gln Ile Met Arg Ile Lys Pro His Gln Gly Gln His Ile
                85                  90                  95

Gly Glu Met Ser Phe Leu Gln His Asn Lys Cys Glu Cys Arg Pro Lys
            100                 105                 110

Lys Asp Arg Ala Arg Gln Glu Lys Cys Asp Lys Pro Arg Arg Pro Gly
        115                 120                 125

Gly Gly Gly Val Thr Gly Gly Met Ala Ser Lys Trp Asp Gln Lys Gly
    130                 135                 140

Met Asp Ile Ala Tyr Glu Glu Ala Ala Leu Gly Tyr Lys Glu Gly Gly
145                 150                 155                 160

Val Pro Ile Gly Gly Cys Leu Ile Asn Asn Lys Asp Gly Ser Val Leu
                165                 170                 175

Gly Arg Gly His Asn Met Arg Phe Gln Lys Gly Ser Ala Thr Leu His
            180                 185                 190

Gly Glu Ile Ser Thr Leu Glu Asn Cys Gly Arg Leu Glu Gly Lys Val
        195                 200                 205

Tyr Lys Asp Thr Thr Leu Tyr Thr Thr Leu Ser Pro Cys Asp Met Cys
    210                 215                 220

Thr Gly Ala Ile Ile Met Tyr Gly Ile Pro Arg Cys Val Val Gly Glu
225                 230                 235                 240

-continued

```
Asn Val Asn Phe Lys Ser Lys Gly Glu Lys Tyr Leu Gln Thr Arg Gly
                245                 250                 255

His Glu Val Val Val Asp Asp Glu Arg Cys Lys Lys Ile Met Lys
            260                 265                 270

Gln Phe Ile Asp Glu Arg Pro Gln Asp Trp Phe Glu Asp Ile Gly Glu
            275                 280                 285

Ala Ser Glu Pro Phe Lys Asn Val Tyr Leu Leu Pro Gln Thr Asn Gln
        290                 295                 300

Leu Leu Gly Leu Tyr Thr Ile Ile Arg Asn Lys Asn Thr Thr Arg Pro
305                 310                 315                 320

Asp Phe Ile Phe Tyr Ser Asp Arg Ile Ile Arg Leu Leu Val Glu Glu
                325                 330                 335

Gly Leu Asn His Leu Pro Val Gln Lys Gln Ile Val Glu Thr Asp Thr
            340                 345                 350

Asn Glu Asn Phe Glu Gly Val Ser Phe Met Gly Lys Ile Cys Gly Val
        355                 360                 365

Ser Ile Val Arg Ala Gly Glu Ser Met Glu Gln Gly Leu Arg Asp Cys
        370                 375                 380

Cys Arg Ser Val Arg Ile Gly Lys Ile Leu Ile Gln Arg Asp Glu Glu
385                 390                 395                 400

Thr Ala Leu Pro Lys Leu Phe Tyr Glu Lys Leu Pro Glu Asp Ile Ser
                405                 410                 415

Glu Arg Tyr Val Phe Leu Leu Asp Pro Met Leu Ala Thr Gly Gly Ser
            420                 425                 430

Ala Ile Met Ala Thr Glu Val Leu Ile Lys Arg Gly Val Lys Pro Glu
        435                 440                 445

Arg Ile Tyr Phe Leu Asn Leu Ile Cys Ser Lys Glu Gly Ile Glu Lys
    450                 455                 460

Tyr His Ala Ala Phe Pro Glu Val Arg Ile Val Thr Gly Ala Leu Asp
465                 470                 475                 480

Arg Gly Leu Asp Glu Asn Lys Tyr Leu Val Pro Gly Leu Gly Asp Phe
                485                 490                 495

Gly Asp Arg Tyr Tyr Cys Val Leu Glu His His His His His His
            500                 505                 510

<210> SEQ ID NO 15
<211> LENGTH: 302
<212> TYPE: PRT
<213> ORGANISM: Artificial Sequence
<220> FEATURE:
<223> OTHER INFORMATION: RGD4C_VEGF_yCD

<400> SEQUENCE: 15

Met Gly Cys Asp Cys Arg Gly Asp Cys Phe Cys Ala Pro Met Ala Glu
1               5                   10                  15

Gly Gly Gly Gln Asn His His Glu Val Val Lys Phe Met Asp Val Tyr
            20                  25                  30

Gln Arg Ser Tyr Cys His Pro Ile Glu Thr Leu Val Asp Ile Phe Gln
        35                  40                  45

Glu Tyr Pro Asp Glu Ile Glu Tyr Ile Phe Lys Pro Ser Cys Val Pro
    50                  55                  60

Leu Met Arg Cys Gly Gly Cys Cys Asn Asp Glu Gly Leu Glu Cys Val
65                  70                  75                  80

Pro Thr Glu Glu Ser Asn Ile Thr Met Gln Ile Met Arg Ile Lys Pro
                85                  90                  95
```

```
His Gln Gly Gln His Ile Gly Glu Met Ser Phe Leu Gln His Asn Lys
            100                 105                 110

Cys Glu Cys Arg Pro Lys Lys Asp Arg Ala Arg Gln Glu Lys Cys Asp
        115                 120                 125

Lys Pro Arg Arg Pro Gly Gly Gly Gly Val Thr Gly Gly Met Ala Ser
    130                 135                 140

Lys Trp Asp Gln Lys Gly Met Asp Ile Ala Tyr Glu Glu Ala Ala Leu
145                 150                 155                 160

Gly Tyr Lys Glu Gly Gly Val Pro Ile Gly Gly Cys Leu Ile Asn Asn
                165                 170                 175

Lys Asp Gly Ser Val Leu Gly Arg Gly His Asn Met Arg Phe Gln Lys
            180                 185                 190

Gly Ser Ala Thr Leu His Gly Glu Ile Ser Thr Leu Glu Asn Cys Gly
        195                 200                 205

Arg Leu Glu Gly Lys Val Tyr Lys Asp Thr Thr Leu Tyr Thr Thr Leu
    210                 215                 220

Ser Pro Cys Asp Met Cys Thr Gly Ala Ile Ile Met Tyr Gly Ile Pro
225                 230                 235                 240

Arg Cys Val Val Gly Glu Asn Val Asn Phe Lys Ser Lys Gly Glu Lys
                245                 250                 255

Tyr Leu Gln Thr Arg Gly His Glu Val Val Val Val Asp Asp Glu Arg
            260                 265                 270

Cys Lys Lys Ile Met Lys Gln Phe Ile Asp Glu Arg Pro Gln Asp Trp
        275                 280                 285

Phe Glu Asp Ile Gly Glu Leu Glu His His His His His His
    290                 295                 300

<210> SEQ ID NO 16
<211> LENGTH: 517
<212> TYPE: PRT
<213> ORGANISM: Artificial Sequence
<220> FEATURE:
<223> OTHER INFORMATION: RGD4C_VEGF_yCD_yUPRT

<400> SEQUENCE: 16

Met Gly Cys Asp Cys Arg Gly Asp Cys Phe Cys Ala Pro Met Ala Glu
1               5                   10                  15

Gly Gly Gly Gln Asn His His Glu Val Val Lys Phe Met Asp Val Tyr
                20                  25                  30

Gln Arg Ser Tyr Cys His Pro Ile Glu Thr Leu Val Asp Ile Phe Gln
            35                  40                  45

Glu Tyr Pro Asp Glu Ile Glu Tyr Ile Phe Lys Pro Ser Cys Val Pro
    50                  55                  60

Leu Met Arg Cys Gly Gly Cys Cys Asn Asp Glu Gly Leu Glu Cys Val
65                  70                  75                  80

Pro Thr Glu Glu Ser Asn Ile Thr Met Gln Ile Met Arg Ile Lys Pro
                85                  90                  95

His Gln Gly Gln His Ile Gly Glu Met Ser Phe Leu Gln His Asn Lys
            100                 105                 110

Cys Glu Cys Arg Pro Lys Lys Asp Arg Ala Arg Gln Glu Lys Cys Asp
        115                 120                 125

Lys Pro Arg Arg Pro Gly Gly Gly Gly Val Thr Gly Gly Met Ala Ser
    130                 135                 140

Lys Trp Asp Gln Lys Gly Met Asp Ile Ala Tyr Glu Glu Ala Ala Leu
145                 150                 155                 160
```

Gly Tyr Lys Glu Gly Gly Val Pro Ile Gly Cys Leu Ile Asn Asn
                165                 170                 175

Lys Asp Gly Ser Val Leu Gly Arg Gly His Asn Met Arg Phe Gln Lys
            180                 185                 190

Gly Ser Ala Thr Leu His Gly Glu Ile Ser Thr Leu Glu Asn Cys Gly
        195                 200                 205

Arg Leu Glu Gly Lys Val Tyr Lys Asp Thr Thr Leu Tyr Thr Thr Leu
    210                 215                 220

Ser Pro Cys Asp Met Cys Thr Gly Ala Ile Ile Met Tyr Gly Ile Pro
225                 230                 235                 240

Arg Cys Val Val Gly Glu Asn Val Asn Phe Lys Ser Lys Gly Glu Lys
                245                 250                 255

Tyr Leu Gln Thr Arg Gly His Glu Val Val Val Asp Asp Glu Arg
            260                 265                 270

Cys Lys Lys Ile Met Lys Gln Phe Ile Asp Glu Arg Pro Gln Asp Trp
        275                 280                 285

Phe Glu Asp Ile Gly Glu Ala Ser Glu Pro Phe Lys Asn Val Tyr Leu
    290                 295                 300

Leu Pro Gln Thr Asn Gln Leu Leu Gly Leu Tyr Thr Ile Ile Arg Asn
305                 310                 315                 320

Lys Asn Thr Thr Arg Pro Asp Phe Ile Phe Tyr Ser Asp Arg Ile Ile
                325                 330                 335

Arg Leu Leu Val Glu Glu Gly Leu Asn His Leu Pro Val Gln Lys Gln
            340                 345                 350

Ile Val Glu Thr Asp Thr Asn Glu Asn Phe Gly Val Ser Phe Met
        355                 360                 365

Gly Lys Ile Cys Gly Val Ser Ile Val Arg Ala Gly Glu Ser Met Glu
    370                 375                 380

Gln Gly Leu Arg Asp Cys Cys Arg Ser Val Arg Ile Gly Lys Ile Leu
385                 390                 395                 400

Ile Gln Arg Asp Glu Glu Thr Ala Leu Pro Lys Leu Phe Tyr Glu Lys
                405                 410                 415

Leu Pro Glu Asp Ile Ser Glu Arg Tyr Val Phe Leu Leu Asp Pro Met
            420                 425                 430

Leu Ala Thr Gly Gly Ser Ala Ile Met Ala Thr Glu Val Leu Ile Lys
        435                 440                 445

Arg Gly Val Lys Pro Glu Arg Ile Tyr Phe Leu Asn Leu Ile Cys Ser
    450                 455                 460

Lys Glu Gly Ile Glu Lys Tyr His Ala Ala Phe Pro Glu Val Arg Ile
465                 470                 475                 480

Val Thr Gly Ala Leu Asp Arg Gly Leu Asp Glu Asn Lys Tyr Leu Val
                485                 490                 495

Pro Gly Leu Gly Asp Phe Gly Asp Arg Tyr Tyr Cys Val Leu Glu His
            500                 505                 510

His His His His
        515

<210> SEQ ID NO 17
<211> LENGTH: 435
<212> TYPE: PRT
<213> ORGANISM: Artificial Sequence
<220> FEATURE:
<223> OTHER INFORMATION: EcCD_WT

<400> SEQUENCE: 17

```
Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
            35                  40                  45

Ala Glu Gln Gly Leu Val Ile Pro Pro Phe Val Glu Pro His Ile His
50                      55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
                100                 105                 110

Ile Ala Asn Gly Ile Gln His Val Arg Thr His Val Asp Val Ser Asp
                115                 120                 125

Ala Thr Leu Thr Ala Leu Lys Ala Met Leu Glu Val Lys Gln Glu Val
            130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Arg Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
            195                 200                 205

Asp Arg Leu Ile Asp Val His Cys Asp Glu Ile Asp Asp Glu Gln Ser
            210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
            245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
            275                 280                 285

Thr Tyr Pro Lys Arg Arg Gly Ile Thr Arg Val Lys Glu Met Leu Glu
            290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
            355                 360                 365

Ile Ala Ala Gly Asn Ser Ala Asn Leu Ile Ile Leu Pro Ala Glu Asn
            370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg Leu Glu His His His
```

His His His
        435

<210> SEQ ID NO 18
<211> LENGTH: 435
<212> TYPE: PRT
<213> ORGANISM: Artificial Sequence
<220> FEATURE:
<223> OTHER INFORMATION: EcCD_D314A

<400> SEQUENCE: 18

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Ala Leu Arg Leu
                165                 170                 175

Arg Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Ala Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn

```
                 340                 345                 350
Leu Ile Thr His His Ser Ala Arg Thr Leu Asn Leu Gln Asp Tyr Gly
            355                 360                 365

Ile Ala Ala Gly Asn Ser Ala Asn Leu Ile Ile Leu Pro Ala Glu Asn
        370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg Leu Glu His His His
            420                 425                 430

His His His
        435

<210> SEQ ID NO 19
<211> LENGTH: 446
<212> TYPE: PRT
<213> ORGANISM: Artificial Sequence
<220> FEATURE:
<223> OTHER INFORMATION: RGD4C_EcCD_WT

<400> SEQUENCE: 19

Met Gly Cys Asp Cys Arg Gly Asp Cys Phe Cys Met Ser Asn Asn Ala
1               5                   10                  15

Leu Gln Thr Ile Ile Asn Ala Arg Leu Pro Gly Glu Glu Gly Leu Trp
            20                  25                  30

Gln Ile His Leu Gln Asp Gly Lys Ile Ser Ala Ile Asp Ala Gln Ser
        35                  40                  45

Gly Val Met Pro Ile Thr Glu Asn Ser Leu Asp Ala Glu Gln Gly Leu
    50                  55                  60

Val Ile Pro Pro Phe Val Glu Pro His Ile His Leu Asp Thr Thr Gln
65                  70                  75                  80

Thr Ala Gly Gln Pro Asn Trp Asn Gln Ser Gly Thr Leu Phe Glu Gly
                85                  90                  95

Ile Glu Arg Trp Ala Glu Arg Lys Ala Leu Leu Thr His Asp Asp Val
            100                 105                 110

Lys Gln Arg Ala Trp Gln Thr Leu Lys Trp Gln Ile Ala Asn Gly Ile
        115                 120                 125

Gln His Val Arg Thr His Val Asp Val Ser Asp Ala Thr Leu Thr Ala
    130                 135                 140

Leu Lys Ala Met Leu Glu Val Lys Gln Glu Val Ala Pro Trp Ile Asp
145                 150                 155                 160

Leu Gln Ile Val Ala Phe Pro Gln Glu Gly Ile Leu Ser Tyr Pro Asn
                165                 170                 175

Gly Glu Ala Leu Leu Glu Glu Ala Leu Arg Leu Arg Ala Asp Val Val
            180                 185                 190

Gly Ala Ile Pro His Phe Glu Phe Thr Arg Glu Tyr Gly Val Glu Ser
        195                 200                 205

Leu His Lys Thr Phe Ala Leu Ala Gln Lys Tyr Asp Arg Leu Ile Asp
    210                 215                 220

Val His Cys Asp Glu Ile Asp Asp Glu Gln Ser Arg Phe Val Glu Thr
225                 230                 235                 240

Val Ala Ala Leu Ala His His Glu Gly Met Gly Ala Arg Val Thr Ala
                245                 250                 255

Ser His Thr Thr Ala Met His Ser Tyr Asn Gly Ala Tyr Thr Ser Arg
```

```
                    260                 265                 270
Leu Phe Arg Leu Leu Lys Met Ser Gly Ile Asn Phe Val Ala Asn Pro
                275                 280                 285

Leu Val Asn Ile His Leu Gln Gly Arg Phe Asp Thr Tyr Pro Lys Arg
            290                 295                 300

Arg Gly Ile Thr Arg Val Lys Glu Met Leu Glu Ser Gly Ile Asn Val
305                 310                 315                 320

Cys Phe Gly His Asp Asp Val Phe Asp Pro Trp Tyr Pro Leu Gly Thr
                325                 330                 335

Ala Asn Met Leu Gln Val Leu His Met Gly Leu His Val Cys Gln Leu
            340                 345                 350

Met Gly Tyr Gly Gln Ile Asn Asp Gly Leu Asn Leu Ile Thr His His
                355                 360                 365

Ser Ala Arg Thr Leu Asn Leu Gln Asp Tyr Gly Ile Ala Ala Gly Asn
            370                 375                 380

Ser Ala Asn Leu Ile Ile Leu Pro Ala Glu Asn Gly Phe Asp Ala Leu
385                 390                 395                 400

Arg Arg Gln Val Pro Val Arg Tyr Ser Val Arg Gly Gly Lys Val Ile
                405                 410                 415

Ala Ser Thr Gln Pro Ala Gln Thr Thr Val Tyr Leu Glu Gln Pro Glu
            420                 425                 430

Ala Ile Asp Tyr Lys Arg Leu Glu His His His His His His
                435                 440                 445

<210> SEQ ID NO 20
<211> LENGTH: 446
<212> TYPE: PRT
<213> ORGANISM: Artificial Sequence
<220> FEATURE:
<223> OTHER INFORMATION: RGD4C_EcCD_D314A

<400> SEQUENCE: 20

Met Gly Cys Asp Cys Arg Gly Asp Cys Phe Cys Met Ser Asn Asn Ala
1               5                   10                  15

Leu Gln Thr Ile Ile Asn Ala Arg Leu Pro Gly Glu Glu Gly Leu Trp
            20                  25                  30

Gln Ile His Leu Gln Asp Gly Lys Ile Ser Ala Ile Asp Ala Gln Ser
        35                  40                  45

Gly Val Met Pro Ile Thr Glu Asn Ser Leu Asp Ala Glu Gln Gly Leu
    50                  55                  60

Val Ile Pro Pro Phe Val Glu Pro His Ile His Leu Asp Thr Thr Gln
65                  70                  75                  80

Thr Ala Gly Gln Pro Asn Trp Asn Gln Ser Gly Thr Leu Phe Glu Gly
                85                  90                  95

Ile Glu Arg Trp Ala Glu Arg Lys Ala Leu Leu Thr His Asp Asp Val
            100                 105                 110

Lys Gln Arg Ala Trp Gln Thr Leu Lys Trp Gln Ile Ala Asn Gly Ile
        115                 120                 125

Gln His Val Arg Thr His Val Asp Val Ser Asp Ala Thr Leu Thr Ala
    130                 135                 140

Leu Lys Ala Met Leu Glu Val Lys Gln Glu Val Ala Pro Trp Ile Asp
145                 150                 155                 160

Leu Gln Ile Val Ala Phe Pro Gln Glu Gly Ile Leu Ser Tyr Pro Asn
                165                 170                 175

Gly Glu Ala Leu Leu Glu Glu Ala Leu Arg Leu Arg Ala Asp Val Val
```

```
                180              185              190
Gly Ala Ile Pro His Phe Glu Phe Thr Arg Glu Tyr Gly Val Glu Ser
            195                  200                  205
Leu His Lys Thr Phe Ala Leu Ala Gln Lys Tyr Asp Arg Leu Ile Asp
210                  215                  220
Val His Cys Asp Glu Ile Asp Asp Glu Gln Ser Arg Phe Val Glu Thr
225                  230                  235                  240
Val Ala Ala Leu Ala His His Glu Gly Met Gly Ala Arg Val Thr Ala
                245                  250                  255
Ser His Thr Thr Ala Met His Ser Tyr Asn Gly Ala Tyr Thr Ser Arg
            260                  265                  270
Leu Phe Arg Leu Leu Lys Met Ser Gly Ile Asn Phe Val Ala Asn Pro
        275                  280                  285
Leu Val Asn Ile His Leu Gln Gly Arg Phe Asp Thr Tyr Pro Lys Arg
            290                  295                  300
Arg Gly Ile Thr Arg Val Lys Glu Met Leu Glu Ser Gly Ile Asn Val
305                  310                  315                  320
Cys Phe Gly His Asp Ala Val Phe Asp Pro Trp Tyr Pro Leu Gly Thr
                325                  330                  335
Ala Asn Met Leu Gln Val Leu His Met Gly Leu His Val Cys Gln Leu
            340                  345                  350
Met Gly Tyr Gly Gln Ile Asn Asp Gly Leu Asn Leu Ile Thr His His
        355                  360                  365
Ser Ala Arg Thr Leu Asn Leu Gln Asp Tyr Gly Ile Ala Ala Gly Asn
        370                  375                  380
Ser Ala Asn Leu Ile Ile Leu Pro Ala Glu Asn Gly Phe Asp Ala Leu
385                  390                  395                  400
Arg Arg Gln Val Pro Val Arg Tyr Ser Val Arg Gly Gly Lys Val Ile
                405                  410                  415
Ala Ser Thr Gln Pro Ala Gln Thr Thr Val Tyr Leu Glu Gln Pro Glu
            420                  425                  430
Ala Ile Asp Tyr Lys Arg Leu Glu His His His His His His
        435                  440                  445

<210> SEQ ID NO 21
<211> LENGTH: 498
<212> TYPE: PRT
<213> ORGANISM: Artificial Sequence
<220> FEATURE:
<223> OTHER INFORMATION: RGD_EGF_EcCD_WT

<400> SEQUENCE: 21

Met Ala Arg Gly Asp Asn Ser Asp Ser Glu Cys Pro Leu Ser His Asp
1               5                   10                  15
Gly Tyr Cys Leu His Asp Gly Val Cys Met Tyr Ile Glu Ala Leu Asp
            20                  25                  30
Lys Tyr Ala Cys Asn Cys Val Val Gly Tyr Ile Gly Glu Arg Cys Gln
        35                  40                  45
Tyr Arg Asp Leu Lys Trp Trp Glu Leu Arg Pro Gly Gly Gly Gly Met
    50                  55                  60
Ser Asn Asn Ala Leu Gln Thr Ile Ile Asn Ala Arg Leu Pro Gly Glu
65                  70                  75                  80
Glu Gly Leu Trp Gln Ile His Leu Gln Asp Gly Lys Ile Ser Ala Ile
                85                  90                  95
Asp Ala Gln Ser Gly Val Met Pro Ile Thr Glu Asn Ser Leu Asp Ala
```

```
            100                 105                 110
Glu Gln Gly Leu Val Ile Pro Pro Phe Val Glu Pro His Ile His Leu
            115                 120                 125

Asp Thr Thr Gln Thr Ala Gly Gln Pro Asn Trp Asn Gln Ser Gly Thr
130                 135                 140

Leu Phe Glu Gly Ile Glu Arg Trp Ala Glu Arg Lys Ala Leu Leu Thr
145                 150                 155                 160

His Asp Asp Val Lys Gln Arg Ala Trp Gln Thr Leu Lys Trp Gln Ile
                165                 170                 175

Ala Asn Gly Ile Gln His Val Arg Thr His Val Asp Val Ser Asp Ala
            180                 185                 190

Thr Leu Thr Ala Leu Lys Ala Met Leu Glu Val Lys Gln Glu Val Ala
        195                 200                 205

Pro Trp Ile Asp Leu Gln Ile Val Ala Phe Pro Gln Glu Gly Ile Leu
210                 215                 220

Ser Tyr Pro Asn Gly Glu Ala Leu Leu Glu Glu Ala Leu Arg Leu Arg
225                 230                 235                 240

Ala Asp Val Val Gly Ala Ile Pro His Phe Glu Phe Thr Arg Glu Tyr
                245                 250                 255

Gly Val Glu Ser Leu His Lys Thr Phe Ala Leu Ala Gln Lys Tyr Asp
            260                 265                 270

Arg Leu Ile Asp Val His Cys Asp Glu Ile Asp Asp Glu Gln Ser Arg
        275                 280                 285

Phe Val Glu Thr Val Ala Ala Leu Ala His His Glu Gly Met Gly Ala
290                 295                 300

Arg Val Thr Ala Ser His Thr Thr Ala Met His Ser Tyr Asn Gly Ala
305                 310                 315                 320

Tyr Thr Ser Arg Leu Phe Arg Leu Leu Lys Met Ser Gly Ile Asn Phe
                325                 330                 335

Val Ala Asn Pro Leu Val Asn Ile His Leu Gln Gly Arg Phe Asp Thr
            340                 345                 350

Tyr Pro Lys Arg Arg Gly Ile Thr Arg Val Lys Glu Met Leu Glu Ser
        355                 360                 365

Gly Ile Asn Val Cys Phe Gly His Asp Asp Val Phe Asp Pro Trp Tyr
370                 375                 380

Pro Leu Gly Thr Ala Asn Met Leu Gln Val Leu His Met Gly Leu His
385                 390                 395                 400

Val Cys Gln Leu Met Gly Tyr Gly Gln Ile Asn Asp Gly Leu Asn Leu
                405                 410                 415

Ile Thr His His Ser Ala Arg Thr Leu Asn Leu Gln Asp Tyr Gly Ile
            420                 425                 430

Ala Ala Gly Asn Ser Ala Asn Leu Ile Ile Leu Pro Ala Glu Asn Gly
        435                 440                 445

Phe Asp Ala Leu Arg Arg Gln Val Pro Val Arg Tyr Ser Val Arg Gly
450                 455                 460

Gly Lys Val Ile Ala Ser Thr Gln Pro Ala Gln Thr Thr Val Tyr Leu
465                 470                 475                 480

Glu Gln Pro Glu Ala Ile Asp Tyr Lys Arg Leu Glu His His His His
                485                 490                 495

His His

<210> SEQ ID NO 22
<211> LENGTH: 498
```

<212> TYPE: PRT
<213> ORGANISM: Artificial Sequence
<220> FEATURE:
<223> OTHER INFORMATION: RGD_EGF_EcCD_D314A

<400> SEQUENCE: 22

```
Met Ala Arg Gly Asp Asn Ser Asp Ser Glu Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
        35                  40                  45

Tyr Arg Asp Leu Lys Trp Trp Glu Leu Arg Pro Gly Gly Gly Gly Met
50                  55                  60

Ser Asn Asn Ala Leu Gln Thr Ile Ile Asn Ala Arg Leu Pro Gly Glu
65                  70                  75                  80

Glu Gly Leu Trp Gln Ile His Leu Gln Asp Gly Lys Ile Ser Ala Ile
                85                  90                  95

Asp Ala Gln Ser Gly Val Met Pro Ile Thr Glu Asn Ser Leu Asp Ala
            100                 105                 110

Glu Gln Gly Leu Val Ile Pro Pro Phe Val Glu Pro His Ile His Leu
        115                 120                 125

Asp Thr Thr Gln Thr Ala Gly Gln Pro Asn Trp Asn Gln Ser Gly Thr
130                 135                 140

Leu Phe Glu Gly Ile Glu Arg Trp Ala Glu Arg Lys Ala Leu Leu Thr
145                 150                 155                 160

His Asp Asp Val Lys Gln Arg Ala Trp Gln Thr Leu Lys Trp Gln Ile
                165                 170                 175

Ala Asn Gly Ile Gln His Val Arg Thr His Val Asp Val Ser Asp Ala
            180                 185                 190

Thr Leu Thr Ala Leu Lys Ala Met Leu Glu Val Lys Gln Glu Val Ala
        195                 200                 205

Pro Trp Ile Asp Leu Gln Ile Val Ala Phe Pro Gln Glu Gly Ile Leu
210                 215                 220

Ser Tyr Pro Asn Gly Glu Ala Leu Leu Glu Glu Ala Leu Arg Leu Arg
225                 230                 235                 240

Ala Asp Val Val Gly Ala Ile Pro His Phe Glu Phe Thr Arg Glu Tyr
                245                 250                 255

Gly Val Glu Ser Leu His Lys Thr Phe Ala Leu Ala Gln Lys Tyr Asp
            260                 265                 270

Arg Leu Ile Asp Val His Cys Asp Glu Ile Asp Asp Glu Gln Ser Arg
        275                 280                 285

Phe Val Glu Thr Val Ala Ala Leu Ala His His Glu Gly Met Gly Ala
290                 295                 300

Arg Val Thr Ala Ser His Thr Thr Ala Met His Ser Tyr Asn Gly Ala
305                 310                 315                 320

Tyr Thr Ser Arg Leu Phe Arg Leu Leu Lys Met Ser Gly Ile Asn Phe
                325                 330                 335

Val Ala Asn Pro Leu Val Asn Ile His Leu Gln Gly Arg Phe Asp Thr
            340                 345                 350

Tyr Pro Lys Arg Arg Gly Ile Thr Arg Val Lys Glu Met Leu Glu Ser
        355                 360                 365

Gly Ile Asn Val Cys Phe Gly His Asp Ala Val Phe Asp Pro Trp Tyr
370                 375                 380
```

```
Pro Leu Gly Thr Ala Asn Met Leu Gln Val Leu His Met Gly Leu His
385                 390                 395                 400

Val Cys Gln Leu Met Gly Tyr Gly Gln Ile Asn Asp Gly Leu Asn Leu
            405                 410                 415

Ile Thr His His Ser Ala Arg Thr Leu Asn Leu Gln Asp Tyr Gly Ile
            420                 425                 430

Ala Ala Gly Asn Ser Ala Asn Leu Ile Ile Leu Pro Ala Glu Asn Gly
            435                 440                 445

Phe Asp Ala Leu Arg Arg Gln Val Pro Val Arg Tyr Ser Val Arg Gly
    450                 455                 460

Gly Lys Val Ile Ala Ser Thr Gln Pro Ala Gln Thr Thr Val Tyr Leu
465                 470                 475                 480

Glu Gln Pro Glu Ala Ile Asp Tyr Lys Arg Leu Glu His His His His
                485                 490                 495

His His

<210> SEQ ID NO 23
<211> LENGTH: 504
<212> TYPE: PRT
<213> ORGANISM: Artificial Sequence
<220> FEATURE:
<223> OTHER INFORMATION: RGD4C_EGF_EcCD_WT

<400> SEQUENCE: 23

Met Ala Cys Asp Cys Arg Gly Asp Cys Phe Cys Asn Ser Asp Ser Glu
1               5                   10                  15

Cys Pro Leu Ser His Asp Gly Tyr Cys Leu His Asp Gly Val Cys Met
            20                  25                  30

Tyr Ile Glu Ala Leu Asp Lys Tyr Ala Cys Asn Cys Val Val Gly Tyr
            35                  40                  45

Ile Gly Glu Arg Cys Gln Tyr Arg Asp Leu Lys Trp Trp Glu Leu Arg
    50                  55                  60

Pro Gly Gly Gly Met Ser Asn Asn Ala Leu Gln Thr Ile Ile Asn
65                  70                  75                  80

Ala Arg Leu Pro Gly Glu Glu Gly Leu Trp Gln Ile His Leu Gln Asp
                85                  90                  95

Gly Lys Ile Ser Ala Ile Asp Ala Gln Ser Gly Val Met Pro Ile Thr
            100                 105                 110

Glu Asn Ser Leu Asp Ala Glu Gln Gly Leu Val Ile Pro Pro Phe Val
            115                 120                 125

Glu Pro His Ile His Leu Asp Thr Thr Gln Thr Ala Gly Gln Pro Asn
    130                 135                 140

Trp Asn Gln Ser Gly Thr Leu Phe Glu Gly Ile Glu Arg Trp Ala Glu
145                 150                 155                 160

Arg Lys Ala Leu Leu Thr His Asp Asp Val Lys Gln Arg Ala Trp Gln
                165                 170                 175

Thr Leu Lys Trp Gln Ile Ala Asn Gly Ile Gln His Val Arg Thr His
            180                 185                 190

Val Asp Val Ser Asp Ala Thr Leu Thr Ala Leu Lys Ala Met Leu Glu
            195                 200                 205

Val Lys Gln Glu Val Ala Pro Trp Ile Asp Leu Gln Ile Val Ala Phe
    210                 215                 220

Pro Gln Glu Gly Ile Leu Ser Tyr Pro Asn Gly Glu Ala Leu Leu Glu
225                 230                 235                 240

Glu Ala Leu Arg Leu Arg Ala Asp Val Val Gly Ala Ile Pro His Phe
```

-continued

```
                245                 250                 255
Glu Phe Thr Arg Glu Tyr Gly Val Glu Ser Leu His Lys Thr Phe Ala
            260                 265                 270
Leu Ala Gln Lys Tyr Asp Arg Leu Ile Asp Val His Cys Asp Glu Ile
        275                 280                 285
Asp Asp Glu Gln Ser Arg Phe Val Glu Thr Val Ala Ala Leu Ala His
    290                 295                 300
His Glu Gly Met Gly Ala Arg Val Thr Ala Ser His Thr Thr Ala Met
305                 310                 315                 320
His Ser Tyr Asn Gly Ala Tyr Thr Ser Arg Leu Phe Arg Leu Leu Lys
                325                 330                 335
Met Ser Gly Ile Asn Phe Val Ala Asn Pro Leu Val Asn Ile His Leu
            340                 345                 350
Gln Gly Arg Phe Asp Thr Tyr Pro Lys Arg Arg Gly Ile Thr Arg Val
        355                 360                 365
Lys Glu Met Leu Glu Ser Gly Ile Asn Val Cys Phe Gly His Asp Asp
    370                 375                 380
Val Phe Asp Pro Trp Tyr Pro Leu Gly Thr Ala Asn Met Leu Gln Val
385                 390                 395                 400
Leu His Met Gly Leu His Val Cys Gln Leu Met Gly Tyr Gly Gln Ile
                405                 410                 415
Asn Asp Gly Leu Asn Leu Ile Thr His His Ser Ala Arg Thr Leu Asn
            420                 425                 430
Leu Gln Asp Tyr Gly Ile Ala Ala Gly Asn Ser Ala Asn Leu Ile Ile
        435                 440                 445
Leu Pro Ala Glu Asn Gly Phe Asp Ala Leu Arg Arg Gln Val Pro Val
    450                 455                 460
Arg Tyr Ser Val Arg Gly Gly Lys Val Ile Ala Ser Thr Gln Pro Ala
465                 470                 475                 480
Gln Thr Thr Val Tyr Leu Glu Gln Pro Glu Ala Ile Asp Tyr Lys Arg
                485                 490                 495
Leu Glu His His His His His His
            500

<210> SEQ ID NO 24
<211> LENGTH: 504
<212> TYPE: PRT
<213> ORGANISM: Artificial Sequence
<220> FEATURE:
<223> OTHER INFORMATION: RGD4C_EGF_EcCD_D314A

<400> SEQUENCE: 24

Met Ala Cys Asp Cys Arg Gly Asp Cys Phe Cys Asn Ser Asp Ser Glu
1               5                   10                  15
Cys Pro Leu Ser His Asp Gly Tyr Cys Leu His Asp Gly Val Cys Met
            20                  25                  30
Tyr Ile Glu Ala Leu Asp Lys Tyr Ala Cys Asn Cys Val Val Gly Tyr
        35                  40                  45
Ile Gly Glu Arg Cys Gln Tyr Arg Asp Leu Lys Trp Trp Glu Leu Arg
    50                  55                  60
Pro Gly Gly Gly Gly Met Ser Asn Asn Ala Leu Gln Thr Ile Ile Asn
65                  70                  75                  80
Ala Arg Leu Pro Gly Glu Glu Gly Leu Trp Gln Ile His Leu Gln Asp
                85                  90                  95
Gly Lys Ile Ser Ala Ile Asp Ala Gln Ser Gly Val Met Pro Ile Thr
```

```
                100                 105                 110
        Glu Asn Ser Leu Asp Ala Glu Gln Gly Leu Val Ile Pro Pro Phe Val
                    115                 120                 125
        Glu Pro His Ile His Leu Asp Thr Thr Gln Thr Ala Gly Gln Pro Asn
            130                 135                 140
        Trp Asn Gln Ser Gly Thr Leu Phe Glu Gly Ile Glu Arg Trp Ala Glu
        145                 150                 155                 160
        Arg Lys Ala Leu Leu Thr His Asp Asp Val Lys Gln Arg Ala Trp Gln
                        165                 170                 175
        Thr Leu Lys Trp Gln Ile Ala Asn Gly Ile Gln His Val Arg Thr His
                    180                 185                 190
        Val Asp Val Ser Asp Ala Thr Leu Thr Ala Leu Lys Ala Met Leu Glu
                195                 200                 205
        Val Lys Gln Glu Val Ala Pro Trp Ile Asp Leu Gln Ile Val Ala Phe
            210                 215                 220
        Pro Gln Glu Gly Ile Leu Ser Tyr Pro Asn Gly Glu Ala Leu Leu Glu
        225                 230                 235                 240
        Glu Ala Leu Arg Leu Arg Ala Asp Val Val Gly Ala Ile Pro His Phe
                        245                 250                 255
        Glu Phe Thr Arg Glu Tyr Gly Val Glu Ser Leu His Lys Thr Phe Ala
                    260                 265                 270
        Leu Ala Gln Lys Tyr Asp Arg Leu Ile Asp Val His Cys Asp Glu Ile
                275                 280                 285
        Asp Asp Glu Gln Ser Arg Phe Val Glu Thr Val Ala Ala Leu Ala His
            290                 295                 300
        His Glu Gly Met Gly Ala Arg Val Thr Ala Ser His Thr Thr Ala Met
        305                 310                 315                 320
        His Ser Tyr Asn Gly Ala Tyr Thr Ser Arg Leu Phe Arg Leu Leu Lys
                        325                 330                 335
        Met Ser Gly Ile Asn Phe Val Ala Asn Pro Leu Val Asn Ile His Leu
                    340                 345                 350
        Gln Gly Arg Phe Asp Thr Tyr Pro Lys Arg Arg Gly Ile Thr Arg Val
                355                 360                 365
        Lys Glu Met Leu Glu Ser Gly Ile Asn Val Cys Phe Gly His Asp Ala
            370                 375                 380
        Val Phe Asp Pro Trp Tyr Pro Leu Gly Thr Ala Asn Met Leu Gln Val
        385                 390                 395                 400
        Leu His Met Gly Leu His Val Cys Gln Leu Met Gly Tyr Gly Gln Ile
                        405                 410                 415
        Asn Asp Gly Leu Asn Leu Ile Thr His His Ser Ala Arg Thr Leu Asn
                    420                 425                 430
        Leu Gln Asp Tyr Gly Ile Ala Ala Gly Asn Ser Ala Asn Leu Ile Ile
                435                 440                 445
        Leu Pro Ala Glu Asn Gly Phe Asp Ala Leu Arg Arg Gln Val Pro Val
            450                 455                 460
        Arg Tyr Ser Val Arg Gly Gly Lys Val Ile Ala Ser Thr Gln Pro Ala
        465                 470                 475                 480
        Gln Thr Thr Val Tyr Leu Glu Gln Pro Glu Ala Ile Asp Tyr Lys Arg
                        485                 490                 495
        Leu Glu His His His His His His
                    500

<210> SEQ ID NO 25
```

<211> LENGTH: 496
<212> TYPE: PRT
<213> ORGANISM: Artificial Sequence
<220> FEATURE:
<223> OTHER INFORMATION: EcCD_WT_RGD_EGF

<400> SEQUENCE: 25

```
Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Arg Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
    370                 375                 380
```

```
Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg Pro Gly Gly Gly Gly
            420                 425                 430

Arg Gly Asp Asn Ser Asp Ser Glu Cys Pro Leu Ser His Asp Gly Tyr
        435                 440                 445

Cys Leu His Asp Gly Val Cys Met Tyr Ile Glu Ala Leu Asp Lys Tyr
    450                 455                 460

Ala Cys Asn Cys Val Val Gly Tyr Ile Gly Glu Arg Cys Gln Tyr Arg
465                 470                 475                 480

Asp Leu Lys Trp Trp Glu Leu Arg Leu Glu His His His His His
                485                 490                 495

<210> SEQ ID NO 26
<211> LENGTH: 496
<212> TYPE: PRT
<213> ORGANISM: Artificial Sequence
<220> FEATURE:
<223> OTHER INFORMATION: EcCD_D314A_RGD_EGF

<400> SEQUENCE: 26

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65              70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Ala Leu Arg Leu
                165                 170                 175

Arg Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255
```

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Ala Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg Pro Gly Gly Gly Gly
            420                 425                 430

Arg Gly Asp Asn Ser Asp Ser Glu Cys Pro Leu Ser His Asp Gly Tyr
        435                 440                 445

Cys Leu His Asp Gly Val Cys Met Tyr Ile Glu Ala Leu Asp Lys Tyr
    450                 455                 460

Ala Cys Asn Cys Val Val Gly Tyr Ile Gly Glu Arg Cys Gln Tyr Arg
465                 470                 475                 480

Asp Leu Lys Trp Trp Glu Leu Arg Leu Glu His His His His His
                485                 490                 495

<210> SEQ ID NO 27
<211> LENGTH: 502
<212> TYPE: PRT
<213> ORGANISM: Artificial Sequence
<220> FEATURE:
<223> OTHER INFORMATION: EcCD_WT_RGD4C_EGF

<400> SEQUENCE: 27

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
            165                 170                 175

Arg Ala Asp Val Val Gly Ala Ile Pro His Phe Glu Phe Thr Arg Glu
        180                 185                 190

Tyr Gly Val Glu Ser Leu His Lys Thr Phe Ala Leu Ala Gln Lys Tyr
    195                 200                 205

Asp Arg Leu Ile Asp Val His Cys Asp Glu Ile Asp Asp Glu Gln Ser
210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
            245                 250                 255

Ala Tyr Thr Ser Arg Leu Phe Arg Leu Leu Lys Met Ser Gly Ile Asn
        260                 265                 270

Phe Val Ala Asn Pro Leu Val Asn Ile His Leu Gln Gly Arg Phe Asp
    275                 280                 285

Thr Tyr Pro Lys Arg Arg Gly Ile Thr Arg Val Lys Glu Met Leu Glu
290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
            325                 330                 335

His Val Cys Gln Leu Met Gly Tyr Gly Gln Ile Asn Asp Gly Leu Asn
        340                 345                 350

Leu Ile Thr His His Ser Ala Arg Thr Leu Asn Leu Gln Asp Tyr Gly
    355                 360                 365

Ile Ala Ala Gly Asn Ser Ala Asn Leu Ile Ile Leu Pro Ala Glu Asn
370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
            405                 410                 415

Leu Glu Gln Pro Glu Ala Ile Asp Tyr Lys Arg Pro Gly Gly Gly Gly
        420                 425                 430

Cys Asp Cys Arg Gly Asp Cys Phe Cys Asn Ser Asp Ser Glu Cys Pro
    435                 440                 445

Leu Ser His Asp Gly Tyr Cys Leu His Asp Gly Val Cys Met Tyr Ile
450                 455                 460

Glu Ala Leu Asp Lys Tyr Ala Cys Asn Cys Val Val Gly Tyr Ile Gly
465                 470                 475                 480

Glu Arg Cys Gln Tyr Arg Asp Leu Lys Trp Trp Glu Leu Arg Leu Glu
            485                 490                 495

His His His His His His
            500

<210> SEQ ID NO 28
<211> LENGTH: 502
<212> TYPE: PRT
<213> ORGANISM: Artificial Sequence
<220> FEATURE:

<223> OTHER INFORMATION: EcCD_D314A_RGD4C_EGF

<400> SEQUENCE: 28

```
Met Ser Asn Asn Ala Leu Gln Thr Ile Ile Asn Ala Arg Leu Pro Gly
1               5                   10                  15
Glu Glu Gly Leu Trp Gln Ile His Leu Gln Asp Gly Lys Ile Ser Ala
            20                  25                  30
Ile Asp Ala Gln Ser Gly Val Met Pro Ile Thr Glu Asn Ser Leu Asp
        35                  40                  45
Ala Glu Gln Gly Leu Val Ile Pro Pro Phe Val Glu Pro His Ile His
    50                  55                  60
Leu Asp Thr Thr Gln Thr Ala Gly Gln Pro Asn Trp Asn Gln Ser Gly
65                  70                  75                  80
Thr Leu Phe Glu Gly Ile Glu Arg Trp Ala Glu Arg Lys Ala Leu Leu
                85                  90                  95
Thr His Asp Asp Val Lys Gln Arg Ala Trp Gln Thr Leu Lys Trp Gln
            100                 105                 110
Ile Ala Asn Gly Ile Gln His Val Arg Thr His Val Asp Val Ser Asp
        115                 120                 125
Ala Thr Leu Thr Ala Leu Lys Ala Met Leu Glu Val Lys Gln Glu Val
    130                 135                 140
Ala Pro Trp Ile Asp Leu Gln Ile Val Ala Phe Pro Gln Glu Gly Ile
145                 150                 155                 160
Leu Ser Tyr Pro Asn Gly Glu Ala Leu Leu Glu Glu Ala Leu Arg Leu
                165                 170                 175
Arg Ala Asp Val Val Gly Ala Ile Pro His Phe Glu Phe Thr Arg Glu
            180                 185                 190
Tyr Gly Val Glu Ser Leu His Lys Thr Phe Ala Leu Ala Gln Lys Tyr
        195                 200                 205
Asp Arg Leu Ile Asp Val His Cys Asp Glu Ile Asp Asp Glu Gln Ser
    210                 215                 220
Arg Phe Val Glu Thr Val Ala Ala Leu Ala His His Glu Gly Met Gly
225                 230                 235                 240
Ala Arg Val Thr Ala Ser His Thr Thr Ala Met His Ser Tyr Asn Gly
                245                 250                 255
Ala Tyr Thr Ser Arg Leu Phe Arg Leu Leu Lys Met Ser Gly Ile Asn
            260                 265                 270
Phe Val Ala Asn Pro Leu Val Asn Ile His Leu Gln Gly Arg Phe Asp
        275                 280                 285
Thr Tyr Pro Lys Arg Arg Gly Ile Thr Arg Val Lys Glu Met Leu Glu
    290                 295                 300
Ser Gly Ile Asn Val Cys Phe Gly His Asp Ala Val Phe Asp Pro Trp
305                 310                 315                 320
Tyr Pro Leu Gly Thr Ala Asn Met Leu Gln Val Leu His Met Gly Leu
                325                 330                 335
His Val Cys Gln Leu Met Gly Tyr Gly Gln Ile Asn Asp Gly Leu Asn
            340                 345                 350
Leu Ile Thr His His Ser Ala Arg Thr Leu Asn Leu Gln Asp Tyr Gly
        355                 360                 365
Ile Ala Ala Gly Asn Ser Ala Asn Leu Ile Ile Leu Pro Ala Glu Asn
    370                 375                 380
Gly Phe Asp Ala Leu Arg Arg Gln Val Pro Val Arg Tyr Ser Val Arg
385                 390                 395                 400
```

```
Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg Pro Gly Gly Gly Gly
            420                 425                 430

Cys Asp Cys Arg Gly Asp Cys Phe Cys Asn Ser Asp Ser Glu Cys Pro
            435                 440                 445

Leu Ser His Asp Gly Tyr Cys Leu His Asp Gly Val Cys Met Tyr Ile
450                 455                 460

Glu Ala Leu Asp Lys Tyr Ala Cys Asn Cys Val Val Gly Tyr Ile Gly
465                 470                 475                 480

Glu Arg Cys Gln Tyr Arg Asp Leu Lys Trp Trp Glu Leu Arg Leu Glu
                485                 490                 495

His His His His His His
            500

<210> SEQ ID NO 29
<211> LENGTH: 566
<212> TYPE: PRT
<213> ORGANISM: Artificial Sequence
<220> FEATURE:
<223> OTHER INFORMATION: RGD_VEGF_EcCD_WT

<400> SEQUENCE: 29

Met Gly Arg Gly Asp Ala Pro Met Ala Glu Gly Gly Gly Gln Asn His
1               5                   10                  15

His Glu Val Val Lys Phe Met Asp Val Tyr Gln Arg Ser Tyr Cys His
                20                  25                  30

Pro Ile Glu Thr Leu Val Asp Ile Phe Gln Glu Tyr Pro Asp Glu Ile
            35                  40                  45

Glu Tyr Ile Phe Lys Pro Ser Cys Val Pro Leu Met Arg Cys Gly Gly
        50                  55                  60

Cys Cys Asn Asp Glu Gly Leu Glu Cys Val Pro Thr Glu Glu Ser Asn
65                  70                  75                  80

Ile Thr Met Gln Ile Met Arg Ile Lys Pro His Gln Gly Gln His Ile
                85                  90                  95

Gly Glu Met Ser Phe Leu Gln His Asn Lys Cys Glu Cys Arg Pro Lys
                100                 105                 110

Lys Asp Arg Ala Arg Gln Glu Lys Cys Asp Lys Pro Arg Arg Pro Gly
            115                 120                 125

Gly Gly Gly Met Ser Asn Asn Ala Leu Gln Thr Ile Ile Asn Ala Arg
130                 135                 140

Leu Pro Gly Glu Glu Gly Leu Trp Gln Ile His Leu Gln Asp Gly Lys
145                 150                 155                 160

Ile Ser Ala Ile Asp Ala Gln Ser Gly Val Met Pro Ile Thr Glu Asn
                165                 170                 175

Ser Leu Asp Ala Glu Gln Gly Leu Val Ile Pro Pro Phe Val Glu Pro
            180                 185                 190

His Ile His Leu Asp Thr Thr Gln Thr Ala Gly Gln Pro Asn Trp Asn
        195                 200                 205

Gln Ser Gly Thr Leu Phe Glu Gly Ile Glu Arg Trp Ala Glu Arg Lys
    210                 215                 220

Ala Leu Leu Thr His Asp Asp Val Lys Gln Arg Ala Trp Gln Thr Leu
225                 230                 235                 240

Lys Trp Gln Ile Ala Asn Gly Ile Gln His Val Arg Thr His Val Asp
                245                 250                 255
```

Val Ser Asp Ala Thr Leu Thr Ala Leu Lys Ala Met Leu Glu Val Lys
        260                 265                 270

Gln Glu Val Ala Pro Trp Ile Asp Leu Gln Ile Val Ala Phe Pro Gln
        275                 280                 285

Glu Gly Ile Leu Ser Tyr Pro Asn Gly Glu Ala Leu Leu Glu Glu Ala
        290                 295                 300

Leu Arg Leu Arg Ala Asp Val Val Gly Ala Ile Pro His Phe Glu Phe
305                 310                 315                 320

Thr Arg Glu Tyr Gly Val Glu Ser Leu His Lys Thr Phe Ala Leu Ala
                325                 330                 335

Gln Lys Tyr Asp Arg Leu Ile Asp Val His Cys Asp Glu Ile Asp Asp
        340                 345                 350

Glu Gln Ser Arg Phe Val Glu Thr Val Ala Ala Leu Ala His His Glu
        355                 360                 365

Gly Met Gly Ala Arg Val Thr Ala Ser His Thr Thr Ala Met His Ser
        370                 375                 380

Tyr Asn Gly Ala Tyr Thr Ser Arg Leu Phe Arg Leu Leu Lys Met Ser
385                 390                 395                 400

Gly Ile Asn Phe Val Ala Asn Pro Leu Val Asn Ile His Leu Gln Gly
                405                 410                 415

Arg Phe Asp Thr Tyr Pro Lys Arg Arg Gly Ile Thr Arg Val Lys Glu
        420                 425                 430

Met Leu Glu Ser Gly Ile Asn Val Cys Phe Gly His Asp Asp Val Phe
        435                 440                 445

Asp Pro Trp Tyr Pro Leu Gly Thr Ala Asn Met Leu Gln Val Leu His
        450                 455                 460

Met Gly Leu His Val Cys Gln Leu Met Gly Tyr Gly Gln Ile Asn Asp
465                 470                 475                 480

Gly Leu Asn Leu Ile Thr His His Ser Ala Arg Thr Leu Asn Leu Gln
                485                 490                 495

Asp Tyr Gly Ile Ala Ala Gly Asn Ser Ala Asn Leu Ile Ile Leu Pro
        500                 505                 510

Ala Glu Asn Gly Phe Asp Ala Leu Arg Arg Gln Val Pro Val Arg Tyr
        515                 520                 525

Ser Val Arg Gly Gly Lys Val Ile Ala Ser Thr Gln Pro Ala Gln Thr
        530                 535                 540

Thr Val Tyr Leu Glu Gln Pro Glu Ala Ile Asp Tyr Lys Arg Leu Glu
545                 550                 555                 560

His His His His His His
                565

<210> SEQ ID NO 30
<211> LENGTH: 566
<212> TYPE: PRT
<213> ORGANISM: Artificial Sequence
<220> FEATURE:
<223> OTHER INFORMATION: RGD_VEGF_EcCD_D314A

<400> SEQUENCE: 30

Met Gly Arg Gly Asp Ala Pro Met Ala Glu Gly Gly Gly Gln Asn His
1               5                   10                  15

His Glu Val Val Lys Phe Met Asp Val Tyr Gln Arg Ser Tyr Cys His
                20                  25                  30

Pro Ile Glu Thr Leu Val Asp Ile Phe Gln Glu Tyr Pro Asp Glu Ile
        35                  40                  45

```
Glu Tyr Ile Phe Lys Pro Ser Cys Val Pro Leu Met Arg Cys Gly Gly
     50                  55                  60

Cys Cys Asn Asp Glu Gly Leu Glu Cys Val Pro Thr Glu Glu Ser Asn
 65                  70                  75                  80

Ile Thr Met Gln Ile Met Arg Ile Lys Pro His Gln Gly Gln His Ile
                 85                  90                  95

Gly Glu Met Ser Phe Leu Gln His Asn Lys Cys Glu Cys Arg Pro Lys
            100                 105                 110

Lys Asp Arg Ala Arg Gln Glu Lys Cys Asp Lys Pro Arg Arg Pro Gly
            115                 120                 125

Gly Gly Gly Met Ser Asn Asn Ala Leu Gln Thr Ile Ile Asn Ala Arg
130                 135                 140

Leu Pro Gly Glu Glu Gly Leu Trp Gln Ile His Leu Gln Asp Gly Lys
145                 150                 155                 160

Ile Ser Ala Ile Asp Ala Gln Ser Gly Val Met Pro Ile Thr Glu Asn
                165                 170                 175

Ser Leu Asp Ala Glu Gln Gly Leu Val Ile Pro Pro Phe Val Glu Pro
            180                 185                 190

His Ile His Leu Asp Thr Thr Gln Thr Ala Gly Gln Pro Asn Trp Asn
            195                 200                 205

Gln Ser Gly Thr Leu Phe Glu Gly Ile Glu Arg Trp Ala Glu Arg Lys
210                 215                 220

Ala Leu Leu Thr His Asp Asp Val Lys Gln Arg Ala Trp Gln Thr Leu
225                 230                 235                 240

Lys Trp Gln Ile Ala Asn Gly Ile Gln His Val Arg Thr His Val Asp
                245                 250                 255

Val Ser Asp Ala Thr Leu Thr Ala Leu Lys Ala Met Leu Glu Val Lys
            260                 265                 270

Gln Glu Val Ala Pro Trp Ile Asp Leu Gln Ile Val Ala Phe Pro Gln
            275                 280                 285

Glu Gly Ile Leu Ser Tyr Pro Asn Gly Glu Ala Leu Leu Glu Glu Ala
290                 295                 300

Leu Arg Leu Arg Ala Asp Val Val Gly Ala Ile Pro His Phe Glu Phe
305                 310                 315                 320

Thr Arg Glu Tyr Gly Val Glu Ser Leu His Lys Thr Phe Ala Leu Ala
                325                 330                 335

Gln Lys Tyr Asp Arg Leu Ile Asp Val His Cys Asp Glu Ile Asp Asp
            340                 345                 350

Glu Gln Ser Arg Phe Val Glu Thr Val Ala Ala Leu Ala His His Glu
            355                 360                 365

Gly Met Gly Ala Arg Val Thr Ala Ser His Thr Thr Ala Met His Ser
370                 375                 380

Tyr Asn Gly Ala Tyr Thr Ser Arg Leu Phe Arg Leu Leu Lys Met Ser
385                 390                 395                 400

Gly Ile Asn Phe Val Ala Asn Pro Leu Val Asn Ile His Leu Gln Gly
                405                 410                 415

Arg Phe Asp Thr Tyr Pro Lys Arg Arg Gly Ile Thr Arg Val Lys Glu
            420                 425                 430

Met Leu Glu Ser Gly Ile Asn Val Cys Phe Gly His Asp Ala Val Phe
            435                 440                 445

Asp Pro Trp Tyr Pro Leu Gly Thr Ala Asn Met Leu Gln Val Leu His
450                 455                 460

Met Gly Leu His Val Cys Gln Leu Met Gly Tyr Gly Gln Ile Asn Asp
```

|       |       |       |       |       |       |       |       |
|-------|-------|-------|-------|-------|-------|-------|-------|
| 465   |       | 470   |       | 475   |       | 480   |       |

Gly Leu Asn Leu Ile Thr His His Ser Ala Arg Thr Leu Asn Leu Gln
                485                 490                 495

Asp Tyr Gly Ile Ala Ala Gly Asn Ser Ala Asn Leu Ile Ile Leu Pro
            500                 505                 510

Ala Glu Asn Gly Phe Asp Ala Leu Arg Arg Gln Val Pro Val Arg Tyr
            515                 520                 525

Ser Val Arg Gly Gly Lys Val Ile Ala Ser Thr Gln Pro Ala Gln Thr
530                 535                 540

Thr Val Tyr Leu Glu Gln Pro Glu Ala Ile Asp Tyr Lys Arg Leu Glu
545                 550                 555                 560

His His His His His His
                565

<210> SEQ ID NO 31
<211> LENGTH: 572
<212> TYPE: PRT
<213> ORGANISM: Artificial Sequence
<220> FEATURE:
<223> OTHER INFORMATION: RGD4C_VEGF_EcCD_WT

<400> SEQUENCE: 31

Met Gly Cys Asp Cys Arg Gly Asp Cys Phe Cys Ala Pro Met Ala Glu
1               5                   10                  15

Gly Gly Gly Gln Asn His His Glu Val Val Lys Phe Met Asp Val Tyr
            20                  25                  30

Gln Arg Ser Tyr Cys His Pro Ile Glu Thr Leu Val Asp Ile Phe Gln
        35                  40                  45

Glu Tyr Pro Asp Glu Ile Glu Tyr Ile Phe Lys Pro Ser Cys Val Pro
    50                  55                  60

Leu Met Arg Cys Gly Gly Cys Cys Asn Asp Glu Gly Leu Glu Cys Val
65                  70                  75                  80

Pro Thr Glu Glu Ser Asn Ile Thr Met Gln Ile Met Arg Ile Lys Pro
                85                  90                  95

His Gln Gly Gln His Ile Gly Glu Met Ser Phe Leu Gln His Asn Lys
            100                 105                 110

Cys Glu Cys Arg Pro Lys Lys Asp Arg Ala Arg Gln Glu Lys Cys Asp
        115                 120                 125

Lys Pro Arg Arg Pro Gly Gly Gly Gly Met Ser Asn Asn Ala Leu Gln
    130                 135                 140

Thr Ile Ile Asn Ala Arg Leu Pro Gly Glu Glu Gly Leu Trp Gln Ile
145                 150                 155                 160

His Leu Gln Asp Gly Lys Ile Ser Ala Ile Asp Ala Gln Ser Gly Val
                165                 170                 175

Met Pro Ile Thr Glu Asn Ser Leu Asp Ala Glu Gln Gly Leu Val Ile
            180                 185                 190

Pro Pro Phe Val Glu Pro His Ile His Leu Asp Thr Thr Gln Thr Ala
        195                 200                 205

Gly Gln Pro Asn Trp Asn Gln Ser Gly Thr Leu Phe Glu Gly Ile Glu
    210                 215                 220

Arg Trp Ala Glu Arg Lys Ala Leu Leu Thr His Asp Asp Val Lys Gln
225                 230                 235                 240

Arg Ala Trp Gln Thr Leu Lys Trp Gln Ile Ala Asn Gly Ile Gln His
                245                 250                 255

Val Arg Thr His Val Asp Val Ser Asp Ala Thr Leu Thr Ala Leu Lys

```
                  260                 265                 270
Ala Met Leu Glu Val Lys Gln Glu Val Ala Pro Trp Ile Asp Leu Gln
            275                 280                 285

Ile Val Ala Phe Pro Gln Glu Gly Ile Leu Ser Tyr Pro Asn Gly Glu
        290                 295                 300

Ala Leu Leu Glu Glu Ala Leu Arg Leu Arg Ala Asp Val Val Gly Ala
305                 310                 315                 320

Ile Pro His Phe Glu Phe Thr Arg Glu Tyr Gly Val Glu Ser Leu His
                325                 330                 335

Lys Thr Phe Ala Leu Ala Gln Lys Tyr Asp Arg Leu Ile Asp Val His
            340                 345                 350

Cys Asp Glu Ile Asp Asp Glu Gln Ser Arg Phe Val Glu Thr Val Ala
        355                 360                 365

Ala Leu Ala His His Glu Gly Met Gly Ala Arg Val Thr Ala Ser His
370                 375                 380

Thr Thr Ala Met His Ser Tyr Asn Gly Ala Tyr Thr Ser Arg Leu Phe
385                 390                 395                 400

Arg Leu Leu Lys Met Ser Gly Ile Asn Phe Val Ala Asn Pro Leu Val
                405                 410                 415

Asn Ile His Leu Gln Gly Arg Phe Asp Thr Tyr Pro Lys Arg Arg Gly
            420                 425                 430

Ile Thr Arg Val Lys Glu Met Leu Glu Ser Gly Ile Asn Val Cys Phe
        435                 440                 445

Gly His Asp Asp Val Phe Asp Pro Trp Tyr Pro Leu Gly Thr Ala Asn
450                 455                 460

Met Leu Gln Val Leu His Met Gly Leu His Val Cys Gln Leu Met Gly
465                 470                 475                 480

Tyr Gly Gln Ile Asn Asp Gly Leu Asn Leu Ile Thr His His Ser Ala
                485                 490                 495

Arg Thr Leu Asn Leu Gln Asp Tyr Gly Ile Ala Ala Gly Asn Ser Ala
            500                 505                 510

Asn Leu Ile Ile Leu Pro Ala Glu Asn Gly Phe Asp Ala Leu Arg Arg
        515                 520                 525

Gln Val Pro Val Arg Tyr Ser Val Arg Gly Gly Lys Val Ile Ala Ser
530                 535                 540

Thr Gln Pro Ala Gln Thr Thr Val Tyr Leu Glu Gln Pro Glu Ala Ile
545                 550                 555                 560

Asp Tyr Lys Arg Leu Glu His His His His His
                565                 570

<210> SEQ ID NO 32
<211> LENGTH: 572
<212> TYPE: PRT
<213> ORGANISM: Artificial Sequence
<220> FEATURE:
<223> OTHER INFORMATION: RGD4C_VEGF_EcCD_D314A

<400> SEQUENCE: 32

Met Gly Cys Asp Cys Arg Gly Asp Cys Phe Cys Ala Pro Met Ala Glu
1               5                   10                  15

Gly Gly Gly Gln Asn His His Glu Val Val Lys Phe Met Asp Val Tyr
            20                  25                  30

Gln Arg Ser Tyr Cys His Pro Ile Glu Thr Leu Val Asp Ile Phe Gln
        35                  40                  45

Glu Tyr Pro Asp Glu Ile Glu Tyr Ile Phe Lys Pro Ser Cys Val Pro
```

-continued

```
            50                  55                  60
Leu Met Arg Cys Gly Gly Cys Cys Asn Asp Glu Gly Leu Glu Cys Val
65                  70                  75                  80

Pro Thr Glu Glu Ser Asn Ile Thr Met Gln Ile Met Arg Ile Lys Pro
                85                  90                  95

His Gln Gly Gln His Ile Gly Glu Met Ser Phe Leu Gln His Asn Lys
            100                 105                 110

Cys Glu Cys Arg Pro Lys Lys Asp Arg Ala Arg Gln Glu Lys Cys Asp
            115                 120                 125

Lys Pro Arg Arg Pro Gly Gly Gly Met Ser Asn Asn Ala Leu Gln
            130                 135                 140

Thr Ile Ile Asn Ala Arg Leu Pro Gly Glu Glu Gly Leu Trp Gln Ile
145                 150                 155                 160

His Leu Gln Asp Gly Lys Ile Ser Ala Ile Asp Ala Gln Ser Gly Val
            165                 170                 175

Met Pro Ile Thr Glu Asn Ser Leu Asp Ala Glu Gln Gly Leu Val Ile
            180                 185                 190

Pro Pro Phe Val Glu Pro His Ile His Leu Asp Thr Thr Gln Thr Ala
            195                 200                 205

Gly Gln Pro Asn Trp Asn Gln Ser Gly Thr Leu Phe Glu Gly Ile Glu
            210                 215                 220

Arg Trp Ala Glu Arg Lys Ala Leu Leu Thr His Asp Val Lys Gln
225                 230                 235                 240

Arg Ala Trp Gln Thr Leu Lys Trp Gln Ile Ala Asn Gly Ile Gln His
            245                 250                 255

Val Arg Thr His Val Asp Val Ser Asp Ala Thr Leu Thr Ala Leu Lys
            260                 265                 270

Ala Met Leu Glu Val Lys Gln Glu Val Ala Pro Trp Ile Asp Leu Gln
            275                 280                 285

Ile Val Ala Phe Pro Gln Glu Gly Ile Leu Ser Tyr Pro Asn Gly Glu
            290                 295                 300

Ala Leu Leu Glu Glu Ala Leu Arg Leu Arg Ala Asp Val Val Gly Ala
305                 310                 315                 320

Ile Pro His Phe Glu Phe Thr Arg Glu Tyr Gly Val Glu Ser Leu His
            325                 330                 335

Lys Thr Phe Ala Leu Ala Gln Lys Tyr Asp Arg Leu Ile Asp Val His
            340                 345                 350

Cys Asp Glu Ile Asp Asp Glu Gln Ser Arg Phe Val Glu Thr Val Ala
            355                 360                 365

Ala Leu Ala His His Glu Gly Met Gly Ala Arg Val Thr Ala Ser His
            370                 375                 380

Thr Thr Ala Met His Ser Tyr Asn Gly Ala Tyr Thr Ser Arg Leu Phe
385                 390                 395                 400

Arg Leu Leu Lys Met Ser Gly Ile Asn Phe Val Ala Asn Pro Leu Val
            405                 410                 415

Asn Ile His Leu Gln Gly Arg Phe Asp Thr Tyr Pro Lys Arg Arg Gly
            420                 425                 430

Ile Thr Arg Val Lys Glu Met Leu Glu Ser Gly Ile Asn Val Cys Phe
            435                 440                 445

Gly His Asp Ala Val Phe Asp Pro Trp Tyr Pro Leu Gly Thr Ala Asn
            450                 455                 460

Met Leu Gln Val Leu His Met Gly Leu His Val Cys Gln Leu Met Gly
465                 470                 475                 480
```

```
Tyr Gly Gln Ile Asn Asp Gly Leu Asn Leu Ile Thr His His Ser Ala
                485                 490                 495

Arg Thr Leu Asn Leu Gln Asp Tyr Gly Ile Ala Ala Gly Asn Ser Ala
            500                 505                 510

Asn Leu Ile Ile Leu Pro Ala Glu Asn Gly Phe Asp Ala Leu Arg Arg
        515                 520                 525

Gln Val Pro Val Arg Tyr Ser Val Arg Gly Gly Lys Val Ile Ala Ser
    530                 535                 540

Thr Gln Pro Ala Gln Thr Thr Val Tyr Leu Glu Gln Pro Glu Ala Ile
545                 550                 555                 560

Asp Tyr Lys Arg Leu Glu His His His His His His
                565                 570
```